(12) United States Patent
Song et al.

(10) Patent No.: US 10,344,286 B2
(45) Date of Patent: Jul. 9, 2019

(54) MICROORGANISM INCLUDING GENE ENCODING PROTEIN HAVING HYDROXYLASE ACTIVITY AND METHOD OF REDUCING CONCENTRATION OF FLUORINATED METHANE IN SAMPLE USING THE SAME

(71) Applicant: Samsung Electronics Co., Ltd., Suwon-si, Gyeonggi-do (KR)

(72) Inventors: Seunghoon Song, Yongin-si (KR); Taeyong Kim, Daejeon-si (KR); Jinhwan Park, Suwon-si (KR); Joonsong Park, Seoul (KR); Yukyung Jung, Hwaseong-si (KR); Hunsu Chu, Seoul (KR); Jiyoon Song, Seoul (KR); Kwangmyung Cho, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/154,575

(22) Filed: May 13, 2016

(65) Prior Publication Data

US 2016/0333359 A1    Nov. 17, 2016

(30) Foreign Application Priority Data

| May 13, 2015 | (KR) | .......................... 10-2015-0066949 |
| Oct. 23, 2015 | (KR) | .......................... 10-2015-0148032 |
| Dec. 7, 2015 | (KR) | .......................... 10-2015-0173293 |
| Dec. 23, 2015 | (KR) | .......................... 10-2015-0185093 |
| Apr. 21, 2016 | (KR) | .......................... 10-2016-0048960 |

(51) Int. Cl.

| C12P 7/02 | (2006.01) |
| C12P 7/08 | (2006.01) |
| C12N 9/02 | (2006.01) |
| C12N 15/70 | (2006.01) |
| C12N 9/14 | (2006.01) |
| B01D 53/70 | (2006.01) |
| B01D 53/84 | (2006.01) |
| C02F 3/34 | (2006.01) |
| C02F 101/36 | (2006.01) |

(52) U.S. Cl.
CPC ............ *C12N 15/70* (2013.01); *B01D 53/70* (2013.01); *B01D 53/84* (2013.01); *C02F 3/34* (2013.01); *C12N 9/0071* (2013.01); *C12N 9/0073* (2013.01); *C12N 9/14* (2013.01); *B01D 2251/95* (2013.01); *B01D 2257/2066* (2013.01); *C02F 2101/36* (2013.01); *C12Y 114/00* (2013.01); *C12Y 114/13025* (2013.01); *C12Y 308/01005* (2013.01)

(58) Field of Classification Search
None
See application file for complete search history.

(56) References Cited

U.S. PATENT DOCUMENTS

| 5,316,940 | A | 5/1994 | Georgiou et al. |
| 5,559,278 | A | 9/1996 | Mouk et al. |
| 5,637,499 | A | 6/1997 | Turick |
| 6,100,074 | A | 8/2000 | Flitsch et al. |
| 6,794,168 | B1 | 9/2004 | Wong et al. |
| 6,945,925 | B2 | 9/2005 | Pooler et al. |
| 7,579,176 | B2 | 8/2009 | Herrema et al. |
| 8,101,395 | B2 | 1/2012 | Davis et al. |
| 8,153,411 | B2 | 4/2012 | Short et al. |
| 8,535,910 | B2 | 9/2013 | Davis et al. |
| 8,715,988 | B2 | 5/2014 | Arnold et al. |
| 2005/0027155 | A1 | 2/2005 | Pooler et al. |
| 2008/0287617 | A1* | 11/2008 | Holtcamp ............... C08F 10/00 526/116 |
| 2010/0286463 | A1* | 11/2010 | Tarancon, III ........... A62D 3/34 588/319 |
| 2014/0072965 | A1 | 3/2014 | Padilla-Crespo et al. |
| 2015/0010945 | A1 | 1/2015 | Krajmalnik-Brown et al. |
| 2016/0244785 | A1* | 8/2016 | Koepke ................ C12N 9/0073 |

FOREIGN PATENT DOCUMENTS

| EP | 1433856 A1 | 6/2004 |
| EP | 1500704 A1 | 1/2005 |
| JP | 1994-245761 A | 9/1994 |
| JP | 2005-013872 A | 6/2003 |
| JP | 2008-086850 A | 4/2008 |
| JP | 2010-517579 A | 5/2010 |
| KR | 0234348 B1 | 12/1999 |
| KR | 0392185 B1 | 12/2001 |
| KR | 0487610 B1 | 1/2003 |
| KR | 2005-0028278 A | 3/2005 |

(Continued)

OTHER PUBLICATIONS

Chang, R., "Chemistry", Fourth Ed., McGraw-Hill Inc., New York, 1991, p. A20 (Year: 1991).*

(Continued)

*Primary Examiner* — David Steadman
(74) *Attorney, Agent, or Firm* — Leydig, Voit & Mayer, Ltd.

(57) ABSTRACT

A microorganism including a foreign gene encoding a protein having a hydroxylase activity that reduces the concentration of $CH_nF_{4-n}$ (n is an integer of 0 to 3) in a sample, as well as a composition including the microorganism or lysate thereof, and a method of reducing the concentration of $CH_nF_{4-n}$ in a sample using the microorganism or lysate.

8 Claims, 17 Drawing Sheets

Specification includes a Sequence Listing.

(56) References Cited

FOREIGN PATENT DOCUMENTS

| KR | 2009-0129430 A | 12/2009 | | |
|---|---|---|---|---|
| WO | WO 98/36080 A1 | 8/1998 | | |
| WO | WO 2008/016709 A2 | 2/2008 | | |
| WO | WO-2017087731 A1 | * | 5/2017 | ............... C12N 1/00 |

OTHER PUBLICATIONS

Furuto et al., J. Mol. Catalysis A: Chem. 144:, 257-261, 1999 (Year: 1999).*

Beauvais et al., Biochem. Biophys. Res. Comm. 338:262-266, 2005 (Year: 2005).*

Matheson et al., Appl. Environ. Microbiol. 63:2952-2956, 1997 (Year: 1997).*

King, G.M., FEMS Microbiol. Ecol. 22:10-109, 1997 (Year: 1997).*

Koudelakova et al., Biochem. J. 435:345-354, 2011 (Year: 2011).*

Kmunicek et al., Biochemistry 44:3390-3401, 2005 (Year: 2005).*

EC 1.14.13, 5 pages; obtained from http://www.sbcs.qmul.ac.uk/iubmb/enzyme/EC1/14/13/, last viewed on Oct. 30, 2018 (Year: 2018).*

Sirajuddin et al., Biochemistry 54:2283-2294, 2015 (Year: 2015).*

Csaki et al., Genes involved in the copper-dependent regulation of soluble methane monooxygenase of *Methyloccus capsulatus* (Bath): cloning, sequencing and mutational analysis, *Microbiology*, 149:1785-1795 (2003).

Janssen et al., Cloning of 1,2-Dichloroethene Degradation Genes of *Xanthobacter autrophicus* GJ10 and Expression and Sequencing of the dhlA Gene, *Journal of Bacteriology*, 171(12): 6791-6799 (1989).

Liu et al., Reaction Mechanism of Fluoroacetate Dehalogenase from *Moraxella* sp. B, *The Journal of Biological Chemistry*, 273(47):30897-30902 (1998).

Peterson et al., Putidaredoxin Reductase and Putidaredoxin, *The Journal of Biological Chemistry*, 265(11): 6068-6073 (1990).

Van Der Ploeg et al., Characterization of the Haloacid Dehalogenase from *Xanthobacter autrophicus* GJ10 and Sequencing of the dhlB Gene, *Journal of Bacteriology*, 173(24): 7925-7933 (1991).

European Patent Office, Extended European Search Report for Application No. 16169537.4, dated Feb. 13, 2017, 14 pp.

European Patent Office, Extended European Search Report for Application No. 16202662.9, dated Mar. 22, 2017, 11 pp.

Jahng et al., "Trichloroethylene and Chloroform Degradation by a Recombinant Pseudomonad Expressing Soluble Methane Monooxygenase from *Methylosinus trichosporim* OB3b," *Applied and Environmental Microbiology*, vol. 60, No. 7, pp. 2473-2482 (1994).

Castro et al., "Biodehalogenation: Reactions of Cytochrome P-450 with Polyhalomethanes," *American Chemical Society*, vol. 24, No. 1, pp. 204-210 (1985).

Penny et al., "Microbial degradation of tetrachloromethane: mechanisms and perspectives for bioremediation," *FEMS Microbiology Ecology*, 74, pp. 257-275 (2010).

Luke et al., "Theoretical Investigation of the Anaerobic Reduction of Halogenated Alkanes by Cytochrome P-450. 2. Vertical Electron Affinities of Chlorofluoromethanes as a Measure of Their Activity," *J. Am. Chem. Soc*, 110, pp. 3396-3400 (1988).

West et al., "Functional expression in *Escherichia coli* of proteins B and C from soluble methane monooxygenase of *Methylococcus capsulantus* (Bath)," *Journal of General Microbiology*, vol. 138, pp. 1301-1307 (1992).

Wackett et al., "Metabolism of polyhalogenated compounds by a genetically engineered bacterium," *Nature*, vol. 368 (1994).

Janssen et al., "Cloning of 1,2-Dichloroethane Degradation Genes of *Xanthobacter autotrophicus* GJ10 and Expression and Sequencing of the dhlA Gene," *Journal of Bacteriology*, vol. 171, No. 12, pp. 6791-6799 (1989).

Jan Van Der Ploeg et al., "Characterization of Haloacid Dehalogenase from *Xanthobacter autotrophicus* GJ10 and Sequencing of the dhlB Gene," *Journal of Bacteriology*, vol. 173, No. 34, pp. 7925-7933(1991).

Liu et al., "Reaction Mechanism of Fluoroacetate Dehalogenase from *Moraxella* sp. B", *Journal of Biological Chemistry*, vol. 273, No. 47, pp. 30897-30902 (1998).

Bernardes et al. "Energetics of C—F, C—Cl, C—BR, and C—I Bonds in 2-Haloethanols. Enthalpies of Formation of $XCH_2CH_2OH$ (X=F, Cl, Br, I) Compounds and of the 2-Hydroxyethl Radical," *J. Phys. Chem A*, 111, pp. 1713-1720 (2007).

Schanstra et al. "Specificity and Kinetics of Haloalkane Dehalogenase," *The Journal of Biological Chemistry*, vol. 271, No. 25, pp. 14747-14753 (1996).

Borodina et al., "Mutagenesis of the 'Leucine Gate' to explore the basis of catalytic versatility in soluble methane monooxygenase," *Applied and Environmental Microbiology*, vol. 73, No. 20 pp. 6460-6467 (2007).

Kurihara et al., "Purification, characterization, and gene cloning of a novel fluoroacetate dehalogenase from *Burkholderia* sp. FA1", *Journal of Molecular Catalysis B: Enzymatic* 23, pp. 347-355 (2003).

Kmunicek et al, "Comparative Binding Energy Analysis of the Bubstrate Specificity of Haloalkane Dehalogenase from *Xanthobacter autotrophicus* GJ10," *Biochemistry*, 40, pp. 8905-8917 (2001).

Harkey et al., "Defuorination of 4-fluorophenol by cytochrome $P450_{BM3}$ F87G: activation by long chain fatty aldehydes," *Biotechnol Lett*, 34 (9), pp. 1725-1731 (2012).

Chen, Mike Ming Yu, "Directed Evolution of Cytochrom P45 for Small Alkane Hydroxylation", Thesis, pp. 1-266California Institute of Technology (2011).

Brühlmann et al., Engineering cytochrome P450 BM3 of *Bacillus megaterium* for terminal oxidation of palmitic acid, *Journal of Biotechnology*, 184, pp. 17-26 (2014).

Manchester et al, "Enzyme-catalyzed dehalogenation of pentachloroethane: why F87W-cytochrom P450cam is faster than wild type," *Protein Engineering*, vol. 8, No. 8, pp. 801-807 (1995).

Smith et al., "Improved System for Protein Engineering of the Hydroxylase Component of Soluble Methane Monooxygenase," *Applied and Environmental Microbiology*, vol. 68, No. 11, pp. 5265-5273 (2002).

Keuning et al., "Purification and Characterization of Hydrolytic Haloalkane Dehalogenase from *Xanthobacter autotrophicus* GJ10," *Journal of Bacteriology*, vol. 163, No. 2, pp. 635-639 (1985).

Yasukochi et al., "Putative functions of phenylalanine-350 of *Pseudomonas putida* cytochrome $P-450_{cam}$," *Biochimica et Biophysica Acta*, 1204, pp. 84-90 (1994).

Li et al, "Reductive Dehalogenation by Cytochrome $P450_{CAM}$: Substrate Binding and Catalysis," *Biochemistry*, 32, pp. 9355-9361 (1993).

European Office Action issued in 16 169 537.4 dated Jul. 26, 2018 (5 pages).

Beauvais L.G. et al. "Reactions of the diiron(IV) intermediate Q in soluble methane monooxgenase with fluoromethanes", *Biochemical and Biophysical Research Communications*, Elsevier, Amssterdam, NL, vol. 338, No. 1, pp. 262-266 (2005).

Hyman et al. "Oxidation of Methyl Fluoride and Dimethyl Ether by Ammonia Monooxygenase in *Nitrosomonas europaea*", *Applied and Environmental Microbiology*, pp. 3033-3035 (1994).

Harford-Cross et al., "Protein engineering of cytochrome $P450_{cam}$ (CYP101) for the oxidation of polycyclic aromatic hydrocarbons," *Protein Engineering*, vol. 13, No. 2, pp. 121-128 (2000).

* cited by examiner

SEQUENCE LISTING

```
<160> NUMBER OF SEQ ID NOS: 61

<210> SEQ ID NO 1
<211> LENGTH: 311
<212> TYPE: PRT
<213> ORGANISM: Xanthobacter autotrophicus

<400> SEQUENCE: 1

Met Ile Asn Ala Ile Arg Thr Pro Asp Gln Arg Phe Ser Asn Leu Asp
1               5                   10                  15

Gln Tyr Pro Phe Ser Pro Asn Tyr Leu Asp Asp Leu Pro Gly Tyr Pro
            20                  25                  30

Gly Leu Arg Ala His Tyr Leu Asp Glu Gly Asn Ser Asp Ala Glu Asp
        35                  40                  45

Val Phe Leu Cys Leu His Gly Glu Pro Thr Trp Ser Tyr Leu Tyr Arg
    50                  55                  60

Lys Met Ile Pro Val Phe Ala Glu Ser Gly Ala Arg Val Ile Ala Pro
65                  70                  75                  80

Asp Phe Phe Gly Phe Gly Lys Ser Asp Lys Pro Val Asp Glu Glu Asp
                85                  90                  95

Tyr Thr Phe Glu Phe His Arg Asn Phe Leu Leu Ala Leu Ile Glu Arg
            100                 105                 110

Leu Asp Leu Arg Asn Ile Thr Leu Val Val Gln Asp Trp Gly Gly Phe
        115                 120                 125

Leu Gly Leu Thr Leu Pro Met Ala Asp Pro Ser Arg Phe Lys Arg Leu
    130                 135                 140
```

-continued

Ile Ile Met Asn Ala Cys Leu Met Thr Asp Pro Val Thr Gln Pro Ala
145                 150                 155                 160

Phe Ser Ala Phe Val Thr Gln Pro Ala Asp Gly Phe Thr Ala Trp Lys
                165                 170                 175

Tyr Asp Leu Val Thr Pro Ser Asp Leu Arg Leu Asp Gln Phe Met Lys
            180                 185                 190

Arg Trp Ala Pro Thr Leu Thr Glu Ala Glu Ala Ser Ala Tyr Ala Ala
        195                 200                 205

Pro Phe Pro Asp Thr Ser Tyr Gln Ala Gly Val Arg Lys Phe Pro Lys
    210                 215                 220

Met Val Ala Gln Arg Asp Gln Ala Cys Ile Asp Ile Ser Thr Glu Ala
225                 230                 235                 240

Ile Ser Phe Trp Gln Asn Asp Trp Asn Gly Gln Thr Phe Met Ala Ile
                245                 250                 255

Gly Met Lys Asp Lys Leu Leu Gly Pro Asp Val Met Tyr Pro Met Lys
            260                 265                 270

Ala Leu Ile Asn Gly Cys Pro Glu Pro Leu Glu Ile Ala Asp Ala Gly
        275                 280                 285

His Phe Val Gln Glu Phe Gly Glu Gln Val Ala Arg Glu Ala Leu Lys
    290                 295                 300

His Phe Ala Glu Thr Glu Glx
305                 310

<210> SEQ ID NO 2
<211> LENGTH: 254
<212> TYPE: PRT
<213> ORGANISM: Xanthobacter autotrophicus

<400> SEQUENCE: 2

Met Ile Lys Ala Val Val Phe Asp Ala Tyr Gly Thr Leu Phe Asp Val
1               5                   10                  15

Gln Ser Val Ala Asp Ala Thr Glu Arg Ala Tyr Pro Gly Arg Gly Glu
                20                  25                  30

Tyr Ile Thr Gln Val Trp Arg Gln Lys Gln Leu Glu Tyr Ser Trp Leu
            35                  40                  45

Arg Ala Leu Met Gly Arg Tyr Ala Asp Phe Trp Gly Val Thr Arg Glu
        50                  55                  60

Ala Leu Ala Tyr Thr Leu Gly Thr Leu Gly Leu Glu Pro Asp Glu Ser
65                  70                  75                  80

Phe Leu Ala Gly Met Ala Gln Ala Tyr Asn Arg Leu Thr Pro Tyr Pro
                85                  90                  95

Asp Ala Ala Gln Cys Leu Ala Glu Leu Ala Pro Leu Lys Arg Ala Ile
            100                 105                 110

Leu Ser Asn Gly Ala Pro Asp Met Leu Gln Ala Leu Val Ala Asn Ala
        115                 120                 125

Gly Leu Thr Asp Ser Phe Asp Ala Val Ile Ser Val Asp Ala Lys Arg
    130                 135                 140

Val Phe Lys Pro His Pro Asp Ser Tyr Ala Leu Val Glu Glu Val Leu
145                 150                 155                 160

Gly Val Thr Pro Ala Glu Val Leu Phe Val Ser Ser Asn Gly Phe Asp
                165                 170                 175

Val Gly Gly Ala Lys Asn Phe Gly Phe Ser Val Ala Arg Val Ala Arg
            180                 185                 190

Leu Ser Gln Glu Ala Leu Ala Arg Glu Leu Val Ser Gly Thr Ile Ala

```
            195                 200                 205
    Pro Leu Thr Met Phe Lys Ala Leu Arg Met Arg Glu Glu Thr Tyr Ala
            210                 215                 220

Glu Ala Pro Asp Phe Val Val Pro Ala Leu Gly Asp Leu Pro Arg Leu
    225                 230                 235                 240

Val Arg Gly Met Ala Gly Ala His Leu Ala Pro Ala Val Glx
                    245                 250
```

<210> SEQ ID NO 3
<211> LENGTH: 933
<212> TYPE: DNA
<213> ORGANISM: Xanthobacter autotrophicus

<400> SEQUENCE: 3

| | | | | | | |
|---|---|---|---|---|---|---|
| atgataaatg | caattcgcac | cccggaccaa | cgcttcagca | atctcgatca | gtatccgttc | 60 |
| agccccaact | acctggacga | cctccccggc | tacccgggat | tgcgggcaca | ctacctcgac | 120 |
| gagggcaatt | ctgacgctga | agacgttttt | ctctgccttc | atggcgagcc | acctggagt | 180 |
| tacctgtatc | gcaagatgat | cccggtattt | gctgaatcag | gcgcacgagt | tattgcgcca | 240 |
| gacttttttg | gattcggaaa | atccgacaag | ccagtagacg | aagaagacta | cacctcgaa | 300 |
| tttcaccgca | acttcctgct | tgcactaatc | gaacggcttg | acttgcgcaa | cattacgctg | 360 |
| gtcgttcagg | actggggcgg | atttttgggg | ctgaccttac | cgatggccga | cccttccgc | 420 |
| ttcaagcgcc | tgatcatcat | gaacgcctgc | ttgatgaccg | acccggtcac | ccagcctgcg | 480 |
| tttagcgcct | ttgtcaccca | gcctgcggat | ggctttaccg | cctggaaata | cgatctggtt | 540 |
| acgccatcag | acctgcgcct | tgaccagttc | atgaagcgtt | gggcgcccac | actgaccgaa | 600 |
| gctgaggcct | ccgcgtatgc | tgcgccttc | cctgacactt | cctatcaggc | tggtgtacgc | 660 |
| aagtttccca | agatggtcgc | gcaacgcgac | caggcctgca | tcgacatttc | aaccgaagcg | 720 |
| atttcgttct | ggcagaacga | ctggaatggc | cagaccttca | tggccattgg | catgaaagac | 780 |
| aaattgctgg | gaccggacgt | catgtatcct | atgaaggcgc | tcattaatgg | ctgcccggaa | 840 |
| cccctcgaaa | tagcggacgc | tggccatttc | gtacaggagt | ttggcgagca | agtggctcgc | 900 |
| gaggccctga | aacactttgc | cgagacagaa | tag | | | 933 |

<210> SEQ ID NO 4
<211> LENGTH: 762
<212> TYPE: DNA
<213> ORGANISM: Xanthobacter autotrophicus

<400> SEQUENCE: 4

| | | | | | | |
|---|---|---|---|---|---|---|
| atgatcaagg | cagtcgtgtt | cgacgcttac | ggtacgctct | tcgacgtcca | gtcggtggcc | 60 |
| gacgccaccg | agcgggcgta | tccaggccgg | ggcgagtaca | tcacgcaggt | ctggcggcag | 120 |
| aagcagctgg | aatacagctg | gctccgcgcg | ctgatggggc | gctatgccga | cttttgggc | 180 |
| gtcacgcggg | aagcgctggc | ctataccctc | ggaacgctgg | gctggagcc | ggacgagtcc | 240 |
| ttcctcgccg | ggatggcgca | ggcctacaac | cgcctcacgc | cctatccgga | cgccgcgcaa | 300 |
| tgcctcgcgg | agctggcgcc | ctcaagcgc | gccatcctct | ccaacggcgc | gcccgacatg | 360 |
| ctgcaggcgc | tcgtggccaa | tgcgggcctg | acggacagct | tcgatgccgt | catcagcgtc | 420 |
| gatgccaagc | gcgtgttcaa | gcctcatccc | gactcctacg | cgctggtgga | ggagtacta | 480 |
| ggcgtgacgc | ccgcggaggt | gctgttcgtg | tcctccaacg | gcttcgacgt | cggcggcgcg | 540 |
| aagaatttcg | gcttcagcgt | cgcccgggtc | gcgcgcctgt | cgcaggaggc | gctggcgcgc | 600 |

```
gaactcgtct cgggtaccat cgcgcccctg accatgttca aggcgctgag gatgcgggaa    660
gaaacctatg cggaggcgcc tgatttcgtg gtgcccgccc ttggcgacct gccgcggctg    720
gttcgcggga tggccggcgc tcatctcgca ccagcggtgt ga                        762
```

<210> SEQ ID NO 5
<211> LENGTH: 527
<212> TYPE: PRT
<213> ORGANISM: Methylococcus capsulatus
<220> FEATURE:
<221> NAME/KEY: MISC_FEATURE
<222> LOCATION: (1)..(527)
<223> OTHER INFORMATION: (Bath)

<400> SEQUENCE: 5

```
Met Ala Leu Ser Thr Ala Thr Lys Ala Ala Thr Asp Ala Leu Ala Ala
1               5                   10                  15

Asn Arg Ala Pro Thr Ser Val Asn Ala Gln Glu Val His Arg Trp Leu
            20                  25                  30

Gln Ser Phe Asn Trp Asp Phe Lys Asn Arg Thr Lys Tyr Ala Thr
        35                  40                  45

Lys Tyr Lys Met Ala Asn Glu Thr Lys Glu Gln Phe Lys Leu Ile Ala
50                  55                  60

Lys Glu Tyr Ala Arg Met Glu Ala Val Lys Asp Glu Arg Gln Phe Gly
65                  70                  75                  80

Ser Leu Gln Asp Ala Leu Thr Arg Leu Asn Ala Gly Val Arg Val His
                85                  90                  95

Pro Lys Trp Asn Glu Thr Met Lys Val Val Ser Asn Phe Leu Glu Val
            100                 105                 110

Gly Glu Tyr Asn Ala Ile Ala Ala Thr Gly Met Leu Trp Asp Ser Ala
        115                 120                 125

Gln Ala Ala Glu Gln Lys Asn Gly Tyr Leu Ala Gln Val Leu Asp Glu
130                 135                 140

Ile Arg His Thr His Gln Cys Ala Tyr Val Asn Tyr Tyr Phe Ala Lys
145                 150                 155                 160

Asn Gly Gln Asp Pro Ala Gly His Asn Asp Ala Arg Arg Thr Arg Thr
                165                 170                 175

Ile Gly Pro Leu Trp Lys Gly Met Lys Arg Val Phe Ser Asp Gly Phe
            180                 185                 190

Ile Ser Gly Asp Ala Val Glu Cys Ser Leu Asn Leu Gln Leu Val Gly
        195                 200                 205

Glu Ala Cys Phe Thr Asn Pro Leu Ile Val Ala Val Thr Glu Trp Ala
210                 215                 220

Ala Ala Asn Gly Asp Glu Ile Thr Pro Thr Val Phe Leu Ser Ile Glu
225                 230                 235                 240

Thr Asp Glu Leu Arg His Met Ala Asn Gly Tyr Gln Thr Val Val Ser
                245                 250                 255

Ile Ala Asn Asp Pro Ala Ser Ala Lys Tyr Leu Asn Thr Asp Leu Asn
            260                 265                 270

Asn Ala Phe Trp Thr Gln Gln Lys Tyr Phe Thr Pro Val Leu Gly Met
        275                 280                 285

Leu Phe Glu Tyr Gly Ser Lys Phe Lys Val Glu Pro Trp Val Lys Thr
290                 295                 300

Trp Asn Arg Trp Val Tyr Glu Asp Trp Gly Gly Ile Trp Ile Gly Arg
305                 310                 315                 320

Leu Gly Lys Tyr Gly Val Glu Ser Pro Arg Ser Leu Lys Asp Ala Lys
```

```
                  325                 330                 335
Gln Asp Ala Tyr Trp Ala His His Asp Leu Tyr Leu Ala Tyr Ala
            340                 345                 350
Leu Trp Pro Thr Gly Phe Phe Arg Leu Ala Leu Pro Asp Gln Glu Glu
            355                 360                 365
Met Glu Trp Phe Glu Ala Asn Tyr Pro Gly Trp Tyr Asp His Tyr Gly
    370                 375                 380
Lys Ile Tyr Glu Glu Trp Arg Ala Arg Gly Cys Glu Asp Pro Ser Ser
385                 390                 395                 400
Gly Phe Ile Pro Leu Met Trp Phe Ile Glu Asn Asn His Pro Ile Tyr
                405                 410                 415
Ile Asp Arg Val Ser Gln Val Pro Phe Cys Pro Ser Leu Ala Lys Gly
            420                 425                 430
Ala Ser Thr Leu Arg Val His Glu Tyr Asn Gly Gln Met His Thr Phe
            435                 440                 445
Ser Asp Gln Trp Gly Glu Arg Met Trp Leu Ala Glu Pro Glu Arg Tyr
    450                 455                 460
Glu Cys Gln Asn Ile Phe Glu Gln Tyr Glu Gly Arg Glu Leu Ser Glu
465                 470                 475                 480
Val Ile Ala Glu Leu His Gly Leu Arg Ser Asp Gly Lys Thr Leu Ile
                485                 490                 495
Ala Gln Pro His Val Arg Gly Asp Lys Leu Trp Thr Leu Asp Asp Ile
            500                 505                 510
Lys Arg Leu Asn Cys Val Phe Lys Asn Pro Val Lys Ala Phe Asn
            515                 520                 525
```

<210> SEQ ID NO 6
<211> LENGTH: 1584
<212> TYPE: DNA
<213> ORGANISM: Methylococcus capsulatus
<220> FEATURE:
<221> NAME/KEY: MISC_FEATURE
<222> LOCATION: (1)..(1584)
<223> OTHER INFORMATION: (Bath)

<400> SEQUENCE: 6

```
atggcactta gcaccgcaac caaggccgcg acggacgcgc tggctgccaa tcgggcaccc      60
accagcgtga atgcacagga agtgcaccgt tggctccaga gcttcaactg ggatttcaag     120
aacaaccgga ccaagtacgc caccaagtac aagatggcga acgagaccaa ggaacagttc     180
aagctgatcg ccaaggaata tgcgcgcatg gaggcagtca aggacgaaag gcagttcggt     240
agcctgcagg atgcgctgac ccgcctcaac gccggtgttc gcgttcatcc gaagtggaac     300
gagaccatga agtggtttc gaacttcctg gaagtgggcg aatacaacgc catcgccgct     360
accgggatgc tgtgggattc cgcccaggcg gcggaacaga gaacggcta tctggcccag     420
gtgttggatg aaatccgcca cacccaccag tgtgcctacg tcaactacta cttcgcgaag     480
aacggccagg acccggccgg tcacaacgat gctcgccgca cccgtaccat cggtccgctg     540
tggaagggca tgaagcgcgt gttttccgac ggcttcattt ccggcgacgc cgtggaatgc     600
tccctcaacc tgcagctggt gggtgaggcc tgcttcacca tccgctgat cgtcgcagtg     660
accgaatggg ctgccgccaa cggcgatgaa atcacccga cggtgttcct gtcgatcgag     720
accgacgaac tgcgccacat ggccaacggt taccagaccg tcgtttccat cgccaacgat     780
ccggcttccg ccaagtatct caacacggac ctgaacaacg ccttctggac ccagcagaag     840
tacttcacgc cggtgttggg catgctgttc gagtatggct ccaagttcaa ggtcgagccg     900
```

```
tgggtcaaga cgtggaaccg ctgggtgtac gaggactggg gcggcatctg gatcggccgt    960
ctgggcaagt acggggtgga gtcgccgcgc agcctcaagg acgccaagca ggacgcttac   1020
tgggctcacc acgacctgta tctgctggct tatgcgctgt ggccgaccgg cttcttccgt   1080
ctggcgctgc cggatcagga agaaatggag tggttcgagg ccaactaccc cggctggtac   1140
gaccactacg gcaagatcta cgaggaatgg cgcgcccgcg gttgcgagga tccgtcctcg   1200
ggcttcatcc cgctgatgtg gttcatcgaa aacaaccatc ccatctacat cgatcgcgtg   1260
tcgcaagtgc cgttctgccc gagcttggcc aagggcgcca gcaccctgcg cgtgcacgag   1320
tacaacggcc agatgcacac cttcagcgac cagtggggcg agcgcatgtg gctggccgag   1380
ccggagcgct acgagtgcca gaacatcttc gaacagtacg aaggacgcga actgtcggaa   1440
gtgatcgccg aactgcacgg gctgcgcagt gatggcaaga ccctgatcgc ccagccgcat   1500
gtccgtggcg acaagctgtg gacgttggac gatatcaaac gcctgaactg cgtcttcaag   1560
aacccggtga aggcattcaa ttga                                         1584
```

<210> SEQ ID NO 7
<211> LENGTH: 389
<212> TYPE: PRT
<213> ORGANISM: Methylococcus capsulatus
<220> FEATURE:
<221> NAME/KEY: MISC_FEATURE
<222> LOCATION: (1)..(389)
<223> OTHER INFORMATION: (Bath)

<400> SEQUENCE: 7

```
Met Ser Met Leu Gly Glu Arg Arg Gly Leu Thr Asp Pro Glu Met
 1               5                  10                  15

Ala Ala Val Ile Leu Lys Ala Leu Pro Glu Ala Pro Leu Asp Gly Asn
                20                  25                  30

Asn Lys Met Gly Tyr Phe Val Thr Pro Arg Trp Lys Arg Leu Thr Glu
            35                  40                  45

Tyr Glu Ala Leu Thr Val Tyr Ala Gln Pro Asn Ala Asp Trp Ile Ala
 50                  55                  60

Gly Gly Leu Asp Trp Gly Asp Trp Thr Gln Lys Phe His Gly Arg
 65                  70                  75                  80

Pro Ser Trp Gly Asn Glu Thr Thr Glu Leu Arg Thr Val Asp Trp Phe
                85                  90                  95

Lys His Arg Asp Pro Leu Arg Arg Trp His Ala Pro Tyr Val Lys Asp
            100                 105                 110

Lys Ala Glu Glu Trp Arg Tyr Thr Asp Arg Phe Leu Gln Gly Tyr Ser
        115                 120                 125

Ala Asp Gly Gln Ile Arg Ala Met Asn Pro Thr Trp Arg Asp Glu Phe
    130                 135                 140

Ile Asn Arg Tyr Trp Gly Ala Phe Leu Phe Asn Glu Tyr Gly Leu Phe
145                 150                 155                 160

Asn Ala His Ser Gln Gly Ala Arg Glu Ala Leu Ser Asp Val Thr Arg
                165                 170                 175

Val Ser Leu Ala Phe Trp Gly Phe Asp Lys Ile Asp Ile Ala Gln Met
            180                 185                 190

Ile Gln Leu Glu Arg Gly Phe Leu Ala Lys Ile Val Pro Gly Phe Asp
        195                 200                 205

Glu Ser Thr Ala Val Pro Lys Ala Glu Trp Thr Asn Gly Glu Val Tyr
    210                 215                 220
```

```
Lys Ser Ala Arg Leu Ala Val Glu Gly Leu Trp Gln Glu Val Phe Asp
225                 230                 235                 240

Trp Asn Glu Ser Ala Phe Ser Val His Ala Val Tyr Asp Ala Leu Phe
            245                 250                 255

Gly Gln Phe Val Arg Arg Glu Phe Phe Gln Arg Leu Ala Pro Arg Phe
        260                 265                 270

Gly Asp Asn Leu Thr Pro Phe Phe Ile Asn Gln Ala Gln Thr Tyr Phe
    275                 280                 285

Gln Ile Ala Lys Gln Gly Val Gln Asp Leu Tyr Tyr Asn Cys Leu Gly
290                 295                 300

Asp Asp Pro Glu Phe Ser Asp Tyr Asn Arg Thr Val Met Arg Asn Trp
305                 310                 315                 320

Thr Gly Lys Trp Leu Glu Pro Thr Ile Ala Ala Leu Arg Asp Phe Met
            325                 330                 335

Gly Leu Phe Ala Lys Leu Pro Ala Gly Thr Thr Asp Lys Glu Glu Ile
        340                 345                 350

Thr Ala Ser Leu Tyr Arg Val Val Asp Asp Trp Ile Glu Asp Tyr Ala
    355                 360                 365

Ser Arg Ile Asp Phe Lys Ala Asp Arg Asp Gln Ile Val Lys Ala Val
370                 375                 380

Leu Ala Gly Leu Lys
385
```

<210> SEQ ID NO 8
<211> LENGTH: 1170
<212> TYPE: DNA
<213> ORGANISM: Methylococcus capsulatus
<220> FEATURE:
<221> NAME/KEY: MISC_FEATURE
<222> LOCATION: (1)..(1170)
<223> OTHER INFORMATION: (Bath)

<400> SEQUENCE: 8

```
atgagcatgt taggagaaag acgccgcggt ctgaccgatc cggaaatggc ggccgtcatt      60
ttgaaggcgc ttcctgaagc tccgctggac ggcaacaaca agatgggtta tttcgtcacc     120
ccccgctgga aacgcttgac ggaatatgaa gccctgaccg tttatgcgca gcccaacgcc     180
gactggatcg ccggcggcct ggactggggc gactggaccc agaaattcca cggcggccgc     240
ccttcctggg caacgagac cacggagctg cgcaccgtcg actggttcaa gcaccgtgac     300
ccgctccgcc gttggcatgc gccgtacgtc aaggacaagg ccgaggaatg cgctacacc     360 gaccgcttcc tgcagggtta ctccgccgac ggtcagatcc gggcgatgaa cccgacctgg     420
cgggacgagt tcatcaaccg gtattgggc gccttcctgt tcaacgaata cggattgttc     480
aacgctcatt cgcagggcgc ccgggaggcg ctgtcgacg taacccgcgt cagcctggct     540
ttctggggct tcgacaagat cgacatcgcc cagatgatcc aactcgaacg gggtttcctc     600
gccaagatcg tacccggttt cgacgagtcc acagcggtgc cgaaggccga atggacgaac     660
ggggaggtct acaagagcgc ccgtctggcc gtggaagggc tgtggcagga ggtgttcgac     720
tggaacgaga gcgctttctc ggtgcacgcc gtctatgacg cgctgttcgg tcagttcgtc     780
cgccgcgagt tctttcagcg gctggctccc cgcttcggcg acaatctgac gccattcttc     840
atcaaccagg cccagacata cttccagatc gccaagcagg gcgtacagga tctgtattac     900
aactgtctgg gtgacgatcc ggagttcagc gattacaacc gtaccgtgat gcgcaactgg     960
accggcaagt ggctggagcc cacgatcgcc gctctgcgcg acttcatggg gctgtttgcg     1020
```

```
aagctgccgg cgggcaccac tgacaaggaa gaaatcaccg cgtccctgta ccgggtggtc    1080
gacgactgga tcgaggacta cgccagcagg atcgacttca aggcggaccg cgatcagatc    1140
gttaaagcgg ttctggcagg attgaaataa                                     1170
```

<210> SEQ ID NO 9
<211> LENGTH: 170
<212> TYPE: PRT
<213> ORGANISM: Methylococcus capsulatus
<220> FEATURE:
<221> NAME/KEY: MISC_FEATURE
<222> LOCATION: (1)..(170)
<223> OTHER INFORMATION: (Bath)

<400> SEQUENCE: 9

```
Met Ala Lys Leu Gly Ile His Ser Asn Asp Thr Arg Asp Ala Trp Val
1               5                   10                  15

Asn Lys Ile Ala Gln Leu Asn Thr Leu Glu Lys Ala Ala Glu Met Leu
            20                  25                  30

Lys Gln Phe Arg Met Asp His Thr Thr Pro Phe Arg Asn Ser Tyr Glu
        35                  40                  45

Leu Asp Asn Asp Tyr Leu Trp Ile Glu Ala Lys Leu Glu Glu Lys Val
    50                  55                  60

Ala Val Leu Lys Ala Arg Ala Phe Asn Glu Val Asp Phe Arg His Lys
65                  70                  75                  80

Thr Ala Phe Gly Glu Asp Ala Lys Ser Val Leu Asp Gly Thr Val Ala
                85                  90                  95

Lys Met Asn Ala Ala Lys Asp Lys Trp Glu Ala Glu Lys Ile His Ile
            100                 105                 110

Gly Phe Arg Gln Ala Tyr Lys Pro Pro Ile Met Pro Val Asn Tyr Phe
        115                 120                 125

Leu Asp Gly Glu Arg Gln Leu Gly Thr Arg Leu Met Glu Leu Arg Asn
    130                 135                 140

Leu Asn Tyr Tyr Asp Thr Pro Leu Glu Glu Leu Arg Lys Gln Arg Gly
145                 150                 155                 160

Val Arg Val Val His Leu Gln Ser Pro His
                165                 170
```

<210> SEQ ID NO 10
<211> LENGTH: 513
<212> TYPE: DNA
<213> ORGANISM: Methylococcus capsulatus
<220> FEATURE:
<221> NAME/KEY: MISC_FEATURE
<222> LOCATION: (1)..(513)
<223> OTHER INFORMATION: (Bath)

<400> SEQUENCE: 10

```
atggcgaaac tgggtataca cagcaacgac acccgcgacg cctgggtgaa caagatcgcg     60
cagctcaaca ccctggaaaa agcggccgag atgctgaagc agttccggat ggaccacacc    120
acgccgttcc gcaacagcta cgaactggac aacgactacc tctggatcga ggccaagctc    180
gaagagaagg tcgccgtcct caaggcacgc gccttcaacg aggtggactt ccgtcataag    240
accgctttcg gcgaggatgc caagtccgtt ctggacggca ccgtcgcgaa gatgaacgcg    300
gccaaggaca gtggaggc gagaagatc catatcggtt tccgccaggc ctacaagccg    360
ccgatcatgc cggtgaacta tttcctggac ggcgagcgtc agttgggac ccggctgatg    420 gaactgcgca acctcaacta ctacgacacg ccgctggaag aactgcgcaa acagcgcggt    480
```
gtgcgggtgg tgcatctgca gtcgccgcac tga                                513

<210> SEQ ID NO 11
<211> LENGTH: 141
<212> TYPE: PRT
<213> ORGANISM: Methylococcus capsulatus
<220> FEATURE:
<221> NAME/KEY: MISC_FEATURE
<222> LOCATION: (1)..(141)
<223> OTHER INFORMATION: (Bath)

<400> SEQUENCE: 11

Met Ser Val Asn Ser Asn Ala Tyr Asp Ala Gly Ile Met Gly Leu Lys
1               5                   10                  15

Gly Lys Asp Phe Ala Asp Gln Phe Phe Ala Asp Glu Asn Gln Val Val
            20                  25                  30

His Glu Ser Asp Thr Val Leu Val Leu Lys Lys Ser Asp Glu Ile
        35                  40                  45

Asn Thr Phe Ile Glu Glu Ile Leu Leu Thr Asp Tyr Lys Lys Asn Val
    50                  55                  60

Asn Pro Thr Val Asn Val Glu Asp Arg Ala Gly Tyr Trp Trp Ile Lys
65                  70                  75                  80

Ala Asn Gly Lys Ile Glu Val Asp Cys Asp Glu Ile Ser Glu Leu Leu
                85                  90                  95

Gly Arg Gln Phe Asn Val Tyr Asp Phe Leu Val Asp Val Ser Ser Thr
            100                 105                 110

Ile Gly Arg Ala Tyr Thr Leu Gly Asn Lys Phe Thr Ile Thr Ser Glu
        115                 120                 125

Leu Met Gly Leu Asp Arg Lys Leu Glu Asp Tyr His Ala
    130                 135                 140

<210> SEQ ID NO 12
<211> LENGTH: 426
<212> TYPE: DNA
<213> ORGANISM: Methylococcus capsulatus
<220> FEATURE:
<221> NAME/KEY: MISC_FEATURE
<222> LOCATION: (1)..(426)
<223> OTHER INFORMATION: (Bath)

<400> SEQUENCE: 12
atgagcgtaa acagcaacgc atacgacgcc ggcatcatgg gcctgaaagg caaggacttc    60
gccgatcagt tctttgccga cgaaaaccaa gtggtccatg aaagcgacac ggtcgttctg   120
gtcctcaaga agtcggacga gatcaatacc tttatcgagg agatccttct gacggactac   180
aagaagaacg tcaatccgac ggtaaacgtg gaagaccgcg cgggttactg gtggatcaag   240
gccaacggca gatcgaggt cgattgcgac gagatttccg agctgttggg gcggcagttc   300
aacgtctacg acttcctcgt cgacgtttcc tccaccatcg gccgggccta taccctgggc   360
aacaagttca ccattaccag tgagctgatg ggcctggacc gcaagctcga agactatcac   420
gcttaa                                                              426

<210> SEQ ID NO 13
<211> LENGTH: 348
<212> TYPE: PRT
<213> ORGANISM: Methylococcus capsulatus
<220> FEATURE:
<221> NAME/KEY: MISC_FEATURE
<222> LOCATION: (1)..(348)
<223> OTHER INFORMATION: (Bath)

<400> SEQUENCE: 13

```
Met Gln Arg Val His Thr Ile Thr Ala Val Thr Glu Asp Gly Glu Ser
1               5                   10                  15

Leu Arg Phe Glu Cys Arg Ser Asp Glu Asp Val Ile Thr Ala Ala Leu
            20                  25                  30

Arg Gln Asn Ile Phe Leu Met Ser Ser Cys Arg Glu Gly Gly Cys Ala
        35                  40                  45

Thr Cys Lys Ala Leu Cys Ser Glu Gly Asp Tyr Asp Leu Lys Gly Cys
50                  55                  60

Ser Val Gln Ala Leu Pro Pro Glu Glu Glu Gly Leu Val Leu
65                  70                  75                  80

Leu Cys Arg Thr Tyr Pro Lys Thr Asp Leu Glu Ile Glu Leu Pro Tyr
                85                  90                  95

Thr His Cys Arg Ile Ser Phe Gly Glu Val Gly Ser Phe Glu Ala Glu
            100                 105                 110

Val Val Gly Leu Asn Trp Val Ser Ser Asn Thr Val Gln Phe Leu Leu
        115                 120                 125

Gln Lys Arg Pro Asp Glu Cys Gly Asn Arg Gly Val Lys Phe Glu Pro
130                 135                 140

Gly Gln Phe Met Asp Leu Thr Ile Pro Gly Thr Asp Val Ser Arg Ser
145                 150                 155                 160

Tyr Ser Pro Ala Asn Leu Pro Asn Pro Glu Gly Arg Leu Glu Phe Leu
                165                 170                 175

Ile Arg Val Leu Pro Glu Gly Arg Phe Ser Asp Tyr Leu Arg Asn Asp
            180                 185                 190

Ala Arg Val Gly Gln Val Leu Ser Val Lys Gly Pro Leu Gly Val Phe
        195                 200                 205

Gly Leu Lys Glu Arg Gly Met Ala Pro Arg Tyr Phe Val Ala Gly Gly
210                 215                 220

Thr Gly Leu Ala Pro Val Val Ser Met Val Arg Gln Met Gln Glu Trp
225                 230                 235                 240

Thr Ala Pro Asn Glu Thr Arg Ile Tyr Phe Gly Val Asn Thr Glu Pro
                245                 250                 255

Glu Leu Phe Tyr Ile Asp Glu Leu Lys Ser Leu Glu Arg Ser Met Arg
            260                 265                 270

Asn Leu Thr Val Lys Ala Cys Val Trp His Pro Ser Gly Asp Trp Glu
        275                 280                 285

Gly Glu Gln Gly Ser Pro Ile Asp Ala Leu Arg Glu Asp Leu Glu Ser
290                 295                 300

Ser Asp Ala Asn Pro Asp Ile Tyr Leu Cys Gly Pro Pro Gly Met Ile
305                 310                 315                 320

Asp Ala Ala Cys Glu Leu Val Arg Ser Arg Gly Ile Pro Gly Glu Gln
                325                 330                 335

Val Phe Phe Glu Lys Phe Leu Pro Ser Gly Ala Ala
            340                 345
```

<210> SEQ ID NO 14
<211> LENGTH: 1047
<212> TYPE: DNA
<213> ORGANISM: Methylococcus capsulatus
<220> FEATURE:
<221> NAME/KEY: MISC_FEATURE
<222> LOCATION: (1)..(1047)
<223> OTHER INFORMATION: (Bath)

<400> SEQUENCE: 14

```
atgcagcgag ttcacactat cacggcggtg acggaggatg gcgaatcgct ccgcttcgaa      60
tgccgttcgg acgaggacgt catcaccgcc gccctgcgcc agaacatctt tctgatgtcg     120
tcctgccggg agggcggctg tgcgacctgc aaggccttgt gcagcgaagg ggactacgac     180
ctcaagggct gcagcgttca ggcgctgccg ccggaagagg aggaggaagg gttggtgttg     240
ttgtgccgga cctacccgaa gaccgacctg gaaatcgaac tgccctatac ccattgccgc     300
atcagttttg gtgaggtcgg cagtttcgag gcggaggtcg tcggcctcaa ctgggtttcg     360
agcaacaccg tccagtttct tttgcagaag cggcccgacg agtgcggcaa ccgtggcgtg     420
aaattcgaac ccgtcagtt catggacctg accatcccccg gcaccgatgt ctcccgctcc     480
tactcgccgg cgaaccttcc taatcccgaa ggccgcctgg agttcctgat ccgcgtgtta     540
ccggagggac ggttttcgga ctacctgcgc aatgacgcgc gtgtcggaca ggtcctctcg     600
gtcaaagggc cactgggcgt gttcggtctc aaggagcggg gcatggcgcc gcgctatttc     660
gtggccggcg gcaccgggtt ggcgccggtg gtctcgatgg tgcggcagat gcaggagtgg     720
accgcgccga acgagacccg catctatttc ggtgtgaaca ccgagccgga attgttctac     780
atcgacgagc tcaaatccct ggaacgatcg atgcgcaatc tcaccgtgaa ggcctgtgtc     840
tggcacccga gcggggactg ggaaggcgag cagggctcgc ccatcgatgc gttgcgggaa     900
gacctggagt cctccgacgc caacccggac atttatttgt gcggtccgcc gggcatgatc     960
gatgccgcct gcgagctggt acgcagccgc ggtatccccg gcgaacaggt cttcttcgaa    1020
aaattcctgc cgtccggggc ggcctaa                                         1047
```

<210> SEQ ID NO 15
<211> LENGTH: 103
<212> TYPE: PRT
<213> ORGANISM: Methylococcus capsulatus
<220> FEATURE:
<221> NAME/KEY: MISC_FEATURE
<222> LOCATION: (1)..(103)
<223> OTHER INFORMATION: (Bath)

<400> SEQUENCE: 15

```
Met Val Glu Ser Ala Phe Gln Pro Phe Ser Gly Asp Ala Asp Glu Trp
1               5                   10                  15

Phe Glu Glu Pro Arg Pro Gln Ala Gly Phe Phe Pro Ser Ala Asp Trp
            20                  25                  30

His Leu Leu Lys Arg Asp Glu Thr Tyr Ala Ala Tyr Ala Lys Asp Leu
        35                  40                  45

Asp Phe Met Trp Arg Trp Val Ile Val Arg Glu Glu Arg Ile Val Gln
    50                  55                  60

Glu Gly Cys Ser Ile Ser Leu Glu Ser Ser Ile Arg Ala Val Thr His
65                  70                  75                  80

Val Leu Asn Tyr Phe Gly Met Thr Glu Gln Arg Ala Pro Ala Glu Asp
                85                  90                  95

Arg Thr Gly Gly Val Gln His
            100
```

<210> SEQ ID NO 16
<211> LENGTH: 312
<212> TYPE: DNA
<213> ORGANISM: Methylococcus capsulatus
<220> FEATURE:
<221> NAME/KEY: MISC_FEATURE
<222> LOCATION: (1)..(312)
<223> OTHER INFORMATION: (Bath)

-continued

<400> SEQUENCE: 16

```
atggtcgaat cggcatttca gccattttcg ggcgacgcag acgaatggtt cgaggaacca    60
cggccccagg ccggtttctt cccttccgcg gactggcatc tgctcaaacg ggacgagacc   120
tacgcagcct atgccaagga tctcgatttc atgtggcggt gggtcatcgt ccgggaagaa   180
aggatcgtcc aggagggttg ctcgatcagc ctggagtcgt cgatccgcgc cgtgacgcac   240
gtactgaatt attttggtat gaccgaacaa cgcgccccgg cagaggaccg gaccggcgga   300
gttcaacatt ga                                                      312
```

<210> SEQ ID NO 17
<211> LENGTH: 559
<212> TYPE: PRT
<213> ORGANISM: Methylococcus capsulatus
<220> FEATURE:
<221> NAME/KEY: MISC_FEATURE
<222> LOCATION: (1)..(559)
<223> OTHER INFORMATION: (Bath)

<400> SEQUENCE: 17

Met Ala Lys Glu Val Val Tyr Arg Gly Ser Ala Arg Gln Arg Met Met
1               5                   10                  15

Gln Gly Ile Glu Ile Leu Ala Arg Ala Ala Ile Pro Thr Leu Gly Ala
            20                  25                  30

Thr Gly Pro Ser Val Met Ile Gln His Arg Ala Asp Gly Leu Pro Pro
        35                  40                  45

Ile Ser Thr Arg Asp Gly Val Thr Val Ala Asn Ser Ile Val Leu Lys
    50                  55                  60

Asp Arg Val Ala Asn Leu Gly Ala Arg Leu Leu Arg Asp Val Ala Gly
65                  70                  75                  80

Thr Met Ser Arg Glu Ala Gly Asp Gly Thr Thr Ala Ile Val Leu
                85                  90                  95

Ala Arg His Ile Ala Arg Glu Met Phe Lys Ser Leu Ala Val Gly Ala
            100                 105                 110

Asp Pro Ile Ala Leu Lys Arg Gly Ile Asp Arg Ala Val Ala Arg Val
        115                 120                 125

Ser Glu Asp Ile Gly Ala Arg Ala Trp Arg Gly Asp Lys Glu Ser Val
    130                 135                 140

Ile Leu Gly Val Ala Ala Val Ala Thr Lys Gly Glu Pro Gly Val Gly
145                 150                 155                 160

Arg Leu Leu Leu Glu Ala Leu Asp Ala Val Gly Val His Gly Ala Val
                165                 170                 175

Ser Ile Glu Leu Gly Gln Arg Arg Glu Asp Leu Leu Asp Val Val Asp
            180                 185                 190

Gly Tyr Arg Trp Glu Lys Gly Tyr Leu Ser Pro Tyr Phe Val Thr Asp
        195                 200                 205

Arg Ala Arg Glu Leu Ala Glu Leu Glu Asp Val Tyr Leu Leu Met Thr
    210                 215                 220

Asp Arg Glu Val Val Asp Phe Ile Asp Leu Val Pro Leu Leu Glu Ala
225                 230                 235                 240

Val Thr Glu Ala Gly Gly Ser Leu Leu Ile Ala Ala Asp Arg Val His
                245                 250                 255

Glu Lys Ala Leu Ala Gly Leu Leu Leu Asn His Val Arg Gly Val Phe
            260                 265                 270

Lys Ala Val Ala Val Thr Ala Pro Gly Phe Gly Asp Lys Arg Pro Asn

Arg Leu Leu Asp Leu Ala Ala Leu Thr Gly Gly Arg Ala Val Leu Glu
    275             280             285
290             295             300

Ala Gln Gly Asp Arg Leu Asp Arg Val Thr Leu Ala Asp Leu Gly Arg
305             310             315             320

Val Arg Arg Ala Val Ser Ala Asp Thr Ala Leu Leu Gly Ile
                325             330             335

Pro Gly Thr Glu Ala Ser Arg Ala Arg Leu Glu Gly Leu Arg Leu Glu
            340             345             350

Ala Glu Gln Tyr Arg Ala Leu Lys Pro Gly Gln Gly Ser Ala Thr Gly
            355             360             365

Arg Leu His Glu Leu Glu Ile Glu Ala Arg Ile Val Gly Leu Ser
    370             375             380

Gly Lys Ser Ala Val Tyr Arg Val Gly Gly Val Thr Asp Val Glu Met
385             390             395             400

Lys Glu Arg Met Val Arg Ile Glu Asn Ala Tyr Arg Ser Val Ser
                405             410             415

Ala Leu Glu Glu Gly Val Leu Pro Gly Gly Val Gly Phe Leu Gly
            420             425             430

Ser Met Pro Val Leu Ala Glu Leu Glu Ala Arg Asp Ala Asp Glu Ala
    435             440             445

Arg Gly Ile Gly Ile Val Arg Ser Ala Leu Thr Glu Pro Leu Arg Ile
450             455             460

Ile Gly Glu Asn Ser Gly Leu Ser Gly Glu Ala Val Val Ala Lys Val
465             470             475             480

Met Asp His Ala Asn Pro Gly Trp Gly Tyr Asp Gln Glu Ser Gly Ser
                485             490             495

Phe Cys Asp Leu His Ala Arg Gly Ile Trp Asp Ala Ala Lys Val Leu
            500             505             510

Arg Leu Ala Leu Glu Lys Ala Ala Ser Val Ala Gly Thr Phe Leu Thr
            515             520             525

Thr Glu Ala Val Val Leu Glu Ile Pro Asp Thr Asp Ala Phe Ala Gly
    530             535             540

Phe Ser Ala Glu Trp Ala Ala Ala Thr Arg Glu Asp Pro Arg Val
545             550             555

<210> SEQ ID NO 18
<211> LENGTH: 1680
<212> TYPE: DNA
<213> ORGANISM: Methylococcus capsulatus
<220> FEATURE:
<221> NAME/KEY: MISC_FEATURE
<222> LOCATION: (1)..(1680)
<223> OTHER INFORMATION: (Bath)

<400> SEQUENCE: 18
atggcaaagg aagtggttta caggggagt gcgcggcagc gcatgatgca aggcatcgag     60
atactcgcgc gggcggcgat accgacgctg ggagccaccg gcccagcgt catgatccag    120 caccgcgccg atggcctgcc ccccatttcg acgcgggacg cgtcacggt ggctaactcc    180 atcgtactca aggaccgtgt cgcgaatctc ggtgccggc tgctgcggga cgtcgccggc    240
accatgtccc gcgaagcagg ggatggcacc accaccgcca tcgtgctggc ccgccatatc    300
gcccgggaga tgttcaagag cctcgccgtc ggtgccgatc ccatcgctct caagcgtggt    360
atcgaccgtg ccgtcgcccg cgtgagcgag gacatcgggg ctcgggcctg gcgcggcgac    420

```
aaggaatcgg tcatcctggg ggtggccgcg gtggcgacca agggcgagcc gggcgtgggc      480
cggctgctgc tggaggcgct ggacgcggtc ggcgtccatg gcgccgtgtc gatcgaactg      540
gggcagcggc gcgaggacct gctcgacgtg gtcgacgggt atcgttggga aaaaggttat     600
ctgtcgccct attttgtgac cgatcgggct cgcgagctgg ccgaactcga agacgtctac      660
ctcttgatga ccgatcggga ggtggtcgat ttcatcgatt tggtacccct gctggaggcg      720
gtgaccgagg ctggtggcag cctcctgatc gccgccgacc gtgtccacga gaaggcactg      780
gccggccttt tgctcaatca cgttcgcggc gtcttcaagg ccgtcgcggt caccgcgccc      840
gggttcggcg acaagcggcc gaaccgcctt ttggatctgg cggcgttgac cggtgggcgg      900
gcggtcctgg aagcccaggg cgaccgattg gacccgggtca cgctggccga cctggggcgg      960
gtgcggcggg cggtcgtcag cgctgacgac accgcgctgc tcggcatacc gggcaccgaa     1020
gcctcccggg cccgcttgga gggtttgcgc ctggaagcgg agcagtaccg ggcgctcaag     1080
cccggtcagg gatcggcgac ggggcgcttg cacgagctcg aggaaatcga ggcccggatc     1140
gtcggtctga gcggcaagtc cgcggtctac cgcgtgggcg gcgtgaccga cgtggagatg     1200
aaggagcgga tggtacggat cgaaaatgcc taccgctcgg tggtgtctgc actggaggag     1260
ggggtgttgc ccggcggcgg tgtcgggttt ctgggcagca tgcccgtttt ggccgagctg     1320
gaagcgcgcg atgccgacga agcacgcggc atcggcatcg tccgttccgc gctgacggag     1380
cccctccgga tcatcggaga aaattcggga ctgtcagggg aggccgtcgt cgccaaggtc     1440
atggatcacg ccaatcccgg ttggggttac gatcaggaaa gcggaagttt ctgcgacctc     1500
cacgccaggg gcatttggga tgccgccaag gtgctcaggc tggccctgga aaaagccgcg     1560
tcggtggccg gcacgtttct caccaccgaa gccgtggtac tggagattcc ggacactgac     1620
gctttcgccg gttcagtgc ggagtgggcc gccgcgaccc gggaggatcc gcgggtctaa      1680
```

<210> SEQ ID NO 19
<211> LENGTH: 36
<212> TYPE: DNA
<213> ORGANISM: Artificial Sequence
<220> FEATURE:
<223> OTHER INFORMATION: primer

<400> SEQUENCE: 19

```
aagaaggaga tataccatgg cacttagcac cgcaac                                36
```

<210> SEQ ID NO 20
<211> LENGTH: 40
<212> TYPE: DNA
<213> ORGANISM: Artificial Sequence
<220> FEATURE:
<223> OTHER INFORMATION: primer

<400> SEQUENCE: 20

```
gtggtggtgg tggtgctcga ttaggccgcc ccggacggca                            40
```

<210> SEQ ID NO 21
<211> LENGTH: 36
<212> TYPE: DNA
<213> ORGANISM: Artificial Sequence
<220> FEATURE:
<223> OTHER INFORMATION: primer

<400> SEQUENCE: 21

```
aagaaggaga tataccatgg cacttagcac cgcaac                                36
```

```
<210> SEQ ID NO 22
<211> LENGTH: 39
<212> TYPE: DNA
<213> ORGANISM: Artificial Sequence
<220> FEATURE:
<223> OTHER INFORMATION: primer

<400> SEQUENCE: 22
gaattctgtt tcctgtgtga ttaattgaat gccttcacc                              39

<210> SEQ ID NO 23
<211> LENGTH: 39
<212> TYPE: DNA
<213> ORGANISM: Artificial Sequence
<220> FEATURE:
<223> OTHER INFORMATION: primer

<400> SEQUENCE: 23
tcacacagga aacagaattc atgagcatgt taggagaaa                              39

<210> SEQ ID NO 24
<211> LENGTH: 38
<212> TYPE: DNA
<213> ORGANISM: Artificial Sequence
<220> FEATURE:
<223> OTHER INFORMATION: primer

<400> SEQUENCE: 24
cattatgcgg ccgcaagctt tatttcaatc ctgccaga                               38

<210> SEQ ID NO 25
<211> LENGTH: 36
<212> TYPE: DNA
<213> ORGANISM: Artificial Sequence
<220> FEATURE:
<223> OTHER INFORMATION: primer

<400> SEQUENCE: 25
aagaaggaga tatacatatg gcgaaactgg gtatac                                 36

<210> SEQ ID NO 26
<211> LENGTH: 39
<212> TYPE: DNA
<213> ORGANISM: Artificial Sequence
<220> FEATURE:
<223> OTHER INFORMATION: primer

<400> SEQUENCE: 26
gaattctgtt tcctgtgtga ttagtgcggc gactgcaga                              39

<210> SEQ ID NO 27
<211> LENGTH: 39
<212> TYPE: DNA
<213> ORGANISM: Artificial Sequence
<220> FEATURE:
<223> OTHER INFORMATION: primer

<400> SEQUENCE: 27
tcacacagga aacagaattc atggtcgaat cggcatttc                              39

<210> SEQ ID NO 28
<211> LENGTH: 40
<212> TYPE: DNA
<213> ORGANISM: Artificial Sequence
<220> FEATURE:
<223> OTHER INFORMATION: primer
```

<400> SEQUENCE: 28
gtttctttac cagactcgat taatgttgaa ctccgccggt        40

<210> SEQ ID NO 29
<211> LENGTH: 36
<212> TYPE: DNA
<213> ORGANISM: Artificial Sequence
<220> FEATURE:
<223> OTHER INFORMATION: primer

<400> SEQUENCE: 29
aagaaggaga tatacatatg agcgtaaaca gcaacg        36

<210> SEQ ID NO 30
<211> LENGTH: 39
<212> TYPE: DNA
<213> ORGANISM: Artificial Sequence
<220> FEATURE:
<223> OTHER INFORMATION: primer

<400> SEQUENCE: 30
atgtatatct ccttcttata ttaagcgtga tagtcttcg        39

<210> SEQ ID NO 31
<211> LENGTH: 39
<212> TYPE: DNA
<213> ORGANISM: Artificial Sequence
<220> FEATURE:
<223> OTHER INFORMATION: primer

<400> SEQUENCE: 31
tataagaagg agatatacat atgcagcgag ttcacacta        39

<210> SEQ ID NO 32
<211> LENGTH: 39
<212> TYPE: DNA
<213> ORGANISM: Artificial Sequence
<220> FEATURE:
<223> OTHER INFORMATION: primer

<400> SEQUENCE: 32
gatcgcgtgg ccggccgatt taggccgccc cggacggca        39

<210> SEQ ID NO 33
<211> LENGTH: 36
<212> TYPE: DNA
<213> ORGANISM: Artificial Sequence
<220> FEATURE:
<223> OTHER INFORMATION: primer

<400> SEQUENCE: 33
taataaggag atataccatg gcaaaggaag tggttt        36

<210> SEQ ID NO 34
<211> LENGTH: 38
<212> TYPE: DNA
<213> ORGANISM: Artificial Sequence
<220> FEATURE:
<223> OTHER INFORMATION: primer

<400> SEQUENCE: 34
cattatgcgg ccgcaagctt tagacccgcg gatcctcc        38

<210> SEQ ID NO 35
<211> LENGTH: 5324

```
<212> TYPE: DNA
<213> ORGANISM: Methylococcus capsulatus
<220> FEATURE:
<221> NAME/KEY: MISC_FEATURE
<222> LOCATION: (1)..(5324)
<223> OTHER INFORMATION: (Bath)

<400> SEQUENCE: 35
```

| | | | | |
|---|---|---|---|---|
| atggcactta | gcaccgcaac | caaggccgcg | acggacgcgc | tggctgccaa | tcgggcaccc | 60 |
| accagcgtga | atgcacagga | agtgcaccgt | tggctccaga | gcttcaactg | ggatttcaag | 120 |
| aacaaccgga | ccaagtacgc | caccaagtac | aagatggcga | acgagaccaa | ggaacagttc | 180 |
| aagctgatcg | ccaaggaata | tgcgcgcatg | gaggcagtca | aggacgaaag | gcagttcggt | 240 |
| agcctgcagg | atgcgctgac | ccgcctcaac | gccggtgttc | gcgttcatcc | gaagtggaac | 300 |
| gagaccatga | aagtggtttc | gaacttcctg | gaagtgggcg | aatacaacgc | catcgccgct | 360 |
| accgggatgc | tgtgggattc | cgcccaggcg | gcggaacaga | gaacggcta | tctggcccag | 420 |
| gtgttggatg | aaatccgcca | cacccaccag | tgtgcctacg | tcaactacta | cttcgcgaag | 480 |
| aacggccagg | acccggccgg | tcacaacgat | gctcgccgca | cccgtaccat | cggtccgctg | 540 |
| tggaagggca | tgaagcgcgt | gttttccgac | ggcttcattt | ccggcgacgc | cgtggaatgc | 600 |
| tccctcaacc | tgcagctggt | gggtgaggcc | tgcttcacca | atccgctgat | cgtcgcagtg | 660 |
| accgaatggg | ctgccgccaa | cggcgatgaa | atcaccccga | cggtgttcct | gtcgatcgag | 720 |
| accgacgaac | tgcgccacat | ggccaacggt | taccagaccg | tcgtttccat | cgccaacgat | 780 |
| ccggcttccg | ccaagtatct | caacacggac | ctgaacaacg | ccttctggac | ccagcagaag | 840 |
| tacttcacgc | cggtgttggg | catgctgttc | gagtatggct | ccaagttcaa | ggtcgagccg | 900 |
| tgggtcaaga | cgtggaaccg | ctgggtgtac | gaggactggg | gcggcatctg | gatcggccgt | 960 |
| ctgggcaagt | acggggtgga | gtcgccgcgc | agcctcaagg | acgccaagca | ggacgcttac | 1020 |
| tgggctcacc | acgacctgta | tctgctggct | tatgcgctgt | ggccgaccgg | cttcttccgt | 1080 |
| ctggcgctgc | cggatcagga | agaaatggag | tggttcgagg | ccaactaccc | cggctggtac | 1140 |
| gaccactacg | gcaagatcta | cgaggaatgg | cgcgcccgcg | gttgcgagga | tccgtcctcg | 1200 |
| ggcttcatcc | cgctgatgtg | gttcatcgaa | aacaaccatc | ccatctacat | cgatcgcgtg | 1260 |
| tcgcaagtgc | cgttctgccc | gagcttggcc | aagggcgcca | gcaccctgcg | cgtgcacgag | 1320 |
| tacaacggcc | agatgcacac | cttcagcgac | cagtggggcg | agcgcatgtg | gctggccgag | 1380 |
| ccggagcgct | acgagtgcca | gaacatcttc | gaacagtacg | aaggacgcga | actgtcggaa | 1440 |
| gtgatcgccg | aactgcacgg | gctgcgcagt | gatggcaaga | ccctgatcgc | ccagccgcat | 1500 |
| gtccgtggcg | acaagctgtg | gacgttggac | gatatcaaac | gcctgaactg | cgtcttcaag | 1560 |
| aacccggtga | aggcattcaa | ttgaaacggg | tgtcgggctc | cgtcacaggg | cggggcccga | 1620 |
| cgcacgatcg | ttcgatcaac | ctcaaaccaa | aaggaacat | cgatatgagc | atgttaggag | 1680 |
| aaagacgccg | cggtctgacc | gatccggaaa | tggcggccgt | cattttgaag | gcgcttcctg | 1740 |
| aagctccgct | ggacggcaac | aacaagatgg | gttatttcgt | cacccccgc | tggaaacgct | 1800 |
| tgacggaata | tgaagccctg | accgtttatg | cgcagcccaa | cgccgactgg | atcgccggcg | 1860 |
| gcctggactg | gggcgactgg | acccagaaat | tccacgcgg | ccgcccttcc | tggggcaacg | 1920 |
| agaccacgga | gctgcgcacc | gtcgactggt | tcaagcaccg | tgaccgctc | cgccgttggc | 1980 |
| atgcgccgta | cgtcaaggac | aaggccgagg | aatggcgcta | caccgaccgc | ttcctgcagg | 2040 |
| gttactccgc | cgacggtcag | atccgggcga | tgaacccgac | ctggcgggac | gagttcatca | 2100 |

-continued

```
accggtattg gggcgccttc ctgttcaacg aatacggatt gttcaacgct cattcgcagg      2160
gcgcccggga ggcgctgtcg gacgtaaccc gcgtcagcct ggctttctgg ggcttcgaca      2220
agatcgacat cgcccagatg atccaactcg aacggggttt cctcgccaag atcgtacccg      2280
gtttcgacga gtccacagcg gtgccgaagg ccgaatggac gaacggggag gtctacaaga      2340
gcgcccgtct ggccgtggaa gggctgtggc aggaggtgtt cgactggaac gagagcgctt      2400
tctcggtgca cgccgtctat gacgcgctgt tcggtcagtt cgtccgccgc gagttctttc      2460
agcggctggc tccccgcttc ggcgacaatc tgacgccatt cttcatcaac caggcccaga      2520
catacttcca gatcgccaag cagggcgtac aggatctgta ttacaactgt ctgggtgacg      2580
atccggagtt cagcgattac aaccgtaccg tgatgcgcaa ctggaccggc aagtggctgg      2640
agcccacgat cgccgctctg cgcgacttca tggggctgtt tgcgaagctg ccggcgggca      2700
ccactgacaa ggaagaaatc accgcgtccc tgtaccgggt ggtcgacgac tggatcgagg      2760
actacgccag caggatcgac ttcaaggcgg accgcgatca gatcgttaaa gcggttctgg      2820
caggattgaa ataatagagg aactattacg atgagcgtaa acagcaacgc atacgacgcc      2880
ggcatcatgg gcctgaaagg caaggacttc gccgatcagt tctttgccga cgaaaaccaa      2940
gtggtccatg aaagcgacac ggtcgttctg gtcctcaaga agtcggacga gatcaatacc      3000
tttatcgagg agatccttct gacggactac aagaagaacg tcaatccgac ggtaaacgtg      3060
gaagaccgcg cgggttactg gtggatcaag gccaacggca agatcgaggt cgattgcgac      3120
gagatttccg agctgttggg gcggcagttc aacgtctacg acttcctcgt cgacgtttcc      3180
tccaccatcg gccgggccta cccctgggc aacaagttca ccattaccag tgagctgatg      3240
ggcctggacc gcaagctcga agactatcac gcttaaggag aatgacatgg cgaaactggg      3300
tatacacagc aacgacaccc gcgacgcctg ggtgaacaag atcgcgcagc tcaacaccct      3360
ggaaaaagcg gccgagatgc tgaagcagtt ccggatggac cacaccacgc cgttccgcaa      3420
cagctacgaa ctggacaacg actacctctg gatcgaggcc aagctcgaag agaaggtcgc      3480
cgtcctcaag gcacgcgcct tcaacgaggt ggacttccgt cataagaccg ctttcggcga      3540
ggatgccaag tccgttctgg acggcaccgt cgcgaagatg aacgcggcca aggacaagtg      3600
ggaggcggag aagatccata tcggtttccg ccaggcctac aagccgccga tcatgccggt      3660
gaactatttc ctggacggcg agcgtcagtt ggggacccgg ctgatggaac tgcgcaacct      3720
caactactac gacacgccgc tggaagaact gcgcaaacag cgcggtgtgc gggtggtgca      3780
tctgcagtcg ccgcactgaa gggaggaagt ctcgccctgg acgcgacggc atcgccgtga      3840
agtccagggg gcagggatgc cgttccgggc cggcaggctg gcccggaatc tctggttttc      3900
aggggggcgtg ccggtccacg gctcccccct ccatctttcg taaggaaatc accatggtcg      3960
aatcggcatt tcagccattt tcgggcgacg cagacgaatg gttcgaggaa ccacggcccc      4020
aggccggttt cttcccttcc gcggactggc atctgctcaa acgggacgag acctacgcag      4080
cctatgccaa ggatctcgat ttcatgtggc ggtgggtcat cgtccgggaa gaaaggatcg      4140
tccaggaggg ttgctcgatc agcctggagt cgtcgatccg cgccgtgacg cacgtactga      4200
attattttgg tatgaccgaa caacgcgccc cggcagagga ccggaccggc ggagttcaac      4260
attgaacagg taagtttatg cagcgagttc acactatcac ggcggtgacg gaggatggcg      4320
aatcgctccg cttcgaatgc cgttcggacg aggacgtcat caccgccgcc tgcgccagga      4380
acatcttcct gatgtcgtcc tgccggggag gcggctgtgc gacctgcaag gccttgtgca      4440
gcgaagggga ctacgacctc aagggctgca gcgttcaggc gctgccgccg aagaggagg       4500
```

```
aggaagggtt ggtgttgttg tgccggacct acccgaagac cgacctggaa atcgaactgc    4560 cctatacccca ttgccgcatc agttttggtg aggtcggcag tttcgaggcg aggtcgtcg    4620 gcctcaactg ggtttcgagc aacaccgtcc agtttctttt gcagaagcgg cccgacgagt    4680
gcggcaaccg tggcgtgaaa ttcgaacccg gtcagttcat ggacctgacc atccccggca    4740
ccgatgtctc ccgctcctac tcgccggcga accttcctaa tcccgaaggc cgcctggagt    4800
tcctgatccg cgtgttaccg gagggacggt tttcggacta cctgcgcaat gacgcgcgtg    4860
tcggacaggt cctctcggtc aaagggccac tgggcgtgtt cggtctcaag gagcggggca    4920
tggcgccgcg ctatttcgtg gccggcggca ccgggttggc gccggtggtc tcgatggtgc    4980
ggcagatgca ggagtggacc gcgccgaacg agacccgcat ctatttcggt gtgaacaccg    5040
agccggaatt gttctacatc gacgagctca aatccctgga acgatcgatg cgcaatctca    5100
ccgtgaaggc ctgtgtctgg cacccgagcg gggactggga aggcgagcag ggctcgccca    5160
tcgatgcgtt gcgggaagac ctggagtcct ccgacgccaa cccggacatt tatttgtgcg    5220
gtccgccggg catgatcgat gccgcctgcg agctggtacg cagccgcggt atccccggcg    5280
aacaggtctt cttcgaaaaa ttcctgccgt ccggggcggc ctaa                     5324
```

<210> SEQ ID NO 36
<211> LENGTH: 1269
<212> TYPE: DNA
<213> ORGANISM: Pseudomonas putida
<220> FEATURE:
<221> NAME/KEY: MISC_FEATURE
<222> LOCATION: (1)..(1269)
<223> OTHER INFORMATION: PpG786 strain DSM 7162

<400> SEQUENCE: 36

```
atgaacgcaa acgacaacgt ggtcatcgtc ggtaccggac tggctggcgt tgaggtcgcc      60
ttcggcctgc cgccagcgg ctgggaaggc aatatccggt tggtgggggga tgcgacggta    120 attccccatc acctaccacc gctatccaaa gcttacttgg ccggcaaagc cacagcggaa    180
agcctgtacc tgagaacccc agatgccctat gcagcgcaga acatccaact actcggaggc    240
acacaggtaa cggctatcaa ccgcgaccga cagcaagtaa tcctatcgga tggccgggca    300
ctggattacg accggctggt attggctacc ggagggcgtc caagacccct accggtggcc    360
agtggcgcag ttggaaaggc gaacaacttt cgatacctgc gcacactcga ggacgccgag    420
tgcattcgcc ggcagctgat tgcggataac cgtctggtgg tgattggtgg cggctacatt    480
ggccttgaag tggctgccac cgccatcaag gcgaacatgc acgtcaccct gcttgatacg    540
gcagcccggg ttctggagcg ggttaccgcc ccgccggtat cggccttta cgagcaccta    600 caccgcgaag ccggcgttga catacgaacc ggcacgcagg tgtgcgggtt cgagatgtcg    660
accgaccaac agaaggttac tgccgtcctc tgcgaggacg gcacaaggct gccagcggat    720
ctggtaatcg ccgggattgg cctgatacca aactgcgagt tggccagtgc ggccggcctg    780
caggttgata acggcatcgt gatcaacgaa cacatgcaga cctctgatcc cttgatcatg    840
gccgtcggcg actgtgcccg atttcacagt cagctctatg accgctgggt gcgtatcgaa    900
tcggtgccca tgccttgga gcaggcacga agatcgccg ccatcctctg tggcaaggtg      960
ccacgcgatg aggcggcgcc ctggttctgg tccgatcagt atgagatcgg attgaagatg   1020
gtcggactgt ccgaagggta cgaccggatc attgtccgcg gctctttggc gcaacccgac   1080
ttcagcgttt tctacctgca gggagaccgg gtattggcgg tcgatacagt gaaccgtcca   1140
```

```
gtggagttca accagtcaaa acaaataatc acggatcgtt tgccggttga accaaaccta    1200
ctcggtgacg aaagcgtgcc gttaaaggaa atcatcgccg ccgccaaagc tgaactgagt    1260
agtgcctaa                                                            1269
```

<210> SEQ ID NO 37
<211> LENGTH: 422
<212> TYPE: PRT
<213> ORGANISM: Pseudomonas putida
<220> FEATURE:
<221> NAME/KEY: MISC_FEATURE
<222> LOCATION: (1)..(422)
<223> OTHER INFORMATION: PpG786 strain DSM 7162

<400> SEQUENCE: 37

```
Met Asn Ala Asn Asp Asn Val Val Ile Val Gly Thr Gly Leu Ala Gly
1               5                   10                  15

Val Glu Val Ala Phe Gly Leu Arg Ala Ser Gly Trp Glu Gly Asn Ile
            20                  25                  30

Arg Leu Val Gly Asp Ala Thr Val Ile Pro His His Leu Pro Pro Leu
        35                  40                  45

Ser Lys Ala Tyr Leu Ala Gly Lys Ala Thr Ala Glu Ser Leu Tyr Leu
    50                  55                  60

Arg Thr Pro Asp Ala Tyr Ala Ala Gln Asn Ile Gln Leu Leu Gly Gly
65                  70                  75                  80

Thr Gln Val Thr Ala Ile Asn Arg Asp Arg Gln Gln Val Ile Leu Ser
                85                  90                  95

Asp Gly Arg Ala Leu Asp Tyr Asp Arg Leu Val Leu Ala Thr Gly Gly
            100                 105                 110

Arg Pro Arg Pro Leu Pro Val Ala Ser Gly Ala Val Gly Lys Ala Asn
        115                 120                 125

Asn Phe Arg Tyr Leu Arg Thr Leu Glu Asp Ala Glu Cys Ile Arg Arg
    130                 135                 140

Gln Leu Ile Ala Asp Asn Arg Leu Val Val Ile Gly Gly Gly Tyr Ile
145                 150                 155                 160

Gly Leu Glu Val Ala Ala Thr Ala Ile Lys Ala Asn Met His Val Thr
                165                 170                 175

Leu Leu Asp Thr Ala Ala Arg Val Leu Glu Arg Val Thr Ala Pro Pro
            180                 185                 190

Val Ser Ala Phe Tyr Glu His Leu His Arg Glu Ala Gly Val Asp Ile
        195                 200                 205

Arg Thr Gly Thr Gln Val Cys Gly Phe Glu Met Ser Thr Asp Gln Gln
    210                 215                 220

Lys Val Thr Ala Val Leu Cys Glu Asp Gly Thr Arg Leu Pro Ala Asp
225                 230                 235                 240

Leu Val Ile Ala Gly Ile Gly Leu Ile Pro Asn Cys Glu Leu Ala Ser
                245                 250                 255

Ala Ala Gly Leu Gln Val Asp Asn Gly Ile Val Ile Asn Glu His Met
            260                 265                 270

Gln Thr Ser Asp Pro Leu Ile Met Ala Val Gly Asp Cys Ala Arg Phe
        275                 280                 285

His Ser Gln Leu Tyr Asp Arg Trp Val Arg Ile Glu Ser Val Pro Asn
    290                 295                 300

Ala Leu Glu Gln Ala Arg Lys Ile Ala Ala Ile Leu Cys Gly Lys Val
305                 310                 315                 320

Pro Arg Asp Glu Ala Ala Pro Trp Phe Trp Ser Asp Gln Tyr Glu Ile
```

```
              325                 330                 335
Gly Leu Lys Met Val Gly Leu Ser Glu Gly Tyr Asp Arg Ile Ile Val
            340                 345                 350

Arg Gly Ser Leu Ala Gln Pro Asp Phe Ser Val Phe Tyr Leu Gln Gly
        355                 360                 365

Asp Arg Val Leu Ala Val Asp Thr Val Asn Arg Pro Val Glu Phe Asn
    370                 375                 380

Gln Ser Lys Gln Ile Ile Thr Asp Arg Leu Pro Val Glu Pro Asn Leu
385                 390                 395                 400

Leu Gly Asp Glu Ser Val Pro Leu Lys Glu Ile Ile Ala Ala Ala Lys
                405                 410                 415

Ala Glu Leu Ser Ser Ala
            420

<210> SEQ ID NO 38
<211> LENGTH: 324
<212> TYPE: DNA
<213> ORGANISM: Pseudomonas putida
<220> FEATURE:
<221> NAME/KEY: MISC_FEATURE
<222> LOCATION: (1)..(324)
<223> OTHER INFORMATION: PpG786 strain DSM 7162

<400> SEQUENCE: 38
atgtctaaag tagtgtatgt gtcacatgat ggaacgcgtc gcgaactgga tgtggcggat      60
ggcgtcagcc tgatgcaggc tgcagtctcc aatggtatct acgatattgt cggtgattgt     120
ggcggcagcg ccagctgtgc cacctgccat gtctatgtga acgaagcgtt cacggacaag     180
gtgcccgccg ccaacgagcg ggaaatcggc atgctggagt gcgtcacggc cgaactgaag     240
ccgaacagca ggtctctgctg ccagatcatc atgacgcccg agctggatgg catcgtggtc     300
gatgttcccg ataggcaatg gtaa                                              324

<210> SEQ ID NO 39
<211> LENGTH: 107
<212> TYPE: PRT
<213> ORGANISM: Pseudomonas putida
<220> FEATURE:
<221> NAME/KEY: MISC_FEATURE
<222> LOCATION: (1)..(107)
<223> OTHER INFORMATION: PpG786 strain DSM 7162

<400> SEQUENCE: 39

Met Ser Lys Val Val Tyr Val Ser His Asp Gly Thr Arg Arg Glu Leu
1               5                   10                  15

Asp Val Ala Asp Gly Val Ser Leu Met Gln Ala Ala Val Ser Asn Gly
            20                  25                  30

Ile Tyr Asp Ile Val Gly Asp Cys Gly Gly Ser Ala Ser Cys Ala Thr
        35                  40                  45

Cys His Val Tyr Val Asn Glu Ala Phe Thr Asp Lys Val Pro Ala Ala
    50                  55                  60

Asn Glu Arg Glu Ile Gly Met Leu Glu Cys Val Thr Ala Glu Leu Lys
65                  70                  75                  80

Pro Asn Ser Arg Leu Cys Cys Gln Ile Ile Met Thr Pro Glu Leu Asp
                85                  90                  95

Gly Ile Val Val Asp Val Pro Asp Arg Gln Trp
            100                 105

<210> SEQ ID NO 40
```

<211> LENGTH: 1248
<212> TYPE: DNA
<213> ORGANISM: Pseudomonas putida
<220> FEATURE:
<221> NAME/KEY: MISC_FEATURE
<222> LOCATION: (1)..(1248)
<223> OTHER INFORMATION: PpG786 strain DSM 7162

<400> SEQUENCE: 40

```
atgacgactg aaaccataca aagcaacgcc aatcttgccc ctctgccacc ccatgtgcca      60
gagcacctgg tattcgactt cgacatgtac aatccgtcga atctgtctgc cggcgtgcag     120
gaggcctggg cagttctgca agaatcaaac gtaccggatc tggtgtggac tcgctgcaac     180
ggcggacact ggatcgccac tcgcggccaa ctgatccgtg aggcctatga agattaccgc     240
cactttccca gcgagtgccc gttcatccct cgtgaagccg gcgaagccta cgacttcatt     300
cccacctcga tggatccgcc cgagcagcgc cagtttcgtg cgctggccaa ccaagtggtt     360
ggcatgccgg tggtggataa gctggagaac cggatccagg agctggcctg ctcgctgatc     420
gagagcctgc gcccgcaagg acagtgcaac ttcaccgagg actacgccga acccttcccg     480
atacgcatct tcatgctgct cgcaggtcta ccggaagaag atatcccgca cttgaaatac     540
ctaacggatc agatgacccg tccggatggc agcatgacct tcgcagaggc caaggaggcg     600
ctctacgact atctgatacc gatcatcgag caacgcaggc agaagccggg aaccgacgct     660
atcagcatcg ttgccaacgg ccaggtcaat gggcgaccga tcaccagtga cgaagccaag     720
aggatgtgtg gcctgttact ggtcggcggc ctggatacgg tggtcaattt cctcagcttc     780
agcatggagt tcctggccaa aagcccggag catcgccagg agctgatcga cgtcccgag     840
cgtattccag ccgcttgcga ggaactactc cggcgcttct cgctggttgc cgatggccgc     900
atcctcacct ccgattacga gtttcatggc gtgcaactga agaaaggtga ccagatcctg     960
ctaccgcaga tgctgtctgg cctggatgag cgcgaaaacg cctgcccgat gcacgtcgac    1020
ttcagtcgcc aaaaggtttc acacaccacc tttggccacg cagccatct gtgccttggc    1080
cagcacctgg cccgccggga atcatcgtc accctcaagg aatggctgac caggattcct    1140
gacttctcca ttgccccggg tgcccagatt cagcacaaga gcggcatcgt cagcggcgtg    1200
caggcactcc ctctggtctg ggatccggcg actaccaaag cggtataa                1248
```

<210> SEQ ID NO 41
<211> LENGTH: 415
<212> TYPE: PRT
<213> ORGANISM: Pseudomonas putida
<220> FEATURE:
<221> NAME/KEY: MISC_FEATURE
<222> LOCATION: (1)..(415)
<223> OTHER INFORMATION: PpG786 strain DSM 7162

<400> SEQUENCE: 41

```
Met Thr Thr Glu Thr Ile Gln Ser Asn Ala Asn Leu Ala Pro Leu Pro
1               5                   10                  15

Pro His Val Pro Glu His Leu Val Phe Asp Phe Asp Met Tyr Asn Pro
            20                  25                  30

Ser Asn Leu Ser Ala Gly Val Gln Glu Ala Trp Ala Val Leu Gln Glu
        35                  40                  45

Ser Asn Val Pro Asp Leu Val Trp Thr Arg Cys Asn Gly Gly His Trp
    50                  55                  60

Ile Ala Thr Arg Gly Gln Leu Ile Arg Glu Ala Tyr Glu Asp Tyr Arg
65                  70                  75                  80
```

His Phe Ser Ser Glu Cys Pro Phe Ile Pro Arg Glu Ala Gly Glu Ala
                85                  90                  95

Tyr Asp Phe Ile Pro Thr Ser Met Asp Pro Glu Gln Arg Gln Phe
        100                 105                 110

Arg Ala Leu Ala Asn Gln Val Val Gly Met Pro Val Val Asp Lys Leu
            115                 120                 125

Glu Asn Arg Ile Gln Glu Leu Ala Cys Ser Leu Ile Glu Ser Leu Arg
130                 135                 140

Pro Gln Gly Gln Cys Asn Phe Thr Glu Asp Tyr Ala Glu Pro Phe Pro
145                 150                 155                 160

Ile Arg Ile Phe Met Leu Leu Ala Gly Leu Pro Glu Glu Asp Ile Pro
                165                 170                 175

His Leu Lys Tyr Leu Thr Asp Gln Met Thr Arg Pro Asp Gly Ser Met
            180                 185                 190

Thr Phe Ala Glu Ala Lys Glu Ala Leu Tyr Asp Tyr Leu Ile Pro Ile
        195                 200                 205

Ile Glu Gln Arg Arg Gln Lys Pro Gly Thr Asp Ala Ile Ser Ile Val
210                 215                 220

Ala Asn Gly Gln Val Asn Gly Arg Pro Ile Thr Ser Asp Glu Ala Lys
225                 230                 235                 240

Arg Met Cys Gly Leu Leu Leu Val Gly Gly Leu Asp Thr Val Val Asn
                245                 250                 255

Phe Leu Ser Phe Ser Met Glu Phe Leu Ala Lys Ser Pro Glu His Arg
            260                 265                 270

Gln Glu Leu Ile Glu Arg Pro Glu Arg Ile Pro Ala Ala Cys Glu Glu
        275                 280                 285

Leu Leu Arg Arg Phe Ser Leu Val Ala Asp Gly Arg Ile Leu Thr Ser
290                 295                 300

Asp Tyr Glu Phe His Gly Val Gln Leu Lys Lys Gly Asp Gln Ile Leu
305                 310                 315                 320

Leu Pro Gln Met Leu Ser Gly Leu Asp Glu Arg Glu Asn Ala Cys Pro
                325                 330                 335

Met His Val Asp Phe Ser Arg Gln Lys Val Ser His Thr Thr Phe Gly
            340                 345                 350

His Gly Ser His Leu Cys Leu Gly Gln His Leu Ala Arg Arg Glu Ile
        355                 360                 365

Ile Val Thr Leu Lys Glu Trp Leu Thr Arg Ile Pro Asp Phe Ser Ile
370                 375                 380

Ala Pro Gly Ala Gln Ile Gln His Lys Ser Gly Ile Val Ser Gly Val
385                 390                 395                 400

Gln Ala Leu Pro Leu Val Trp Asp Pro Ala Thr Thr Lys Ala Val
                405                 410                 415

<210> SEQ ID NO 42
<211> LENGTH: 3150
<212> TYPE: DNA
<213> ORGANISM: Bacillus megaterium
<220> FEATURE:
<221> NAME/KEY: MISC_FEATURE
<222> LOCATION: (1)..(3150)
<223> OTHER INFORMATION: (ATCC 14581)

<400> SEQUENCE: 42
atgacaatta aagaaatgcc tcagccaaaa acgtttggag agcttaaaaa tttaccgtta      60
ttaaacacag ataaaccggt tcaagctttg atgaaaattg cggatgaatt aggagaaatc     120

```
tttaaattcg aggcgcctgg tcgtgtaacg cgctacttat caagtcagcg tctaattaaa    180
gaagcatgcg atgaatcacg ctttgataaa aacttaagtc aagcgcttaa atttgtacgt    240
gattttgcag gagacgggtt atttacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagctgcag cgagcaaatc cagacgaccc agcttatgat    600
gaaaacaagc gccagtttca agaagatatc aaggtgatga acgacctagt agataaaatt    660
attgcagatc gcaaagcaag cggtgaacaa agcgatgatt tattaacgca tatgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaac taatggttct gattcctcag   1080
cttcaccgtg ataaaacaat ttggggagac gatgtgaaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctggata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg ctttttatcga tgaaacgctt gccgctaaag gggcagaaaa catcgctgac   1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc ccgcgcgata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taagtagag    2340 cttgaagcct tgcttgaaaa gcaagcctac aaagaacaag tgctggcaaa acgtttaaca   2400
atgcttgaac tgcttgaaaa ataccccggcg tgtgaaatga aattcagcga atttatcgcc   2460
cttctgccaa gcatacgccc gcgctattac tcgatttctt catcacctcg tgtcgatgaa   2520
```

-continued

```
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct tgtgcaggc gcgcaaacag     2760 ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg     2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 43
<211> LENGTH: 1049
<212> TYPE: PRT
<213> ORGANISM: Bacillus megaterium
<220> FEATURE:
<221> NAME/KEY: MISC_FEATURE
<222> LOCATION: (1)..(1049)
<223> OTHER INFORMATION: (ATCC 14581)

<400> SEQUENCE: 43

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240
```

```
Gly Lys Asp Pro Glu Thr Gly Glu Pro Leu Asp Asp Glu Asn Ile Arg
            245                 250                 255

Tyr Gln Ile Ile Thr Phe Leu Ile Ala Gly His Glu Thr Thr Ser Gly
        260                 265                 270

Leu Leu Ser Phe Ala Leu Tyr Phe Leu Val Lys Asn Pro His Val Leu
    275                 280                 285

Gln Lys Ala Ala Glu Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655
```

Ala Lys Met His Gly Ala Phe Ser Thr Asn Val Val Ala Ser Lys Glu
        660                 665                 670

Leu Gln Gln Pro Gly Ser Ala Arg Ser Thr Arg His Leu Glu Ile Glu
    675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
        770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
            1045

<210> SEQ ID NO 44
<211> LENGTH: 1476
<212> TYPE: DNA

```
<213> ORGANISM: Escherichia coli
<220> FEATURE:
<221> NAME/KEY: MISC_FEATURE
<222> LOCATION: (1)..(1476)
<223> OTHER INFORMATION: K12 (MG1655)

<400> SEQUENCE: 44
```

| | |
|---|---:|
| atggcggtaa cgcaaacagc ccaggcctgt gacctggtca ttttcggcgc gaaaggcgac | 60 |
| cttgcgcgtc gtaaattgct gccttccctg tatcaactgg aaaaagccgg tcagctcaac | 120 |
| ccggacaccc ggattatcgg cgtagggcgt gctgactggg ataaagcggc ataccaaa | 180 |
| gttgtccgcg aggcgctcga aactttcatg aaagaaacca ttgatgaagg tttatgggac | 240 |
| accctgagtg cacgtctgga ttttgtaat ctcgatgtca atgacactgc tgcattcagc | 300 |
| cgtctcggcg cgatgctgga tcaaaaaaat cgtatcacca ttaactactt tgccatgccg | 360 |
| cccagcactt ttggcgcaat ttgcaaaggg cttggcgagg caaaactgaa tgctaaaccg | 420 |
| gcacgcgtag tcatggagaa accgctgggg acgtcgctgg cgacctcgca ggaaatcaat | 480 |
| gatcaggttg gcgaatactt cgaggagtgc caggtttacc gtatcgacca ctatcttggt | 540 |
| aaagaaacgg tgctgaacct gttggcgctg cgttttgcta actccctgtt tgtgaataac | 600 |
| tgggacaatc gcaccattga tcatgttgag attaccgtgg cagaagaagt ggggatcgaa | 660 |
| gggcgctggg gctatttga taaagccggt cagatgcgcg acatgatcca gaaccacctg | 720 |
| ctgcaaattc tttgcatgat tgcgatgtct ccgccgtctg acctgagcgc agacagcatc | 780 |
| cgcgatgaaa aagtgaaagt actgaagtct ctgcgccgca tcgaccgctc caacgtacgc | 840 |
| gaaaaaaccg tacgcgggca atatactgcg ggcttcgccc agggcaaaaa agtgccggga | 900 |
| tatctggaag aagagggcgc gaacaagagc agcaatacag aaactttcgt ggcgatccgc | 960 |
| gtcgacattg ataactggcg ctgggccggt gtgccattct acctgcgtac tggtaaacgt | 1020 |
| ctgccgacca aatgttctga agtcgtggtc tatttcaaaa cacctgaact gaatctgttt | 1080 |
| aaagaatcgt ggcaggatct gccgcagaat aaactgacta ccgtctgca acctgatgaa | 1140 |
| ggcgtggata tccaggtact gaataaagtt cctggccttg accacaaaca taacctgcaa | 1200 |
| atcaccaagc tggatctgag ctattcagaa acctttaatc agacgcatct ggcggatgcc | 1260 |
| tatgaacgtt tgctgctgga aaccatgcgt ggtattcagg cactgtttgt acgtcgcgac | 1320 |
| gaagtggaag aagcctggaa atgggtagac tccattactg aggcgtgggc gatgacaat | 1380 |
| gatgcgccga accgtatca ggccggaacc tggggacccg ttgcctcggt ggcgatgatt | 1440 |
| acccgtgatg gtcgttcctg gaatgagttt gagtaa | 1476 |

```
<210> SEQ ID NO 45
<211> LENGTH: 491
<212> TYPE: PRT
<213> ORGANISM: Escherichia coli
<220> FEATURE:
<221> NAME/KEY: MISC_FEATURE
<222> LOCATION: (1)..(1476)
<223> OTHER INFORMATION: K12 (MG1655)

<400> SEQUENCE: 45

Met Ala Val Thr Gln Thr Ala Gln Ala Cys Asp Leu Val Ile Phe Gly
1               5                   10                  15

Ala Lys Gly Asp Leu Ala Arg Arg Lys Leu Leu Pro Ser Leu Tyr Gln
                20                  25                  30

Leu Glu Lys Ala Gly Gln Leu Asn Pro Asp Thr Arg Ile Ile Gly Val
        35                  40                  45
```

-continued

```
Gly Arg Ala Asp Trp Asp Lys Ala Ala Tyr Thr Lys Val Val Arg Glu
    50                  55                  60

Ala Leu Glu Thr Phe Met Lys Glu Thr Ile Asp Glu Gly Leu Trp Asp
65                  70                  75                  80

Thr Leu Ser Ala Arg Leu Asp Phe Cys Asn Leu Asp Val Asn Asp Thr
                85                  90                  95

Ala Ala Phe Ser Arg Leu Gly Ala Met Leu Asp Gln Lys Asn Arg Ile
            100                 105                 110

Thr Ile Asn Tyr Phe Ala Met Pro Pro Ser Thr Phe Gly Ala Ile Cys
        115                 120                 125

Lys Gly Leu Gly Glu Ala Lys Leu Asn Ala Lys Pro Ala Arg Val Val
130                 135                 140

Met Glu Lys Pro Leu Gly Thr Ser Leu Ala Thr Ser Gln Glu Ile Asn
145                 150                 155                 160

Asp Gln Val Gly Glu Tyr Phe Glu Glu Cys Gln Val Tyr Arg Ile Asp
                165                 170                 175

His Tyr Leu Gly Lys Glu Thr Val Leu Asn Leu Leu Ala Leu Arg Phe
            180                 185                 190

Ala Asn Ser Leu Phe Val Asn Asn Trp Asp Asn Arg Thr Ile Asp His
        195                 200                 205

Val Glu Ile Thr Val Ala Glu Val Gly Ile Glu Gly Arg Trp Gly
210                 215                 220

Tyr Phe Asp Lys Ala Gly Gln Met Arg Asp Met Ile Gln Asn His Leu
225                 230                 235                 240

Leu Gln Ile Leu Cys Met Ile Ala Met Ser Pro Pro Ser Asp Leu Ser
                245                 250                 255

Ala Asp Ser Ile Arg Asp Glu Lys Val Lys Val Leu Lys Ser Leu Arg
            260                 265                 270

Arg Ile Asp Arg Ser Asn Val Arg Glu Lys Thr Val Arg Gly Gln Tyr
        275                 280                 285

Thr Ala Gly Phe Ala Gln Gly Lys Lys Val Pro Gly Tyr Leu Glu Glu
290                 295                 300

Glu Gly Ala Asn Lys Ser Ser Asn Thr Glu Thr Phe Val Ala Ile Arg
305                 310                 315                 320

Val Asp Ile Asp Asn Trp Arg Trp Ala Gly Val Pro Phe Tyr Leu Arg
                325                 330                 335

Thr Gly Lys Arg Leu Pro Thr Lys Cys Ser Glu Val Val Val Tyr Phe
            340                 345                 350

Lys Thr Pro Glu Leu Asn Leu Phe Lys Glu Ser Trp Gln Asp Leu Pro
        355                 360                 365

Gln Asn Lys Leu Thr Ile Arg Leu Gln Pro Asp Glu Gly Val Asp Ile
370                 375                 380

Gln Val Leu Asn Lys Val Pro Gly Leu Asp His Lys His Asn Leu Gln
385                 390                 395                 400

Ile Thr Lys Leu Asp Leu Ser Tyr Ser Glu Thr Phe Asn Gln Thr His
                405                 410                 415

Leu Ala Asp Ala Tyr Glu Arg Leu Leu Leu Glu Thr Met Arg Gly Ile
            420                 425                 430

Gln Ala Leu Phe Val Arg Arg Asp Glu Val Glu Ala Trp Lys Trp
        435                 440                 445

Val Asp Ser Ile Thr Glu Ala Trp Ala Met Asp Asn Asp Ala Pro Lys
450                 455                 460

Pro Tyr Gln Ala Gly Thr Trp Gly Pro Val Ala Ser Val Ala Met Ile
```

```
                465                 470                 475                 480
            Thr Arg Asp Gly Arg Ser Trp Asn Glu Phe Glu
                            485                 490

<210> SEQ ID NO 46
<211> LENGTH: 37
<212> TYPE: DNA
<213> ORGANISM: Artificial Sequence
<220> FEATURE:
<223> OTHER INFORMATION: Synthetic Primer: camA_F

<400> SEQUENCE: 46
taagaaggag atatacatat gaacgcaaac gacaacg                                    37

<210> SEQ ID NO 47
<211> LENGTH: 42
<212> TYPE: DNA
<213> ORGANISM: Artificial Sequence
<220> FEATURE:
<223> OTHER INFORMATION: Synthetic Primer: camA_R

<400> SEQUENCE: 47
catgaattct gtttcctgtg tgattaggca ctactcagtt ca                              42

<210> SEQ ID NO 48
<211> LENGTH: 42
<212> TYPE: DNA
<213> ORGANISM: Artificial Sequence
<220> FEATURE:
<223> OTHER INFORMATION: Synthetic Primer: camB_F

<400> SEQUENCE: 48
taatcacaca ggaaacagaa ttcatgtcta aagtagtgta tg                              42

<210> SEQ ID NO 49
<211> LENGTH: 40
<212> TYPE: DNA
<213> ORGANISM: Artificial Sequence
<220> FEATURE:
<223> OTHER INFORMATION: Synthetic Primer: camB_R

<400> SEQUENCE: 49
ggtttcttta ccagactcga ttaccattgc ctatcgggaa                                 40

<210> SEQ ID NO 50
<211> LENGTH: 36
<212> TYPE: DNA
<213> ORGANISM: Artificial Sequence
<220> FEATURE:
<223> OTHER INFORMATION: Synthetic Primer: camC_F

<400> SEQUENCE: 50
aagaaggaga tataccatga cgactgaaac cataca                                     36

<210> SEQ ID NO 51
<211> LENGTH: 40
<212> TYPE: DNA
<213> ORGANISM: Artificial Sequence
<220> FEATURE:
<223> OTHER INFORMATION: Synthetic Primer: camC_R

<400> SEQUENCE: 51
gcattatgcg gccgcaagct ttataccgct ttggtagtcg                                 40

<210> SEQ ID NO 52
```

```
<211> LENGTH: 37
<212> TYPE: DNA
<213> ORGANISM: Artificial Sequence
<220> FEATURE:
<223> OTHER INFORMATION: Synthetic Primer: P450bm3_F

<400> SEQUENCE: 52
aagaaggaga taccatga caattaaaga aatgcct                              37

<210> SEQ ID NO 53
<211> LENGTH: 40
<212> TYPE: DNA
<213> ORGANISM: Artificial Sequence
<220> FEATURE:
<223> OTHER INFORMATION: Synthetic Primer: P450bm3_R

<400> SEQUENCE: 53
gtggtggtgg tggtgctcga ttacccagcc cacacgtctt                         40

<210> SEQ ID NO 54
<211> LENGTH: 38
<212> TYPE: DNA
<213> ORGANISM: Artificial Sequence
<220> FEATURE:
<223> OTHER INFORMATION: Synthetic Primer: Zwf_F

<400> SEQUENCE: 54
ttaagaagga gatataccat ggcggtaacg caaacagc                           38

<210> SEQ ID NO 55
<211> LENGTH: 39
<212> TYPE: DNA
<213> ORGANISM: Artificial Sequence
<220> FEATURE:
<223> OTHER INFORMATION: Synthetic Primer: Zwf_R

<400> SEQUENCE: 55
tcgacctgca ggcgcgccgt tactcaaact cattccagg                          39

<210> SEQ ID NO 56
<211> LENGTH: 1371
<212> TYPE: DNA
<213> ORGANISM: Dehalobacter sp. CF

<400> SEQUENCE: 56
atggacaagg aaaaaagtaa caacgataag ccggcaacaa aaattaatcg cagacaattc    60
cttaaatttg gagctggagc ttcttcgggt attgcaattg ccactgcagc tactgcattg   120
ggagggaaat cacttatcga tcccaaacag gtatatgctg aacggtcaa ggaactggat   180 gaacttccct ttaatatccc ggcagactac aaaccgttta ccaatcaaag gaatatatat   240
ggccaggctg tattgggagt acccgaacct ctagcacttg tagagcgttt tgatgaagta   300
agatggaatg gttggcagac agatggttcg cccggtctta ctgtacttga tggtgcggct   360
gctcgtgcaa gctttgccgt tgattattat tttaacgggg aaaatagcgc ctgcagggcc   420
aataaaggtt ttttgaatg gcatcccaaa gtggccgagc tgaactttaa gtggggcgat   480
ccggagagaa atattcattc ccccggtgta aaaagtgccg aagaaggaac gatgcagta   540 aaaaaaatag ctagattttt cggcgctgct aaagctggga tagcgccttt tgacaaacgt   600 tgggtttttta ctgaaacgta tgcctttgtt aaaacgcctg agggtgaaag tctgaaattt   660
atccctccgg attttgggtt tgagcccaag catgtaatct cgatgattat cccacagtcg   720
ccagaaggag taaagtgtga cccgtccttt ttaggatcaa ctgaatatgg attaagttgt   780
```

```
gcccagattg gatatgctgc attcggttta tccatgttta ttaaagatct gggatatcat    840
gcggttccaa tcggatctga cagtgcatta gctatacccta tagctattca ggcgggtctg    900
ggggaataca gcaggtcggg gctaatgatt acgcctgaat ttggttcaaa tgttagactc    960
tgtgaagtat ttactgacat gcctttaaat catgataaac ctatttcatt cggagtaact   1020
gaattttgca aacctgcaa aaatgcgct gaagcatgcg ccctcaagc tattagctat      1080 gaagatccta ccattgatgg acctcgtggg caaatgcaaa attcgggaat aaagagatgg   1140
tatgttgacc cggtgaagtg cttagaattc atgtcgcgtg ataacgtcgg aaactgctgc   1200
ggagcttgta tagctgcttg cccatttact aagccggaag cctggcacca taccttaatt   1260
aggagtctag taggagcacc tgttattact ccattcatga agatatgga tgatattttt   1320 ggatacggaa agctgaatga tgaaaaagcg atagcagatt ggtggaaata a            1371
```

<210> SEQ ID NO 57
<211> LENGTH: 456
<212> TYPE: PRT
<213> ORGANISM: Dehalobacter sp. CF

<400> SEQUENCE: 57

```
Met Asp Lys Glu Lys Ser Asn Asn Asp Lys Pro Ala Thr Lys Ile Asn
1               5                   10                  15

Arg Arg Gln Phe Leu Lys Phe Gly Ala Gly Ala Ser Ser Gly Ile Ala
            20                  25                  30

Ile Ala Thr Ala Ala Thr Ala Leu Gly Gly Lys Ser Leu Ile Asp Pro
        35                  40                  45

Lys Gln Val Tyr Ala Gly Thr Val Lys Glu Leu Asp Glu Leu Pro Phe
    50                  55                  60

Asn Ile Pro Ala Asp Tyr Lys Pro Phe Thr Asn Gln Arg Asn Ile Tyr
65                  70                  75                  80

Gly Gln Ala Val Leu Gly Val Pro Glu Pro Leu Ala Leu Val Glu Arg
                85                  90                  95

Phe Asp Glu Val Arg Trp Asn Gly Trp Gln Thr Asp Gly Ser Pro Gly
            100                 105                 110

Leu Thr Val Leu Asp Gly Ala Ala Ala Arg Ala Ser Phe Ala Val Asp
        115                 120                 125

Tyr Tyr Phe Asn Gly Glu Asn Ser Ala Cys Arg Ala Asn Lys Gly Phe
    130                 135                 140

Phe Glu Trp His Pro Lys Val Ala Glu Leu Asn Phe Lys Trp Gly Asp
145                 150                 155                 160

Pro Glu Arg Asn Ile His Ser Pro Gly Val Lys Ser Ala Glu Glu Gly
                165                 170                 175

Thr Met Ala Val Lys Lys Ile Ala Arg Phe Phe Gly Ala Ala Lys Ala
            180                 185                 190

Gly Ile Ala Pro Phe Asp Lys Arg Trp Val Phe Thr Glu Thr Tyr Ala
        195                 200                 205

Phe Val Lys Thr Pro Glu Gly Glu Ser Leu Lys Phe Ile Pro Pro Asp
    210                 215                 220

Phe Gly Phe Glu Pro Lys His Val Ile Ser Met Ile Pro Gln Ser
225                 230                 235                 240

Pro Glu Gly Val Lys Cys Asp Pro Ser Phe Leu Gly Ser Thr Glu Tyr
                245                 250                 255

Gly Leu Ser Cys Ala Gln Ile Gly Tyr Ala Ala Phe Gly Leu Ser Met
            260                 265                 270
```

```
Phe Ile Lys Asp Leu Gly Tyr His Ala Val Pro Ile Gly Ser Asp Ser
    275                 280                 285
Ala Leu Ala Ile Pro Ile Ala Ile Gln Ala Gly Leu Gly Glu Tyr Ser
    290                 295                 300
Arg Ser Gly Leu Met Ile Thr Pro Glu Phe Gly Ser Asn Val Arg Leu
305                 310                 315                 320
Cys Glu Val Phe Thr Asp Met Pro Leu Asn His Asp Lys Pro Ile Ser
                325                 330                 335
Phe Gly Val Thr Glu Phe Cys Lys Thr Cys Lys Cys Ala Glu Ala
                340                 345                 350
Cys Ala Pro Gln Ala Ile Ser Tyr Glu Asp Pro Thr Ile Asp Gly Pro
                355                 360                 365
Arg Gly Gln Met Gln Asn Ser Gly Ile Lys Arg Trp Tyr Val Asp Pro
    370                 375                 380
Val Lys Cys Leu Glu Phe Met Ser Arg Asp Asn Val Gly Asn Cys Cys
385                 390                 395                 400
Gly Ala Cys Ile Ala Ala Cys Pro Phe Thr Lys Pro Glu Ala Trp His
                405                 410                 415
His Thr Leu Ile Arg Ser Leu Val Gly Ala Pro Val Ile Thr Pro Phe
                420                 425                 430
Met Lys Asp Met Asp Asp Ile Phe Gly Tyr Gly Lys Leu Asn Asp Glu
                435                 440                 445
Lys Ala Ile Ala Asp Trp Trp Lys
    450                 455
```

<210> SEQ ID NO 58
<211> LENGTH: 38
<212> TYPE: DNA
<213> ORGANISM: Artificial Sequence
<220> FEATURE:
<223> OTHER INFORMATION: primer

<400> SEQUENCE: 58
gacgcttacg gaggctctat gataaatgca attcgcac        38

<210> SEQ ID NO 59
<211> LENGTH: 36
<212> TYPE: DNA
<213> ORGANISM: Artificial Sequence
<220> FEATURE:
<223> OTHER INFORMATION: primer

<400> SEQUENCE: 59
tggcagttcc ctactctcct attctgtctc ggcaaa        36

<210> SEQ ID NO 60
<211> LENGTH: 3914
<212> TYPE: DNA
<213> ORGANISM: Artificial Sequence
<220> FEATURE:
<223> OTHER INFORMATION: Synthetic pTSa_DhlA vector

<400> SEQUENCE: 60
ataaaacgaa aggctcagtc gaaagactgg gcctttcgtt ttatctgttg tttgtcggtg        60
aacgctctcc tgagtaggac aaatccgccg ggagcggatt tgaacgttgc gaagcaacgg       120
cccggagggt ggcgggcagg acgcccgcca taaactgcca ggcatcaaat taagcagaag       180
gccatcctga cggatggcct ttttggaatt cagccagcaa gacagcgata gagggtagtt       240

```
atccacgtga aaccgctaat gccccgcaaa gccttgattc acggggcttt ccggcccgct    300
ccaaaaacta tccacgtgaa atcgctaatc agggtacgtg aaatcgctaa tcggagtacg    360
tgaaatcgct aataaggtca cgtgaaatcg ctaatcaaaa aggcacgtga aacgctaat    420
agcccttca gatcaacagc ttgcaaacac ccctcgctcc ggcaagtagt tacagcaagt    480
agtatgttca attagctttt caattatgaa tatatatatc aattattggt cgcccttggc    540
ttgtggacaa tgcgctacgc gcaccggctc cgcccgtgga caaccgcaag cggttgccca    600
ccgtcgagcg ccagcgcctt tgcccacaac ccggcggccg ccgcaacag atcgttttat    660
aaattttttt ttttgaaaaa gaaaagccc gaaaggcggc aacctctcgg gcttctggat    720
ttccgatcac ctgtaagtcg gacgaattcg gcgctcttcc gcttcctcgc tcactgactc    780
gctgcgctcg gtcgttcggc tgcggcgagc ggtatcagct cactcaaagg cggtaatacg    840
gttatccaca gaatcagggg ataacgcagg aaagaacatg tgagcaaaag ccagcaaaa    900
ggccaggaac cgtaaaaagg ccgcgttgct ggcgtttttc cataggctcc gccccctga    960
cgagcatcac aaaaatcgac gctcaagtca gaggtggcga aacccgacag gactataaag   1020
ataccaggcg tttccccctg gaagctccct cgtgcgctct cctgttccga ccctgccgct   1080
taccggatac ctgtccgcct ttctcccttc gggaagcgtg gcgctttctc atagctcacg   1140
ctgtaggtat ctcagttcgg tgtaggtcgt tcgctccaag ctgggctgtg tgcacgaacc   1200
ccccgttcag cccgaccgct gcgccttatc cggtaactat cgtcttgagt ccaacccggt   1260
aagacacgac ttatcgccac tggcagcagc cactggtaac aggattagca gagcgaggta   1320
tgtaggcggt gctacagagt tcttgaagtg gtggcctaac tacggctaca ctagaagaac   1380
agcatttggt atctgcgctc tgctgaagcc agttaccttc ggaaaaagag ttggtagctc   1440
ttgatccggc aaacaaacca ccgctggtag cggtggtttt tttgtttgca agcagcagat   1500
tacgcgcaga aaaaaggat ctcaagaaga tcctttgatc ttttctacgg ggtctgacgc   1560
tcagtggaac gaaaactcac gttaattctc atgtttgaca gcttatcatc gataagcttt   1620
aatgcggtag tttatcacag ttaaattgct aacgcagtca ggcaccgtgt atgaaatcta   1680
acaatgcgct catcgtcatc ctcggcaccg tcaccctgga tgctgtaggc ataggcttgg   1740
ttatgccggt actgccgggc ctcttgcggg atatcgtcca ttccgacagc atcgccagtc   1800
actatggcgt gctgctagcg ctatatgcgt tgatgcaatt tctatgcgca cccgttctcg   1860
gagcactgtc cgaccgcttt ggccgccgcc cagtcctgct cgcttcgcta cttggagcca   1920
ctatcgacta cgcgatcatg gcgaccacac ccgtcctgtg gatcctctac gccggacgca   1980
tcgtggccgg catcaccggc gccacaggtg cggttgctgg cgcctatatc gccgacatca   2040
ccgatgggga gatcgggct cgccacttcg ggctcatgag cgcttgtttc ggcgtgggta   2100
tggtggcagg ccccgtggcc gggggactgt tgggcgccat ctccttgcat gcaccattcc   2160
ttgcggcggc ggtgctcaac ggcctcaacc tactactggg ctgcttccta atgcaggagt   2220
cgcataaggg agagcgtcga ccgatgccct tgagagcctt caacccagtc agctccttcc   2280
ggtgggcgcg gggcatgact atcgtcgccg cacttatgac tgtcttcttt atcatgcaac   2340
tcgtaggaca ggtgccggca gcgctctggg tcattttcgg cgaggaccgc tttcgctgga   2400
gcgcgacgat gatcggcctg tcgcttgcgg tattcggaat cttgcacgcc ctcgctcaag   2460
ccttcgtcac tggtcccgcc accaaacgtt tcggcgagaa gcaggccatt atcgccggca   2520
tggcggccga cgcgctgggc tacgtcttgc tggcgttcgc gacgcgaggc tggatggcct   2580
tccccattat gattcttctc gcttccggcg gcatcgggat gcccgcgttg caggccatgc   2640
```

| | |
|---|---:|
| tgtccaggca ggtagatgac gaccatcagg gacagcttca aggatcgctc gcggctctta | 2700 |
| ccagcctaac ttcgatcact ggaccgctga tcgtcacggc gatttatgcc gcctcggcga | 2760 |
| gcacatggaa cgggttggca tggattgtag gcgccgccct ataccttgtc tgcctccccg | 2820 |
| cgttgcgtcg cggtgcatgg agccgggcca cctcgacctg aatggaagcc ggcggcacct | 2880 |
| cgctaacgga ttcaccactc ttgacattgt aggtcaggcg acctactttg tcattgctag | 2940 |
| gtcacccgac ctaactttg acagacgctt acggaggctc tatgataaat gcaattcgca | 3000 |
| ccccggacca acgcttcagc aatctcgatc agtatccgtt cagccccaac tacctggacg | 3060 |
| acctccccgg ctacccggga ttgcgggcac actacctcga cgagggcaat tctgacgctg | 3120 |
| aagacgtttt tctctgcctt catggcgagc ccacctggag ttacctgtat cgcaagatga | 3180 |
| tcccggtatt tgctgaatca ggcgcacgag ttattgcgcc agactttttt ggattcggaa | 3240 |
| aatccgacaa gccagtagac gaagaagact acaccttcga atttcaccgc aacttcctgc | 3300 |
| ttgcactaat cgaacggctt gacttgcgca acattacgct ggtcgttcag gactggggcg | 3360 |
| gattttgg gctgaccta ccgatggccg acccttcccg cttcaagcgc ctgatcatca | 3420 |
| tgaacgcctg cttgatgacc gacccggtca cccagcctgc gtttagcgcc tttgtcaccc | 3480 |
| agcctgcgga tggctttacc gcctggaaat acgatctggt tacgccatca gacctgcgcc | 3540 |
| ttgaccagtt catgaagcgt tgggcgccca cactgaccga agctgaggcc tccgcgtatg | 3600 |
| ctgcgccttt ccctgacact tcctatcagg ctggtgtacg caagtttccc aagatggtcg | 3660 |
| cgcaacgcga ccaggcctgc atcgacattt caaccgaagc gatttcgttc tggcagaacg | 3720 |
| actggaatgg ccagaccttc atggccattg gcatgaaaga caaattgctg ggaccggacg | 3780 |
| tcatgtatcc tatgaaggcg ctcattaatg gctgcccgga acccctcgaa atagcggacg | 3840 |
| ctggccattt cgtacaggag tttggcgagc aagtggctcg cgaggccctg aaacactttg | 3900 |
| ccgagacaga atag | 3914 |

<210> SEQ ID NO 61
<211> LENGTH: 933
<212> TYPE: DNA
<213> ORGANISM: Artificial Sequence
<220> FEATURE:
<223> OTHER INFORMATION: Synthetic Xanthobacter autotrophicus haloalkane dehalogenase_dhlA codon optimized

<400> SEQUENCE: 61

| | |
|---|---:|
| atgatcaacg caatccgcac ccctgaccaa cgtttcagca acctggacca atacccttc | 60 |
| agccctaact acctggacga cctgccaggt tacccaggtc tgcgtgcaca ttacctggac | 120 |
| gaaggtaaca cgcgacgctga agacgttttc ctgtgtctgc acggtgaacc aacttggagc | 180 |
| tacctgtacc gtaagatgat cccggtcttc gctgagtccg gtgcacgtgt tatcgcaccg | 240 |
| gatttcttcg gttccggtaa gtccgacaag ccggtagatg aggaggatta caccttcgag | 300 |
| ttccaccgta acttcctgct ggcgctgatc gaacgtctgg atctgcgtaa catcaccctg | 360 |
| gtcgtgcagg attggggtgg tttcctgggt ctgactctgc cgatggcaga tccgtctcgt | 420 |
| tttaaacgtc tgatcatcat gaacgcctgc ctgatgaccg acccggtaac tcagccggca | 480 |
| ttttccgcat tcgttactca gccggcggat ggctttactg cttggaaata tgacctggtg | 540 |
| acgccgtctg atctgcgtct ggatcagttc atgaaacgct gggctccgac cctgaccgaa | 600 |
| gctgaagctt ctgcttatgc tgcgccgttt ccggatacct cttatcaggc cggcgtacgc | 660 |
| aaatttccga aaatggtggc gcagcgcgat caggcgtgta ttgatatttc tacggaagcg | 720 |

```
atctccttct ggcagaacga ctggaatggc cagaccttca tggccattgg catgaaagac      780
aaactgctgg gcccggacgt tatgtatccg atgaaagcgc tgattaatgg ctgcccggaa      840
ccgctggaaa ttgcggacgc cggccatttt gtgcaggaat tcggcgaaca ggttgcgcgc      900
gaagccctga aacactttgc ggaaaccgaa taa                                   933
```

MICROORGANISM INCLUDING GENE ENCODING PROTEIN HAVING HYDROXYLASE ACTIVITY AND METHOD OF REDUCING CONCENTRATION OF FLUORINATED METHANE IN SAMPLE USING THE SAME

CROSS-REFERENCE TO RELATED APPLICATIONS

This application claims the benefit of Korean Patent Application No. 10-2015-0066949, filed on May 13, 2015, Korean Patent Application No. 10-2015-0148032, filed on Oct. 23, 2015, Korean Patent Application No. 10-2015-0173293, filed on Dec. 7, 2015, Korean Patent Application No. 10-2015-0185093, filed on Dec. 23, 2015, and Korean Patent Application No. 10-2016-0048960, filed on Apr. 21, 2016, in the Korean Intellectual Property Office, the entire disclosures of which are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 92,392 Byte ASCII (Text) file named "724225_ST25.TXT," created on May 12, 2016.

BACKGROUND

1. Field

The present disclosure relates to a microorganism including a gene encoding a protein having a hydroxylase activity, a composition for using in reducing a concentration of fluorinated methane in a sample, the composition including the microorganism including the gene encoding the protein having the hydroxylase activity, and a method of reducing the concentration of fluorinated methane in the sample.

2. Description of the Related Art

The emissions of greenhouse gases which have accelerated global warming are one of the serious environmental problems, and regulations to reduce and prevent the emissions of greenhouse gases have been tightened. Among the greenhouse gases, fluorinated gases (F-gas) such as perfluorocarbons (PFCs), hydrofluorocarbons (HFCs), or $SF_6$ show low absolute emission, but have a long half-life and a very high global warming potential, resulting in significant adverse environmental impacts. The amount of F-gas emitted from semiconductor and electronics industries which are major causes of F-gas emission has exceeded the assigned amount of greenhouse gas emissions and continues to increase. Therefore, costs required for degradation of greenhouse gases and greenhouse gas emission allowances are increasing every year.

A pyrolysis or catalytic thermal oxidation process has been generally used in the decomposition of F-gas. However, this process has disadvantages of limited decomposition rate, emission of secondary pollutants, high cost, etc. To solve this problem, biological decomposition of F-gas using a microbial biocatalyst has been adopted. Accordingly, it is expected to overcome the limitations of the chemical decomposition process and to treat F-gas in more economical and environmentally-friendly manner.

Hydroxylase is an enzyme that catalyzes introduction of a hydroxyl group (—OH) to carbon of a carbon-containing compound (RH), thereby converting a CH group into a COH group in a carbon-containing compound. The hydroxylase includes monooxygenase and dehalogenase. Monooxygenase catalyzes incorporation of one oxygen atom to the carbon position of a carbon-containing compound and reduction of another oxygen atom to water. Monooxygenase includes cytochrome P450 and methane monooxygenase (MMO). Cytochrome P450 belongs to the superfamily of proteins containing a heme cofactor, and therefore, cytochrome P450 is a hemoprotein. The dehalogenase is a type of enzyme that catalyzes the removal of a halogen atom from a substrate.

Despite the efforts of the prior art, there have been no reports about a microorganism including a hydroxylase gene which acts on fluorinated methane, a composition for and a method of reducing a concentration of fluorinated methane in a sample using the same.

SUMMARY

An aspect provides a recombinant microorganism including one or more foreign genes encoding a protein having a hydroxylase activity, in which the microorganism has an increased hydroxylase activity, compared to a parent strain of the recombinant microorganism.

Another aspect provides a composition for using in reducing a concentration of $CH_nF_{4-n}$ (where n is an integer of 0 to 3) in a sample, the composition including the recombinant microorganism, a lysate thereof, or an aqueous fraction of the lysate, in which the recombinant microorganism includes one or more foreign genes encoding the protein having the hydroxylase activity, and the recombinant microorganism has the increased hydroxylase activity, compared to a parent strain of the recombinant microorganism.

Still another aspect provides a method of reducing a concentration of $CH_nF_{4-n}$ in a sample, the method including contacting the recombinant microorganism, the lysate thereof, or the aqueous fraction of the lysate with the sample containing $CH_nF_{4-n}$ (where n is an integer of 0 to 3) to reduce the concentration of $CH_nF_{4-n}$ (where n is an integer of 0 to 3) in the sample, in which the recombinant microorganism includes one or more foreign genes encoding the protein having the hydroxylase activity, and the recombinant microorganism has the increased hydroxylase activity, compared to a parent strain of the recombinant microorganism.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
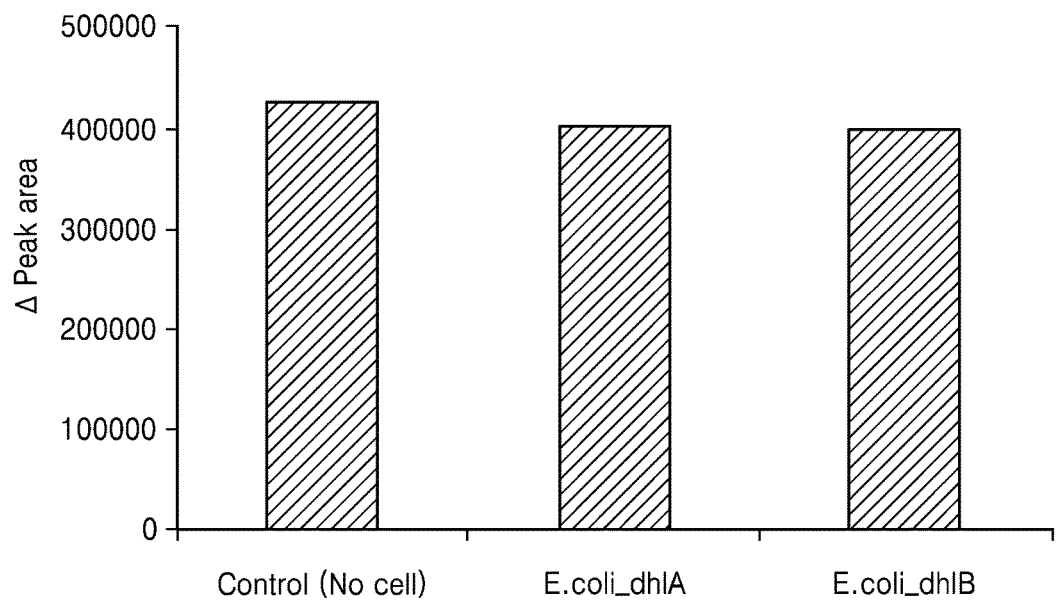
FIG. 1A shows the experimental result of decomposing fluoroform by recombinant E. coli.

An aspect provides a recombinant microorganism including one or more foreign genes encoding a protein having a hydroxylase activity, in which the microorganism has an increased hydroxylase activity, compared to a parent strain of the recombinant microorganism. A parent strain of the microorganism is a microorganism of the same type without a given genetic modification (e.g. introduction of a foreign gene) that gives rise to the recombinant microorganism.

With regard to the microorganism, the protein having the hydroxylase activity may be an enzyme that catalyzes introduction of a hydroxyl group (—OH) to carbon of a carbon-containing compound (RH). Hydroxylase may catalyze conversion of a CH group into a COH group in a carbon-containing compound. The protein having the hydroxylase activity may acts on a carbon-fluorine bond or a carbon-hydrogen bond in a fluoroalkane compound.

The protein having hydroxylase activity may be selected from the group consisting of dehalogenase and monooxygenase.

Dehalogenase is a type of enzyme that catalyzes the removal of a halogen atom from a substrate. Dehalogenase may belong to EC 3.8.1.-. Dehalogenase may be chloroform reductive dehalogenase CfrA, tetrachloroethene reductive dehalogenase, dichloromethane dehalogenase, haloalkane dehalogenase, alkylhalidase, (S)-2-haloacid dehalogenase, (R)-2-haloacid dehalogenase, 2-haloacid dehalogenase (configuration-inverting), haloacetate dehalogenase, or a combination thereof.

The protein having the hydroxylase activity may have 95% or higher, 96% or higher, 97% or higher, 98% or higher, or 99% or higher sequence identity to SEQ ID NO: 1 or 2. The protein having the hydroxylase activity may have an amino acid sequence of SEQ ID NO: 1 or 2. The protein having the amino acid sequence of SEQ ID NO: 1 may be classified into haloalkane dehalogenase. The protein having the amino acid sequence of SEQ ID NO: 1 may be an enzyme that catalyzes production of primary alcohol and halide from 1-haloalkane and water as substrates. The protein having the amino acid sequence of SEQ ID NO: 2 may be classified into (S)-2-haloacid dehalogenase. Further, the protein having the amino acid sequence of SEQ ID NO: 2 may be an enzyme that catalyzes production of (R)-hydroxy acid and halide from (S)-2-haloacid and water as substrates. The one or more foreign genes encoding the protein having the hydroxylase activity may have nucleotide sequences of SEQ ID NOS: 3 and 4. Further, the gene may be codon-optimized with respect to the recombinant microorganism as a host cell. Codon optimization refers to production of a gene in which one or more endogenous codons are replaced with codons for the same amino acid but of preference in the corresponding host. The nucleotide sequences of SEQ ID NOS: 3 and 4 are genes encoding haloalkane dehalogenase (dhlA) and (S)-2-haloacid dehalogenase (dhlB) derived from *Xanthobacter autotrophicus*, respectively. The nucleotide sequence of SEQ ID NOS: 61 is gene encoding haloalkane dehalogenase (dhlA) codon optimized for *E. coli*. Chloroform reductive dehalogenase CfrA may have an amino acid sequence of SEQ ID NO: 57, and may be encoded by a nucleotide sequence of SEQ ID NO: 56. CfrA is known to dechlorinate chloroform (CF) and 1,1,1-trichloroethane (1,1,1-TCA), but not 1,1-dichloroethane.

With regard to the recombinant microorganism, monooxygenase catalyzes a monooxygenase reaction of incorporating one oxygen atom to the carbon position of a carbon-containing compound and reducing another oxygen atom to water. Monooxygenase may belong to EC 1.14.13.-. Monooxygenase includes methane monooxygenase (MMO) and cytochrome P450. Methane monooxygenase is an enzyme capable of oxidizing the C—H bond in methane. Cytochrome P450 (CYP) belongs to the superfamily of proteins containing a heme cofactor, and therefore, cytochrome P450 is a hemoprotein.

Methane monooxygenase may be soluble methane monooxygenase (sMMO), particular methane monooxygenase, ammonia monooxygenase, camphor 5-monooxygenase, or a combination thereof. The sMMO protein may belong to EC 1.14.13.25. The sMMO protein may be derived from *Methylococcus capsulatus* (Bath). The sMMO protein may include a complex of MmoX, MmoY, and MmoZ, MmoB, MmoC, and MmoD. MmoX, MmoY, MmoZ, MmoB, MmoC, and MmoD may have amino acid sequences of SEQ ID NOS: 5, 7, 9, 11, 13, and 15, respectively. Polynucleotides encoding MmoX, MmoY, MmoZ, MmoB, MmoC, and MmoD may have nucleotide sequences of SEQ ID NOS: 6, 8, 10, 12, 14, and 16, respectively. With regard to the recombinant microorganism, the gene may include a polynucleotide having the nucleotide sequence of SEQ ID NO: 6, a polynucleotide having the nucleotide sequence of SEQ ID NO: 8, a polynucleotide having the nucleotide sequence of SEQ ID NO: 10, a polynucleotide having the nucleotide sequence of SEQ ID NO: 12, a polynucleotide having the nucleotide sequence of SEQ ID NO: 14, and a polynucleotide having the nucleotide sequence of SEQ ID NO: 16. With regard to the recombinant microorganism, the gene may be included in a polynucleotide having a nucleotide sequence of SEQ ID NO: 35. In other words, the recombinant microorganism may include the polynucleotide having the nucleotide sequence of SEQ ID NO: 35.

The recombinant microorganism may further include a foreign gene encoding MmoG. MmoG may have an amino acid sequence of SEQ ID NO: 17. A polynucleotide encoding MmoG may have a nucleotide sequence of SEQ ID NO: 18.

The recombinant microorganism may belong to the genus *Escherichia* or *xanthobacter*. The genus *Escherichia* may include *Escherichia coli*. The genus *xanthobacter* may include *Xanthobacter autotrophicus*.

With regard to the recombinant microorganism, the cytochrome P450 may be any cytochrome P450, as long as it is expressed from the gene in the microorganism to have a monooxygenase activity. The cytochrome P450 may be a bacterial P450. The cytochrome P450 protein may belong to EC 1.14.15.1 or EC 1.14.14.1. The cytochrome P450 protein may be $P450_{cam}$ or $P450_{BM3}$. $P450_{cam}$ may be derived from *Pseudomonas putida* PpG786. $P450_{BM3}$ may be derived from *Bacillus megaterium* (ATCC 14581). The cytochrome P450 protein may be a complex of CamA, CamB, and CamC. CamA, CamB, and CamC may have amino acid sequences of SEQ ID NOS: 37, 39, and 41, respectively. Genes encoding CamA, CamB, and CamC may have nucleotide sequences of SEQ ID NOS: 36, 38, and 40, respectively.

$P450_{BM3}$ may be a protein having an amino acid sequence of SEQ ID NO: 43. A gene encoding $P450_{BM3}$ may have a nucleotide sequence of SEQ ID NO: 42.

The gene may include one or more nucleotide sequences of SEQ ID NOS: 36, 38, 40 and 42.

The recombinant microorganism may have genetic modification of increasing a level of an enzyme that catalyzes a NADPH production reaction to increase an intracellular NADPH level by the reaction. The genetic modification includes amplification of an endogenous gene and introduction of a foreign gene. The enzyme may be a protein belonging to EC 1.1.1.49. The enzyme may be glucose-6-phosphate dehydrogenase (G6PD or G6PDH). The recombinant microorganism may further include a foreign gene encoding G6PDH.

With regard to the recombinant microorganism, the microorganism may include one or more, for example, 2 or more, 3 or more, 4 or more, 5 or more, 10 or more, or 50 or more foreign genes encoding the proteins having hydroxylase activity. When a plurality of genes is included in the microorganism, the genes may be different from each other or they may include multiple copies of the same gene. The genes may be integrated into the genome of the microorganism, or independent of the genome.

The recombinant microorganism may reduce a concentration of $CH_nF_{4-n}$ (where n is an integer of 0 to 3) (hereinbelow, referred to as "fluorinated methane") in a sample. The reducing may be performed by introducing a hydroxyl group to carbon of the fluorinated methane by action of the protein on C—F or C—H bond thereof or by accumulating the fluorinated methane inside the cell of the microorganism. Further, the reducing may include cleaving of C—F bonds of $CH_nF_{4-n}$, converting of $CH_nF_{4-n}$ into other materials, or intracellular accumulating of $CH_nF_{4-n}$. The sample may be in a liquid or gas state. The sample may be industrial waste water or waste gas. The sample may be any sample including the fluorinated methane. The fluorinated methane may include $CF_4$, $CHF_3$, $CH_2F_2$, $CH_3F$, or a mixture thereof.

The recombinant microorganism may include foreign genes encoding one or more proteins having the hydroxylase activity selected from the group consisting of haloalkane dehalogenase (dhlA) derived from *Xanthobacter autotrophicus*, (S)-2-haloacid dehalogenase (dhlB) derived from *Xanthobacter autotrophicus*, $P450_{CAM}$ derived from *Pseudomonas putida*, $P450_{BM3}$ derived from *Bacillus megaterium*, and soluble methane monooxygenase (sMMO) derived from *Methylococcus capsulatus*.

With regard to the recombinant microorganism, the gene may be introduced into the microorganism by a general method known in the art, for example, transformation, electroporation, etc.

Another aspect provides a composition used for reducing a concentration of $CH_nF_{4-n}$ (where n is an integer of 0 to 3) in a sample, the composition including the recombinant microorganism, a lysate thereof, or an aqueous fraction of the lysate, in which the recombinant microorganism includes one or more foreign genes encoding the protein having the hydroxylase activity, and the recombinant microorganism has the increased hydroxylase activity, compared to a parent strain of the recombinant microorganism.

With regard to the composition, the recombinant microorganism, sample and fluorinated methane are the same as described above.

The lysate refers to the contents of the microorganism exposed to the outside of the cell, which are obtained by disruption of the microorganism. The lysate may be obtained by disrupting the microorganism using enzymes such as protease and lipase, heat, pressure, etc. The "aqueous fraction" may be obtained from a material dissolved in an aqueous solvent. The aqueous solvent may be water. In some embodiments, the "aqueous fraction" is the entire aqueous fraction, i.e., the fraction extracted with an aqueous solvent without further purification or isolation of components from the aqueous fraction.

With regard to the composition, the term "reducing" includes reducing the concentration of fluorinated methane in the sample or completely removing fluoridated methane from the sample. The sample may be a gas or a liquid. The sample can be free of a microorganism. The composition may further include a material that increases the solubility of the fluorinated methane in a medium or a culture.

The composition may reduce the concentration of fluorinated methane in the sample by contacting with the sample. The contacting may be performed in a liquid or solid phase. The contacting may be performed, for example, by contacting a culture of the microorganism with the sample during culturing. The culturing may be performed under conditions where the microorganism may proliferate.

Still another aspect provides a method of reducing a concentration of $CH_nF_{4-n}$ in a sample, the method including contacting the recombinant microorganism, the lysate thereof, or the aqueous fraction of the lysate with the sample containing $CH_nF_{4-n}$ (where n is an integer of 0 to 3) to reduce the concentration of $CH_nF_{4-n}$ (where n is an integer of 0 to 3) in the sample, in which the recombinant microorganism includes one or more foreign genes encoding the protein having the hydroxylase activity, and the recombinant microorganism has the increased hydroxylase activity, compared to a parent strain of the recombinant microorganism.

With regard to the method, as the recombinant microorganism including one or more foreign genes encoding the protein having the hydroxylase activity, the microorganism having the increased hydroxylase activity, compared to a parent strain of the recombinant microorganism, the lysate thereof, or aqueous fraction of the lysate, and $CH_nF_{4-n}$ (where n is an integer of 0 to 3)-containing sample are the same as described above.

With regard to the method, the contacting may be performed in a liquid or solid phase. The contacting may be performed, for example, by contacting a culture of the cultured microorganism with the sample during culturing. The culturing may be performed under conditions where the microorganism may proliferate. The contacting may be performed in a sealed container. The contacting may be performed when the growth stage of the microorganism is in an exponential phase or a stationary phase. The culturing may be performed under aerobic or anaerobic conditions. The contacting may be performed in the sealed container under conditions where the recombinant microorganism may survive. The conditions where the recombinant microorganism may survive may be conditions where the recombinant microorganism may proliferate or conditions where the recombinant microorganism may be allowed to be in a resting state.

With regard to the method, the sample may be in a liquid or gas state. The sample may be industrial waste water or waste gas. The sample may include passive contacting of the sample with the culture of the microorganism and active contacting of the sample with the culture of the microorganism. The sample may be, for example, sparged into the culture of the microorganism. That is, the sample may be sparged into a medium or culture. The sparging may be sparging of the sample from the bottom to the top of the medium or culture. The sparging may be injecting of droplets of the sample.

With regard to the method, the contacting may be performed in a batch or continuous manner. The contacting may include, for example, contacting a fresh recombinant microorganism, lysate thereof, or aqueous fraction of the lysate with the sample obtained in the reducing, in which the recombinant microorganism includes one or more foreign genes encoding the protein having hydroxylase activity, and the recombinant microorganism has increased hydroxylase activity, compared to a parent strain of the recombinant microorganism. The contacting with the fresh microorganism, lysate thereof, or aqueous fraction of the lysate may be performed twice or more, for example, twice, three times, five times, or ten times or more. The contacting may be continued or repeated until the concentration of fluorinated methane in the sample reaches a desired reduced concentration.

The recombinant microorganism according to an aspect may be used for removing $CH_nF_{4-n}$ in the sample.

The composition according to another aspect may be used for removing $CH_nF_{4-n}$ in the sample.

The method of reducing the concentration of $CH_nF_{4-n}$ in the sample according to still another aspect may be used to efficiently reduce the concentration of $CH_nF_{4-n}$ in the sample.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

Hereinafter, the present invention will be described in more detail with reference to Examples. However, these Examples are for illustrative purposes only, and the scope of the invention is not intended to be limited by these Examples.

Example 1: Decomposition of Fluoroform by Dehalogenase-Introduced *E. coli*

(1) Introduction of Dehalogenase Gene into *E. coli*

(1.1) Introduction of dhlA and dhlB Genes

Haloalkane dehalogenase (dhlA) and (S)-2-haloacid dehalogenase (dhlB) of *Xanthobacter autotrophicus* GJ10 were selected as enzymes having activity of decomposing fluoro-containing hydrocarbon. *Xanthobacter autotrophicus* GJ10 was purchased from German Collection of Microorganisms and Cell Cultures (DSMZ).

A gene encoding haloalkane dehalogenase (dhlA) (SEQ ID NO: 3) and a gene encoding (S)-2-haloacid dehalogenase (dhlB) (SEQ ID NO: 4) were inserted into NdeI and HindIII sites of a pET28a vector (Novagen), respectively to obtain a dhlA-expressing vector, pET28a_dhlA and a dhlB-expressing vector, pET28a_dhlB. These vectors were introduced into *E. coli*, respectively and then their introduction was confirmed by sequencing. The haloalkane dehalogenase-introduced *E. coli* and (S)-2-haloacid dehalogenase-introduced *E. coli* were designated as *E. coli*_dhlA and *E. coli*_dhlB, respectively.

(1.2) Introduction of CfrA Gene

A gene (SEQ ID NO: 56) encoding chloroform reductive dehalogenase (CfrA) of *Dehalobacter* sp. CF was inserted into EcoRI site of a pMALc2 vector (New England Biolabs Inc.) to obtain a CrfA-expressing vector, pMALc2-CfrA. This vector was introduced into *E. coli* BL21 Star, and its introduction was confirmed by sequencing. The CfrA gene-introduced *E. coli* was designated as *E. coli* BL21 star/pMALc2-CfrA.

(2) Decomposition of Fluoroform by Haloalkane Dehalogenase-Introduced *E. coli*

*E. coli*_dhlA and *E. coli*_dhlB obtained in section (1) were put at a density of $2 \times 10^9$ cells/ml in a M9 medium-containing shaking reactor (Daihan Labtech), respectively and incubated in a shaking incubator (Daihan Labtech) together with $CHF_3$ at an initial concentration of 200 ppm (see FIG. 1A) or 600 ppm (performed only for *E. coli*_dhlA: see FIG. 1B) in a headspace volume for 48 hours at 30° C. under shaking at 230 rpm. Then, an amount of $CHF_3$ in the headspace was analyzed. For analysis, 0.5 ml was collected from the headspace using a syringe and injected into GC (Agilent 7890, Palo Alto, Calif., USA). The injected $CHF_3$ was separated through a CP-PoraBOND Q column (25 m length, 0.32 mm i.d., 5 um film thickness, Agilent), and changes in the $CHF_3$ concentration were analyzed by MSD (Agilent 5973, Palo Alto, Calif., USA). As a carrier gas, helium was used, and applied to the column at a flow rate of 1.5 ml/min. GC conditions were as follows: An inlet temperature was 250° C., an initial temperature was maintained at 40° C. for 2 minutes, and temperature was raised to 290° C. at a rate of 20° C./min. MS conditions were as follows: Ionization energy was 70 eV, an interface temperature was 280° C., an ion source temperature was 230° C., and a quadrupole temperature was 150° C. Unless otherwise mentioned, analysis of gas such as $CHF_3$, $CHCl_3$, and $CF_4$ was performed by using the above method. As a control group, 200 ppm of $CHF_3$ was incubated without the cells under the same conditions, and then measured. The M9 medium included 0.015 g/l of $CaCl_2$, 6 g of $Na_2HPO_4$, 3 g of $KH_2PO_4$, 0.5 g of NaCl, 1 g of $NH_4Cl$, 0.5 g/l of $MgSO_4$, and 2.0 g/l glucose.

FIG. 1A shows the experimental result of decomposing fluoroform by recombinant E. coli. As shown in FIG. 1A, E. coli_dhlA and E. coli_dhlB showed 6% and 7% reduction in the amount of fluoroform, respectively. This result of FIG. 1A indicates that haloalkane dehalogenase and (S)-2-haloacid dehalogenase have a fluoroform decomposition ability.

Figure 1B:
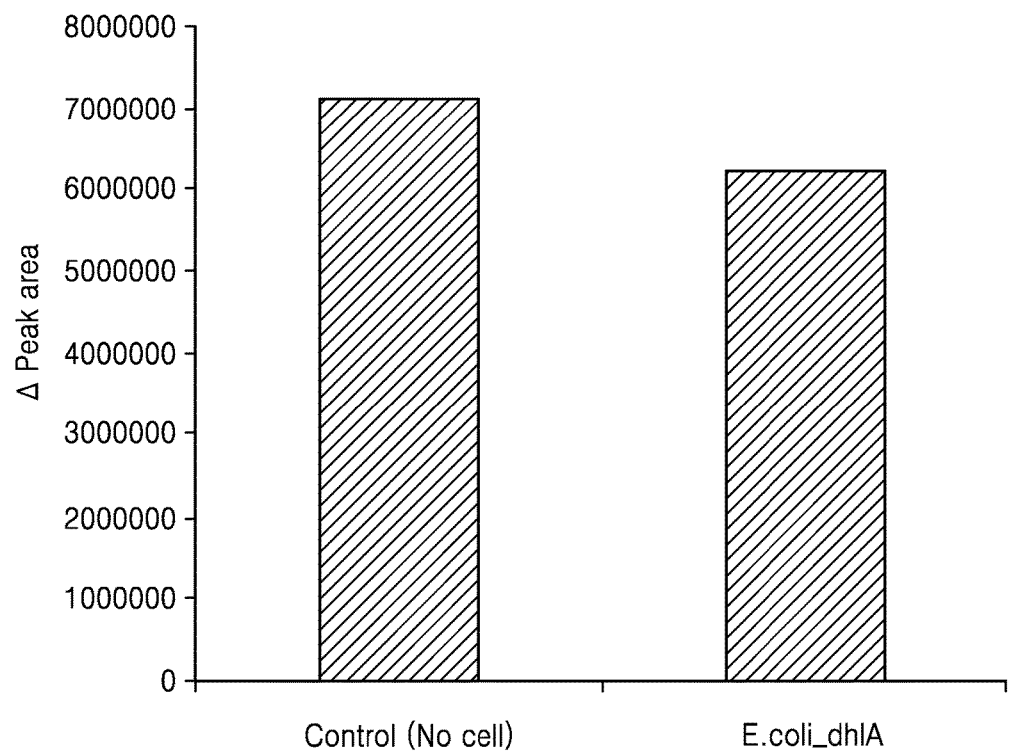
FIG. 1B shows the experimental result of decomposing fluoroform by haloalkane dehalogenase-introduced E. coli.

FIG. 1B shows the experimental result of decomposing fluoroform by haloalkane dehalogenase-introduced E. coli. As shown in FIG. 1B, E. coli_dhlA showed 12.4% reduction in the amount of fluoroform, compared to the control group. This result of FIG. 1B indicates that haloalkane dehalogenase-introduced E. coli is able to decompose a larger amount of trifluoromethane per hour as the initial concentration of trifluoromethane is higher.

(3) Decomposition of Perfluoromethane by Haloalkane Dehalogenase-Introduced E. coli It is examined whether E. coli introduced with Xanthobacter autotrophicus GJ10-derived haloalkane dehalogenase has an ability to decompose perfluoromethane ($CF_4$).

A reduction in the $CF_4$ concentration was analyzed in the same manner as in section (2), except that E. coli_dhlA was used and $CF_4$ was added at a headspace concentration of 600 ppm.

Figure 2A:
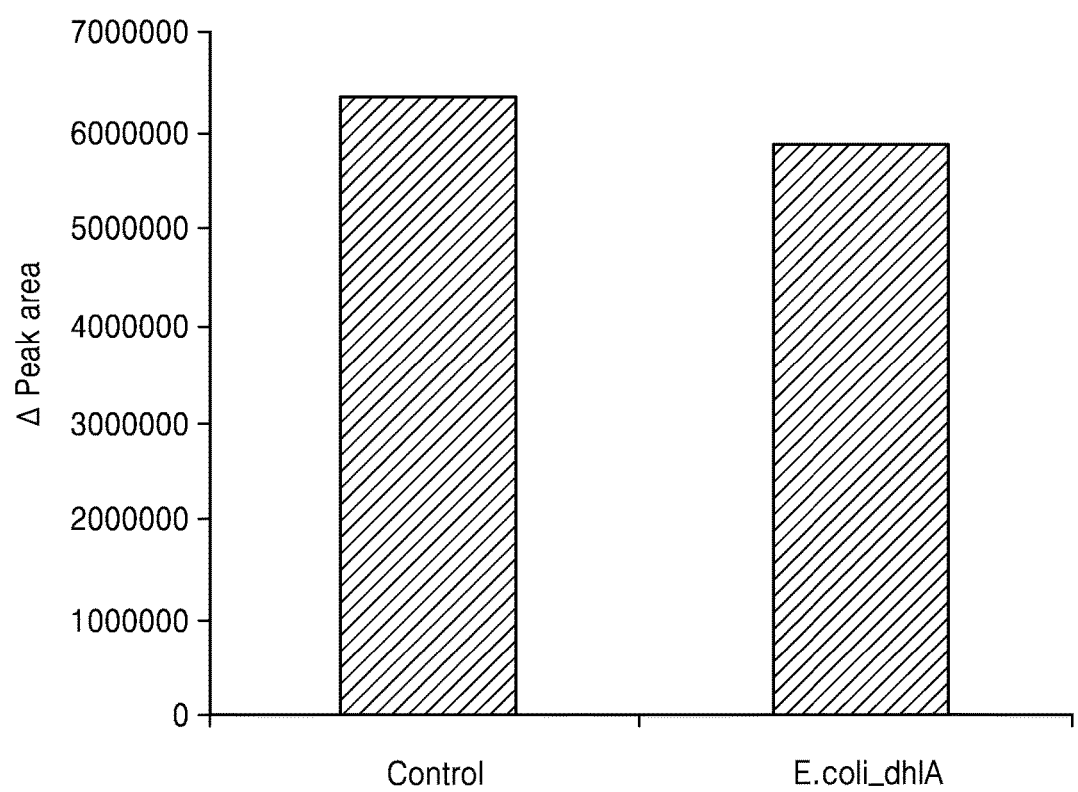
FIG. 2A shows the experimental result of decomposing perfluoromethane by haloalkane dehalogenase-introduced E. coli.

FIG. 2A shows the experimental result of decomposing perfluoromethane by haloalkane dehalogenase-introduced E. coli. As shown in FIG. 2A, E. coli_dhlA showed 7.6% reduction in the amount of perfluoromethane, compared to the control group. This result of FIG. 2A indicates that haloalkane dehalogenase-introduced E. coli has a perfluoromethane decomposition ability.

Further, E. coli BL21 star/pMALc2-CfrA prepared in section (1) was inoculated in a medium in a shaking incubator, and incubated in the presence of 0.2 mM IPTG and 1 µM cobalamin cofactor at 20° C. for 20 hours to induce expression of the CfrA gene. A cell pellet was obtained from a culture, and lysed in PBS buffer (Sigma-Aldrich Inc.) as a lysis solution to obtain a lysate. A crude extract was obtained from the lysate. Next, 2 mM Ti(III)-NTA, 2 mM methylviologen and 5 ml of the crude extract were added to a serum bottle, and $CF_4$ was added at a headspace concentration of 1,000 ppm. The bottle was sealed and incubated at 30° C. for a predetermined time. A negative control (NC) was prepared in the same manner, except that E. coli BL21 star was used. As a result, 12% $CF_4$ was finally decomposed. A specific activity of the cell was 0.0044 unit/g-cell. Analysis of $CF_4$ was the same as described above.

Figure 2B:
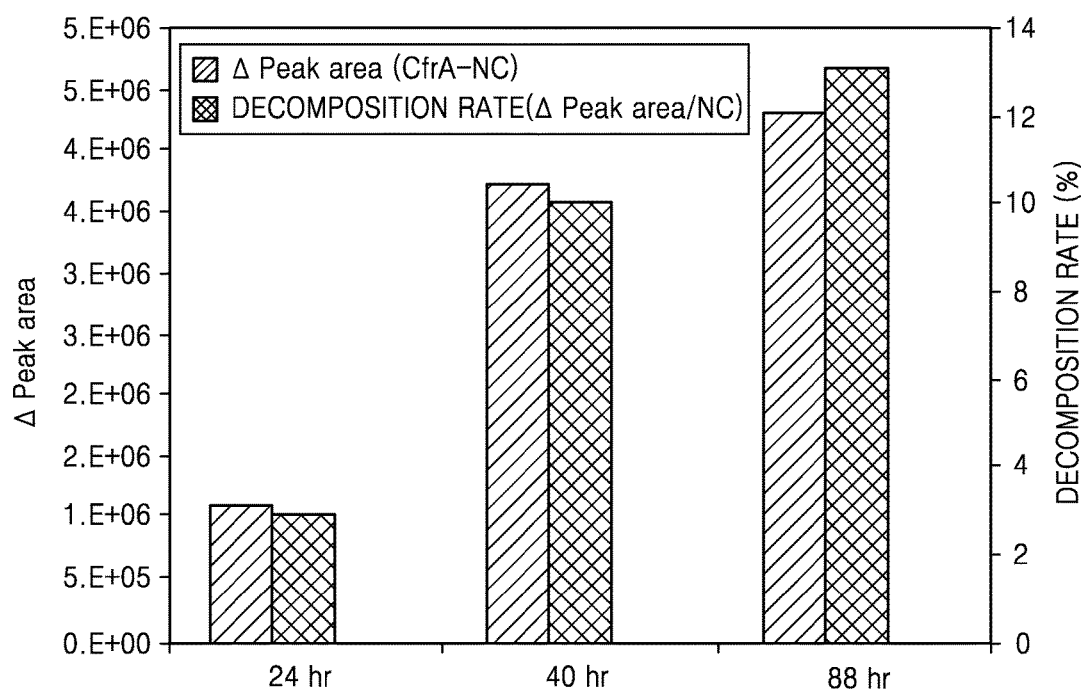
FIG. 2B shows changes in a concentration of $CF_4$ in a sample by E. coli BL21 star/pMALc2-CfrA, normalized using a negative control value, in which Δpeak area represents CfrA area-negative control area, and decomposition rate (%) represents (Δpeak area/negative control)×100.

FIG. 2B shows changes in the $CF_4$ concentration in the sample by E. coli BL21 star/pMALc2-CfrA, which were normalized using a negative control value. In FIG. 2B, Δpeak area represents CfrA area-negative control area, and decomposition rate represents Δpeak area/negative control value.

Example 2: Recombinant E. coli Expressing $P450_{CAM}$ Gene and Removal of Halomethane from Sample by Using the Same In this Example, a recombinant E. coli expressing a $P450_{CAM}$ gene was prepared, and an effect of removing halomethane, i.e., $CHF_3$, $CF_4$ or $CHCl_3$ in a sample by using the same was examined.

(1) Preparation of Recombinant E. coli Expressing $P450_{CAM}$ Gene

As $P450_{CAM}$ genes, camC, camA, and camB genes were amplified from CAM plasmid of Pseudomonas putida PpG786 strain, respectively. camC, camA, and camB genes have nucleotide sequences of SEQ ID NOS: 40, 36, and 38, and encode amino acid sequences of SEQ ID NOS: 41, 37, and 39. In detail, P. putida PpG786 strain DSM 7162 was cultured in an LB medium at 30° C. under stirring at 230 rpm overnight, and then CAM plasmid was isolated using a total DNA extraction kit (Invitrogen Biotechnology). PCR was performed using the CAM plasmid as a template and a set of primers having nucleotide sequences of SEQ ID NOS: 46 and 47; a set of primers having nucleotide sequences of SEQ ID NOS: 48 and 49; and a set of primers having nucleotide sequences of SEQ ID NOS: 50 and 51 to amplify and obtain camA, camB, and camC genes, respectively.

The camC gene which was amplified by PCR using a set of primers of nucleotide sequences of SEQ ID NOS: 46 and 47 was ligated with pETDuet (Novagen, Cat. No. 71146-3), which was digested with restriction enzymes, NcoI and HindIII, using an InFusion Cloning Kit (Clontech Laboratories, Inc.) to prepare a pETDuet-camC vector. Further, the prepared pETDuet-camC vector was digested with restriction enzymes, NdeI and XhoI, and ligated with the amplified camA and camB gene fragments using the InFusion Cloning Kit (Clontech Laboratories, Inc.) to prepare a pETDuet-camC-camAB vector.

Figure 3:
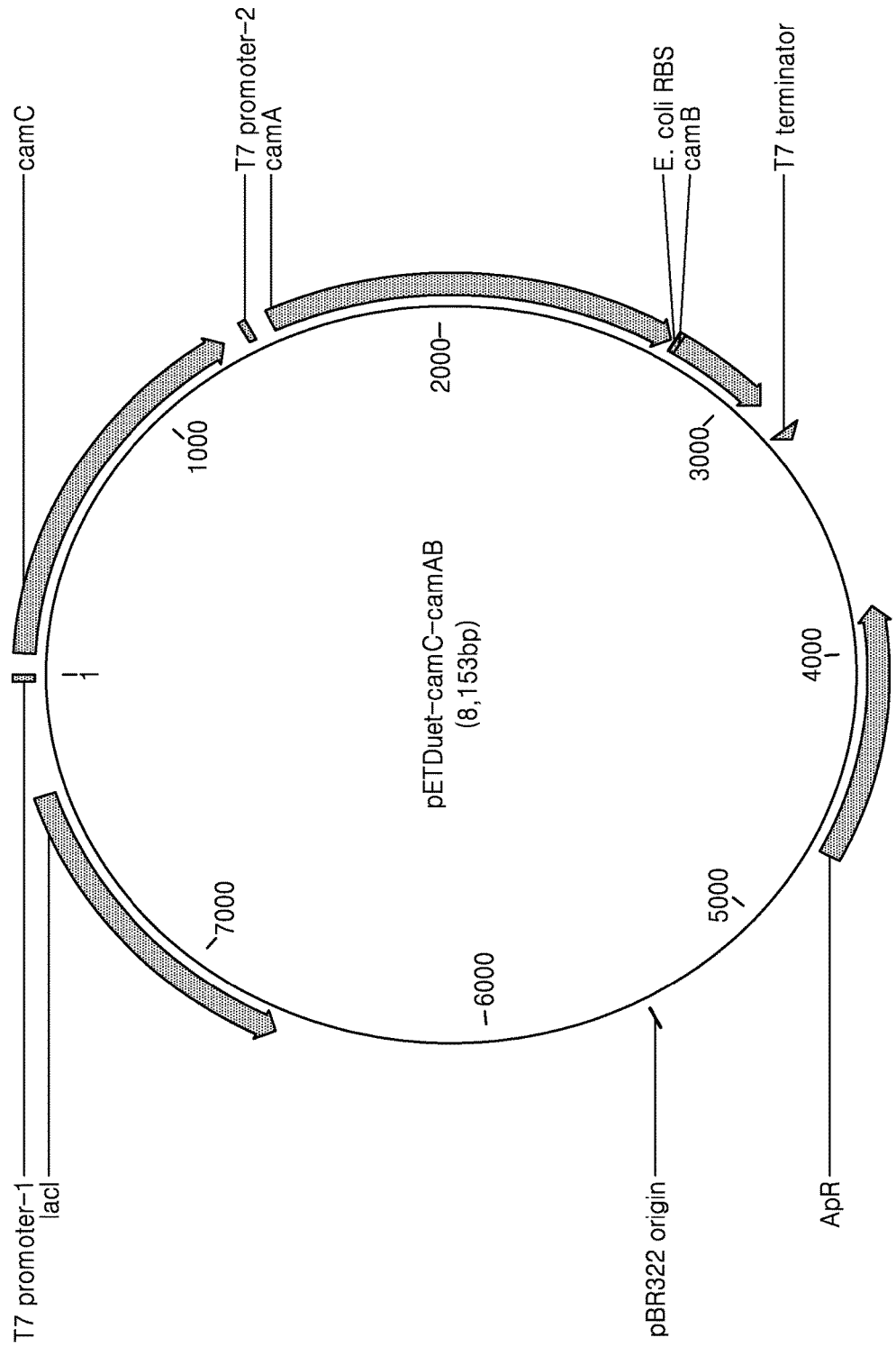
FIG. 3 shows a vector map of a pETDuet-camC-camAB vector.

FIG. 3 shows a vector map of the pETDuet-camC-camAB vector.

Next, E. coli BL21 strain was introduced with the prepared pETDuet-camC-camAB vector by a heat shock method (Sambrook, J & Russell, D. W., New York: Cold Spring Harbor Laboratory Press, 2001), and then cultured on a LB plate containing ampicillin (100 µg/mL). A strain showing ampicillin resistance was selected. Finally, the strain thus selected was designated as a recombinant E. coli BL21/pETDuet-camC-camAB.

(2) Effect of Removing $CHF_3$ or $CHCl_3$ from Sample by Recombinant E. coli Expressing $P450_{CAM}$ Gene In this section, it was examined whether the $P450_{CAM}$ gene-introduced, E. coli BL21/pETDuet-camC-camAB strain prepared in section (1) affects removal of $CHF_3$ or $CHCl_3$ from a sample. In detail, E. coli BL21/pETDuet-camC-camAB was cultured in a Terrific Broth (TB) medium at 30° C. under stirring at 230 rpm. At $OD_{600}$ of about 0.5, 0.5 mM of IPTG was added thereto, followed by culturing at 25° C. under stirring 230 rpm overnight. The cells were harvested and suspended in an M9 medium to a cell density of $OD_{600}$ of 2.5. 10 ml of this cell suspension was added to a 60 ml-serum bottle, and then the bottle was sealed. The TB medium included 12 g of tryptone, 24 g of yeast extract, 5 g of glycerol, and 89 mM phosphate buffer per 1 L of distilled water.

Next, gas-phase $CHF_3$ was injected through a rubber stopper of a cap of the serum bottle using a syringe to its headspace concentration of 200 ppm. Further, liquid-phase $CHCl_3$ was injected through the rubber stopper of the cap of the serum bottle using the syringe to its concentration of 0.02 mM in the medium. Thereafter, the serum bottle was incubated for 18 hrs to 152 hrs, while stirring at 30° C. and 200 rpm. Each experiment was performed in triplicate. At a predetermined time, a headspace gas was analyzed.

Figure 4:
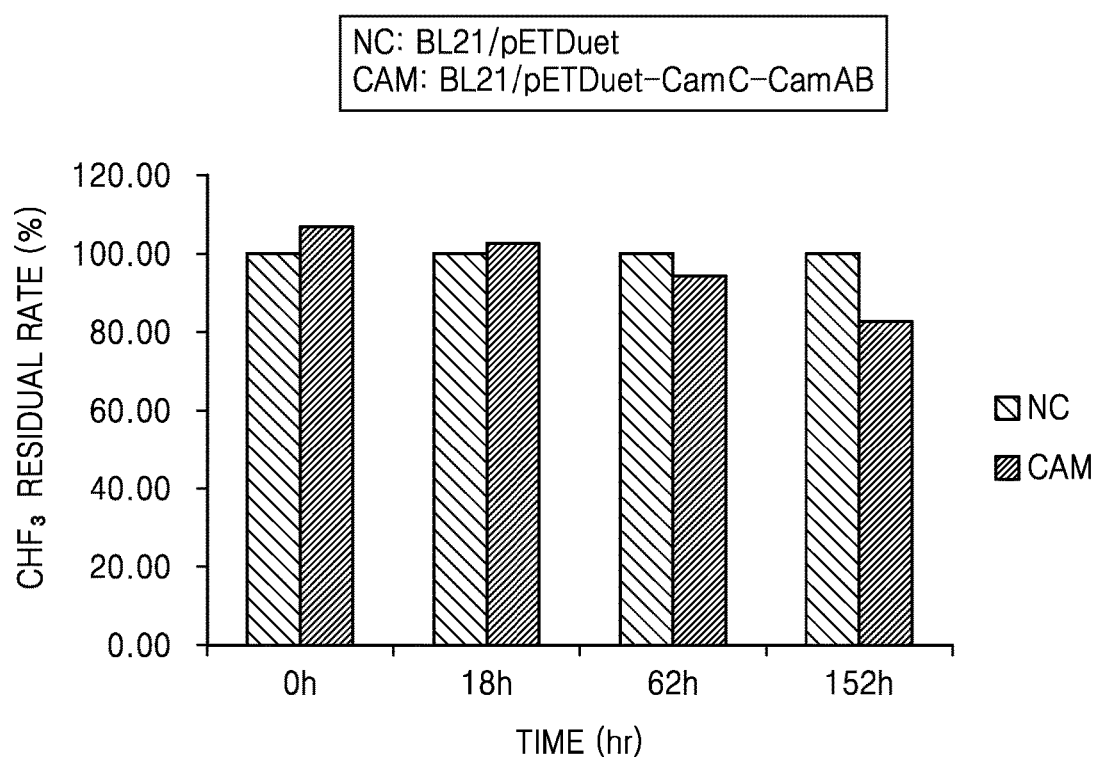
FIG. 4 shows changes in a headspace concentration of $CHF_3$ over time when *E. coli* BL21/pETDuet-camC-camAB was cultured in a medium contacted with $CHF_3$-containing gas.

FIG. 4 shows changes in a headspace concentration of $CHF_3$ over time when E. coli BL21/pETDuet-camC-camAB was cultured in the medium contacted with $CHF_3$-containing gas.

Figure 5A:
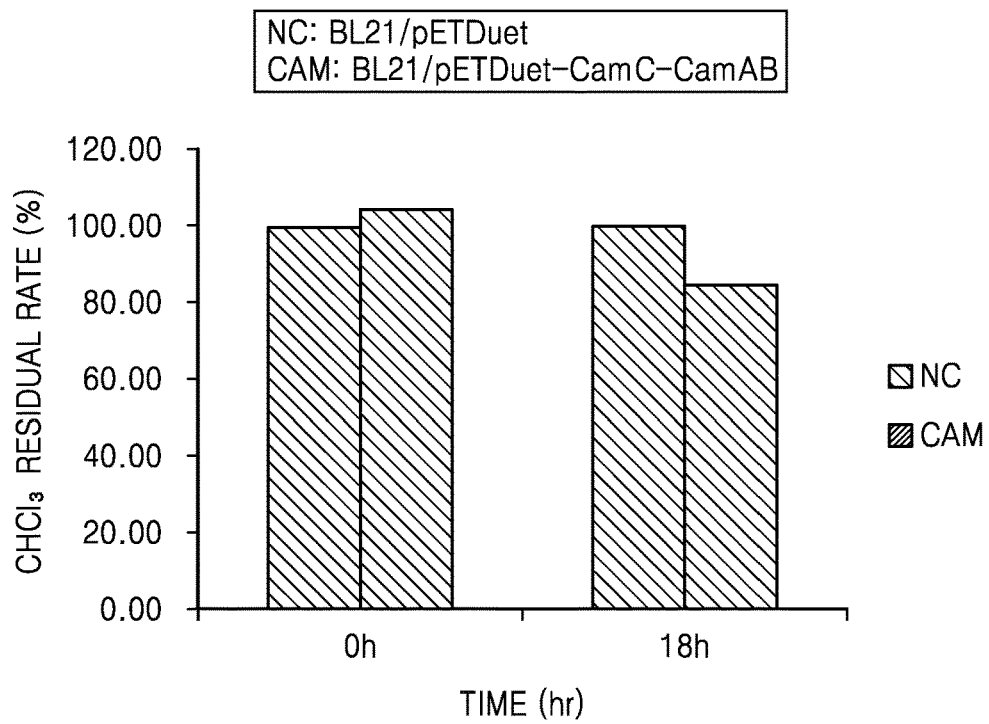
FIG. 5A shows changes in a headspace concentration of $CHCl_3$ over time when *E. coli* BL21/pETDuet-camC-camAB was cultured in a $CHCl_3$-containing medium.
Figure 5B:
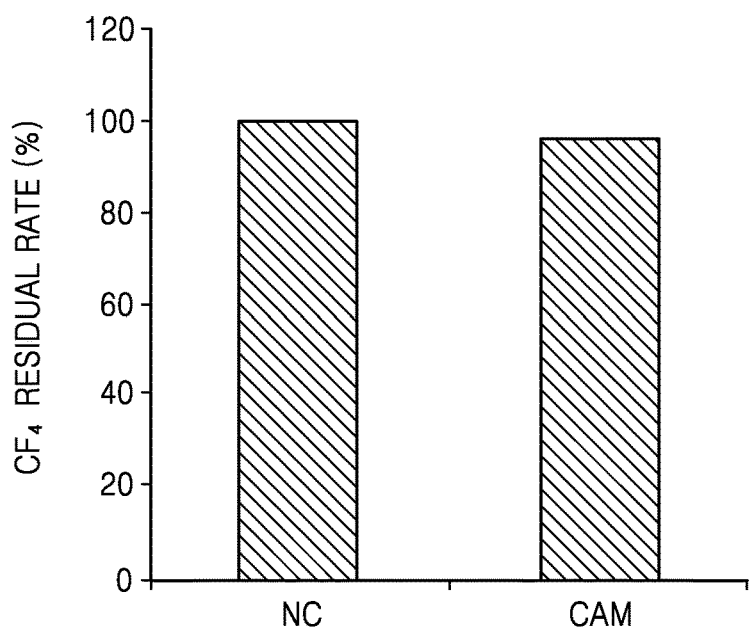
FIG. 5B shows changes in a headspace concentration of $CF_4$ over time when *E. coli* BL21/pETDuet-camC-camAB was cultured in a medium contacted with $CF_4$-containing gas.

FIG. 5A shows changes in a headspace concentration of $CHCl_3$ over time when *E. coli* BL21/pETDuet-camC-camAB was cultured in a $CHCl_3$-containing medium. In FIGS. 4, 5A, and 5B, NC represents a negative control group, and 'CAM' represents an experiment performed by using *E. coli* BL21/pETDuet-camC-camAB. As shown in FIG. 4, when the *E. coli* BL21/pETDuet-camC-camAB was cultured for 62 hours and 152 hours, the headspace concentration of $CHF_3$ was decreased by about 5.62% and about 17.3%, compared to the control group. Further, as shown in FIG. 5A, when the *E. coli* BL21/pETDuet-camC-camAB was cultured for 18 hours, the headspace concentration of $CHCl_3$ was decreased by about 14.8%, compared to the control group.

(3) Effect of Removing $CF_4$ in Sample by Recombinant *E. coli* Expressing $P450_{CAM}$ Gene In this section, it was examined whether the $P450_{CAM}$ gene-introduced, *E. coli* BL21/pETDuet-camC-camAB strain prepared in section (1) affects removal of $CF_4$ in a sample.

Experiments were performed in the same manner as in the method performed for $CHF_3$ in section (2), except that $CF_4$ was used instead of $CHF_3$, and gas-phase $CF_4$ was injected through a rubber stopper of a cap of the serum bottle using a syringe to its headspace concentration of 1000 ppm. Thereafter, experiment was performed in the same manner, except that the serum bottle was incubated for 7 days, while stirring at 30° C. and 200 rpm. The results are the same as in FIG. 5B.

FIG. 5B shows changes in a headspace concentration of $CF_4$ over time when *E. coli* BL21/pETDuet-camC-camAB was cultured in the medium contacted with $CF_4$-containing gas. As shown in FIG. 5B, when the *E. coli* BL21/pETDuet-camC-camAB was cultured for 7 days, the headspace concentration of $CF_4$ was decreased by about 3.57%, compared to the control group.

Example 3: Recombinant *E. coli* Expressing $P450_{BM3}$ Gene and Removal of Halomethane in Sample by Using the Same In this Example, a recombinant *E. coli* expressing a $P450_{BM3}$ gene was prepared, and an effect of removing halomethane, i.e., $CHF_3$, $CF_4$ or $CHCl_3$ in a sample by using the same was examined.

Figure 6:
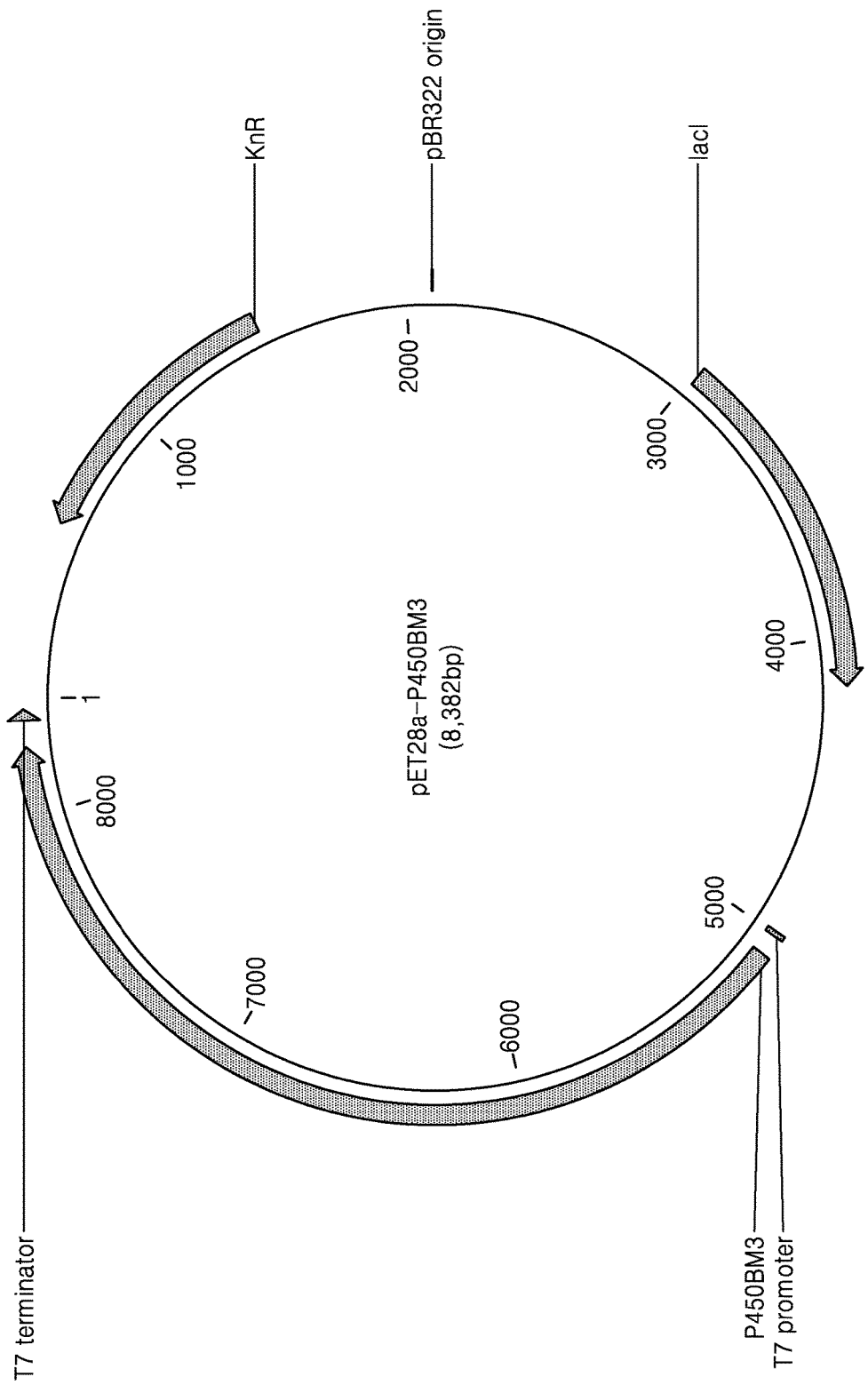
FIG. 6 shows a vector map of a pET28a-P450$_{BM3}$ vector.

(1) Preparation of Recombinant *E. coli* Expressing $P450_{BM3}$ Gene $P450_{BM3}$ gene of *Bacillus megaterium* (ATCC 14581) strain was amplified. $P450_{BM3}$ gene has a nucleotide sequence of SEQ ID NO: 42, and encodes an amino acid sequence of SEQ ID NO: 43. In detail, *B. megaterium* (ATCC 14581) was cultured in an LB medium at 30° C. under stirring at 230 rpm overnight, and then a genomic DNA was isolated using the total DNA extraction kit (Invitrogen Biotechnology). PCR was performed using this genomic DNA as a template and a set of primers having nucleotide sequences of SEQ ID NOS: 52 and 53 to amplify and obtain the $P450_{BM3}$ gene. The $P450_{BM3}$ gene thus amplified was ligated with pET28a (Novagen, Cat. No. 69864-3), which was digested with restriction enzymes, NcoI and XhoI, using the InFusion Cloning Kit (Clontech Laboratories, Inc.) to prepare a pET28a-$P450_{BM3}$ vector. FIG. 6 shows a vector map of the pET28a-$P450_{BM3}$ vector.

Figure 7:
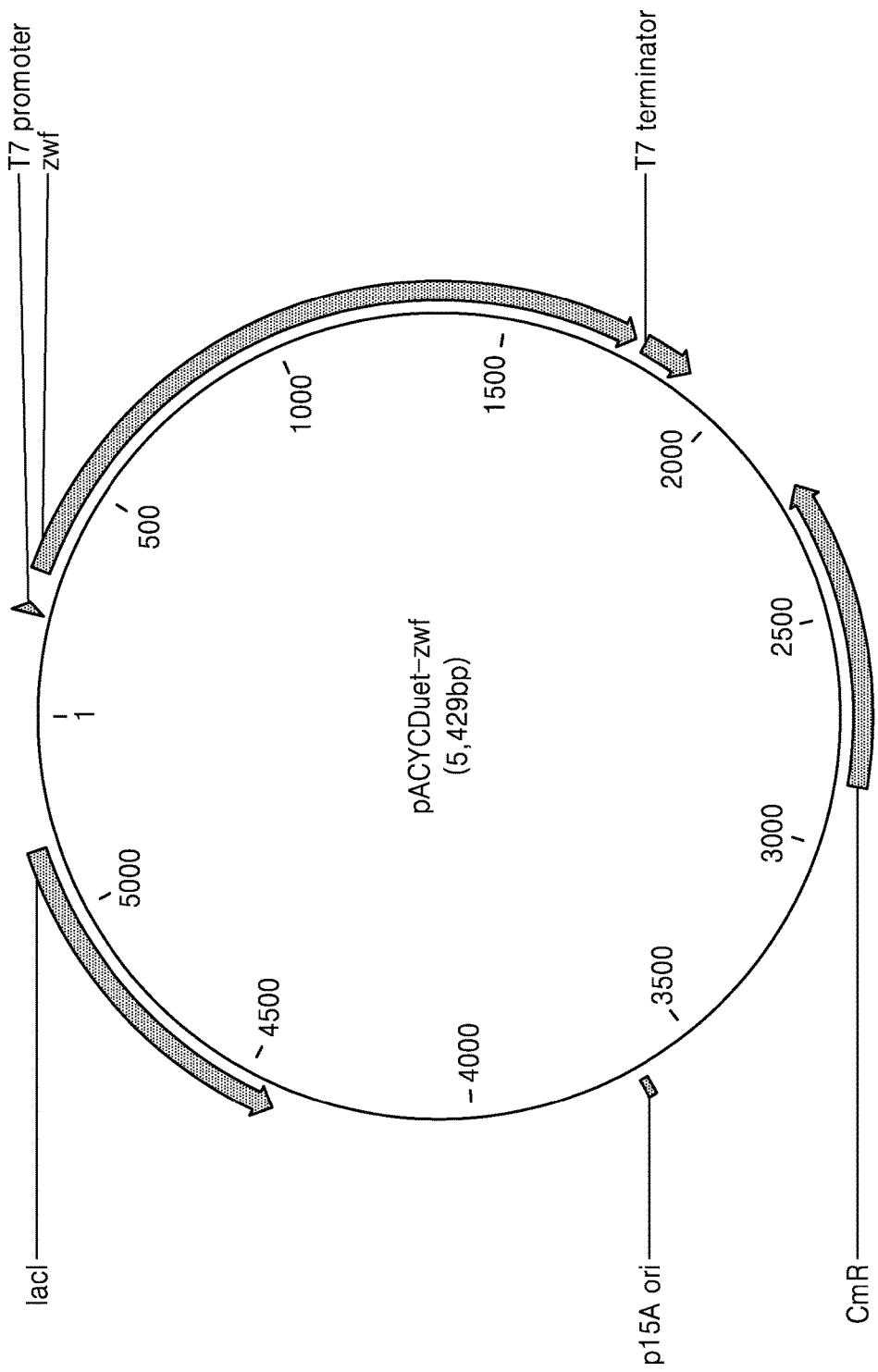
FIG. 7 shows a vector map of a pACYCDuet-zwf vector.

Further, in order to increase an intracellular NADPH level, zwf gene encoding glucose 6-phosphate dehydrogenase of *E. coli* K12 (MG1655) was amplified. The Zwf gene has a nucleotide sequence of SEQ ID NO: 44, and encodes an amino acid sequence of SEQ ID NO: 45. In detail, *E. coli* was cultured in an LB medium at 37° C. under stirring at 230 rpm overnight, and then a genomic DNA was isolated using the total DNA extraction kit (Invitrogen Biotechnology). PCR was performed using this genomic DNA as a template and a set of primers having nucleotide sequences of SEQ ID NOS: 54 and 55 to amplify and obtain the zwf gene. The zwf gene thus amplified was ligated with pACYCDuet (Novagen, Cat. No. 71147-3), which was digested with restriction enzymes, NcoI and SacI, using the InFusion Cloning Kit (Clontech Laboratories, Inc.) to prepare a pACYCDuet-zwf vector. FIG. 7 shows a vector map of the pACYCDuet-zwf vector.

Next, *E. coli* BL21 strain was introduced with the prepared pET28a-$P450_{BM3}$ vector by a heat shock method, and then cultured on a LB plate containing kanamycin (50 µg/mL). A strain showing kanamycin resistance was selected. Finally, the strain thus selected was designated as a recombinant *E. coli* BL21/pET28a-$P450_{BM3}$.

Further, *E. coli* BL21 strain was introduced with the prepared pET28a-$P450_{BM3}$ vector and pACYCDuet-zwf vector by a heat shock method, and then cultured on a LB plate containing kanamycin (50 µg/mL) and chloramphenicol (35 µg/mL). A strain showing kanamycin resistance and chloramphenicol resistance was selected. Finally, the strain thus selected was designated as a recombinant *E. coli* BL21/pET28a-$P450_{BM3}$+pACYCDuet-zwf.

(2) Effect of Removing $CHF_3$ or $CHCl_3$ in Sample by Recombinant *E. coli* Expressing $P450_{BM3}$ Gene In this section, it was examined whether the $P450_{BM3}$ gene-introduced, recombinant *E. coli* BL21/pET28a-$P450_{BM3}$ strain or BL21/pET28a-$P450_{BM3}$+pACYCDuet-zwf strain prepared in section (1) affects removal of $CHF_3$ or $CHCl_3$ in a sample.

In detail, *E. coli* BL21/pET28a-$P450_{BM3}$ or BL21/pET28a-$P450_{BM3}$+pACYCDuet-zwf strain was cultured in the TB medium at 30° C. under stirring at 230 rpm. At $OD_{600}$ of about 0.5, 0.2 mM of IPTG was added thereto, followed by culturing at 25° C. and 230 rpm overnight. The cells were harvested and suspended in the M9 medium to a cell density of $OD_{600}$ of 2.5. 10 ml of this cell suspension was added to a 60 ml-serum bottle, and then the bottle was sealed. The TB medium and the M9 medium are the same as those described in Example 2.

Next, gas-phase $CHF_3$ was injected through a rubber stopper of a cap of the serum bottle using a syringe to its headspace concentration of 200 ppm. Further, liquid-phase $CHCl_3$ was injected through the rubber stopper of the cap of the serum bottle using the syringe to its concentration of 0.02 mM in the medium. Thereafter, the serum bottle was incubated for 15 hrs to 142 hrs, while stirring at 30° C. and 230 rpm. Each experiment was performed in triplicate.

A headspace concentration of $CHF_3$ or $CHC_{l3}$ in the serum bottle was analyzed at a predetermined time interval during culture under the same conditions as in (2) of Example 2.

Figure 8:
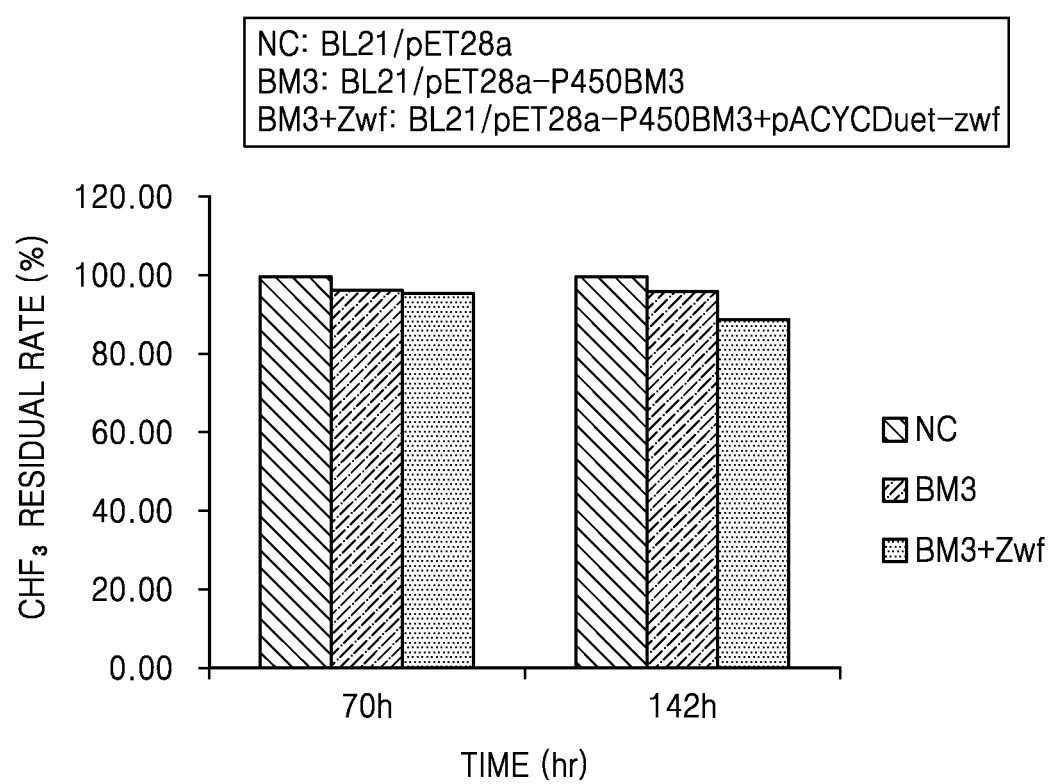
FIG. 8 shows changes in a headspace concentration of $CHF_3$ over time when *E. coli* BL21/pET28a-P450$_{BM3}$ or BL21/pET28a-P450$_{BM3}$+pACYCDuet-zwf strain was cultured in a solution contacted with $CHF_3$-containing gas.

FIG. 8 shows changes in a headspace concentration of $CHF_3$ over time when *E. coli* BL21/pET28a-$P450_{BM3}$ or BL21/pET28a-$P450_{BM3}$+pACYCDuet-zwf strain was cultured in the medium contacted with $CHF_3$-containing gas for 142 hours.

Figure 9A:
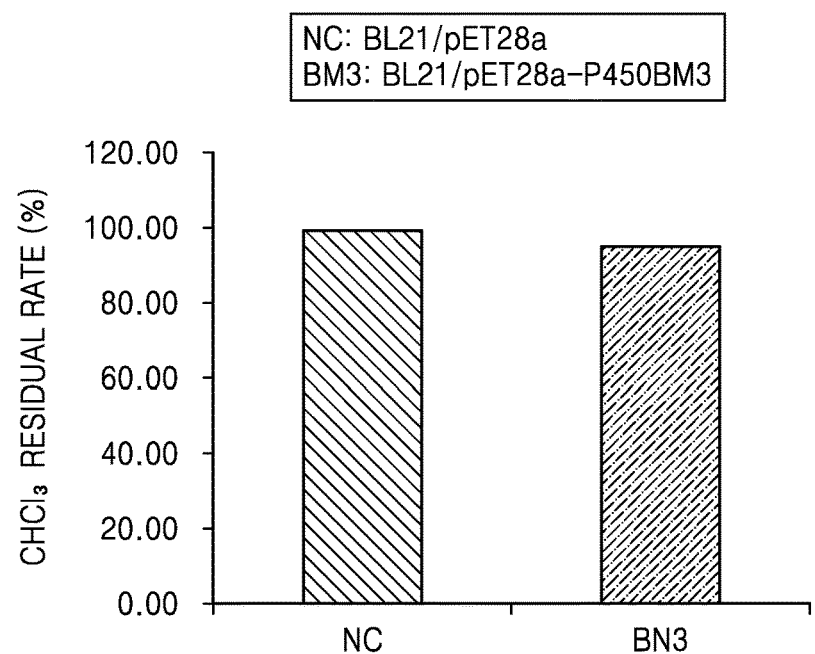
FIG. 9A shows changes in a headspace concentration of $CHCl_3$ over time when *E. coli* BL21/pET28a-P450$_{BM3}$ was cultured in a $CHCl_3$-containing medium.
Figure 9B:
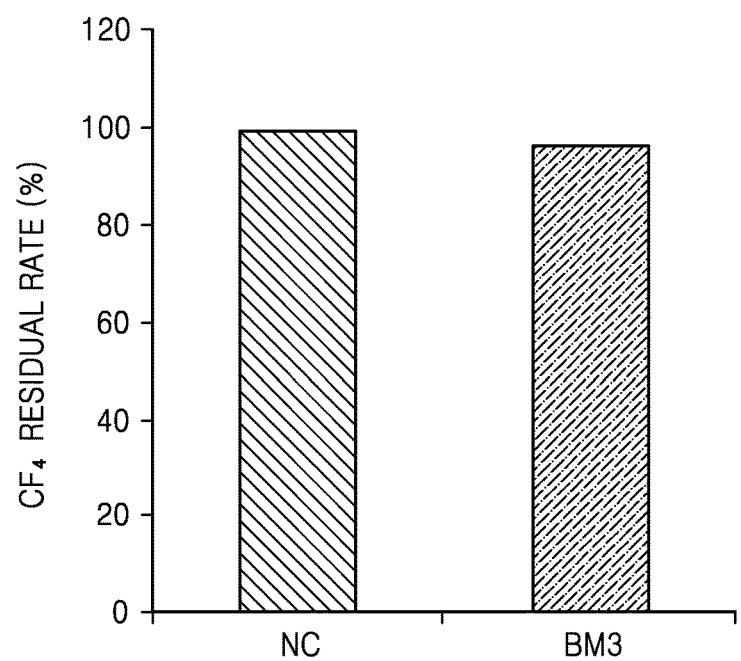
FIG. 9B shows changes in a headspace concentration of $CF_4$ over time when *E. coli* BL21/pET28a-P450$_{BM3}$ was cultured for 7 days in a medium contacted with $CF_4$-containing gas.

FIG. 9A shows changes in a headspace concentration of $CHCl_3$ when *E. coli* BL21/pET28a-$P450_{BM3}$ was cultured in a $CHCl_3$-containing medium for 15 hours. In FIGS. 8, 9A, and 9B, NC represents a negative control group, '13M3' represents an experiment performed by using *E. coli* BL21/pET28a-$P450_{BM3}$, and '13M3+Zwf' represents an experiment performed by using E. coli BL21/pET28a-P450$_{BM3}$+ pACYCDuet-zwf. As shown in FIG. 8, when the E. coli BL21/pET28a-P450$_{BM3}$ and E. coli BL21/pET28a-P450$_{BM3}$+pACYCDuet-zwf were cultured for 70 hours and 142 hours, the headspace concentration of CHF$_3$ was decreased by about 3.93% and 4.57% for 70 hours and about 4.15% and 11.03% for 142 hours, respectively, compared to the control group. Further, as shown in FIG. 9A, when they were cultured for 15 hours, the headspace concentration of CHCl$_3$ was decreased by about 4.1%, compared to the control group.

(3) Effect of Removing CF$_4$ in Sample by Recombinant E. coli Expressing P450$_{BM3}$ Gene In this section, it was examined whether the P450$_{BM3}$ gene-introduced, recombinant E. coli BL21/pET28a-P450$_{BM3}$ strain prepared in section (1) affects removal of CF$_4$ in a sample.

Experiments were performed in the same manner as in the method performed for CHF$_3$ in section (2), except that CF$_4$ was used instead of CHF$_3$, and gas-phase CF$_4$ was injected through a rubber stopper of a cap of the serum bottle using a syringe to its headspace concentration of 1000 ppm. Thereafter, experiment was performed in the same manner, except that the serum bottle was incubated for 7 days, while stirring at 30° C. and 200 rpm. The results are the same as in FIG. 9B.

FIG. 9B shows changes in a headspace concentration of CF$_4$ over time when E. coli BL21/pET28a-P450$_{BM3}$ was cultured for 7 days in a medium contacted with CF$_4$-containing gas. As shown in FIG. 9B, when E. coli BL21/pET28a-P450$_{BM3}$ was cultured for 7 days, the headspace concentration of CF$_4$ was decreased by about 3.03%, compared to the control group.

Example 4: Recombinant E. coli Expressing sMMO Gene and Removal of Halomethane in Sample by Using the Same In this Example, a recombinant E. coli expressing sMMO gene was prepared, and an effect of removing halomethane, i.e., CHF$_3$ or CHC$_{13}$ in a sample by using the same was examined.

(1) Preparation of Recombinant E. coli Expressing sMMO Gene sMMO genes, i.e., mmoX, mmoY, mmoZ, mmoB, mmoC, mmoD, and mmoG genes were amplified from *Methylococcus capsulatus* (Bath) strain, respectively. mmoX, mmoY, mmoZ, mmoB, mmoC, mmoD, and mmoG genes have nucleotide sequences of SEQ ID NOS: 6, 8, 10, 12, 14, 16, and 18, and encodes amino acid sequences of SEQ ID NOS: 5, 7, 9, 11, 13, 15, and 17, respectively.

Figure 10A:
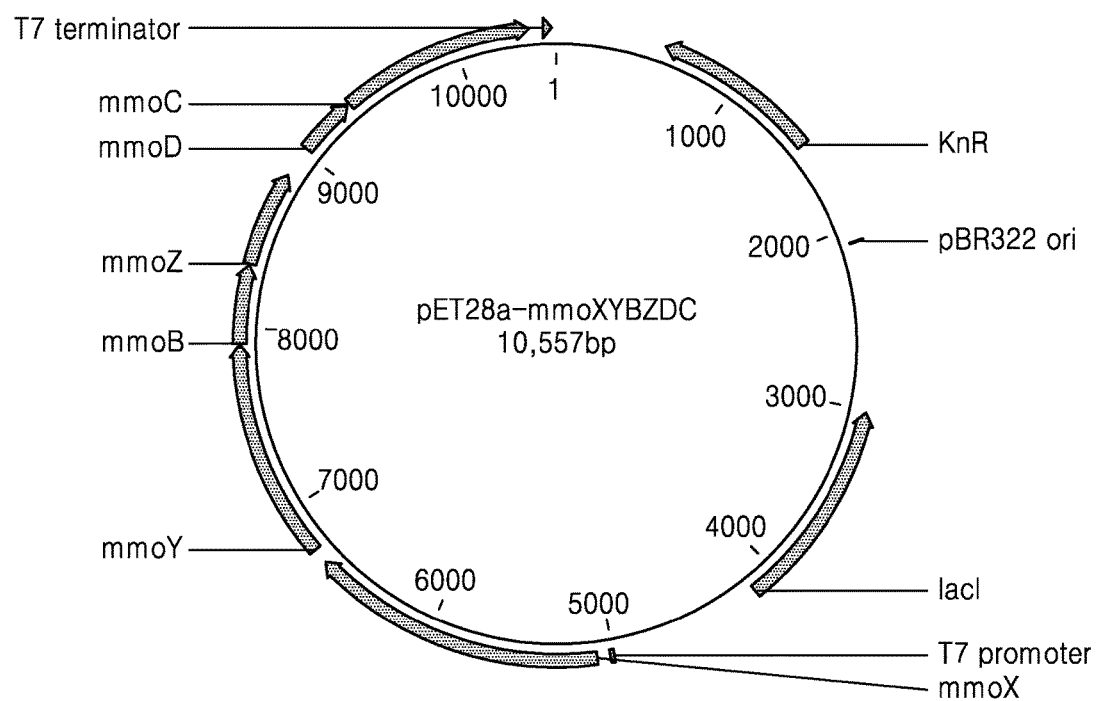
FIG. 10A shows a vector map of a pET28a-mmoXY-BZDC vector.

In detail, PCR was performed using chromosomal DNA of *Methylococcus capsulatus* (Bath) strain (ATCC 33009D-5) as a template and a set of primers having nucleotide sequences of SEQ ID NOS: 19 and 20 to amplify a region of SEQ ID NO: 35, which includes all of the mmoX, mmoY, mmoZ, mmoB, mmoC, and mmoD genes. An amplified gene fragment was ligated with pET28a (Novagen, Cat. No. 69864-3) digested with restriction enzymes, NcoI and XhoI using an InFusion Cloning Kit (Clontech Laboratories, Inc.) to prepare a pET28a-mmoXYBZDC vector. FIG. 10A shows a vector map of the pET28a-mmoXYBZDC vector.

Figure 10B:
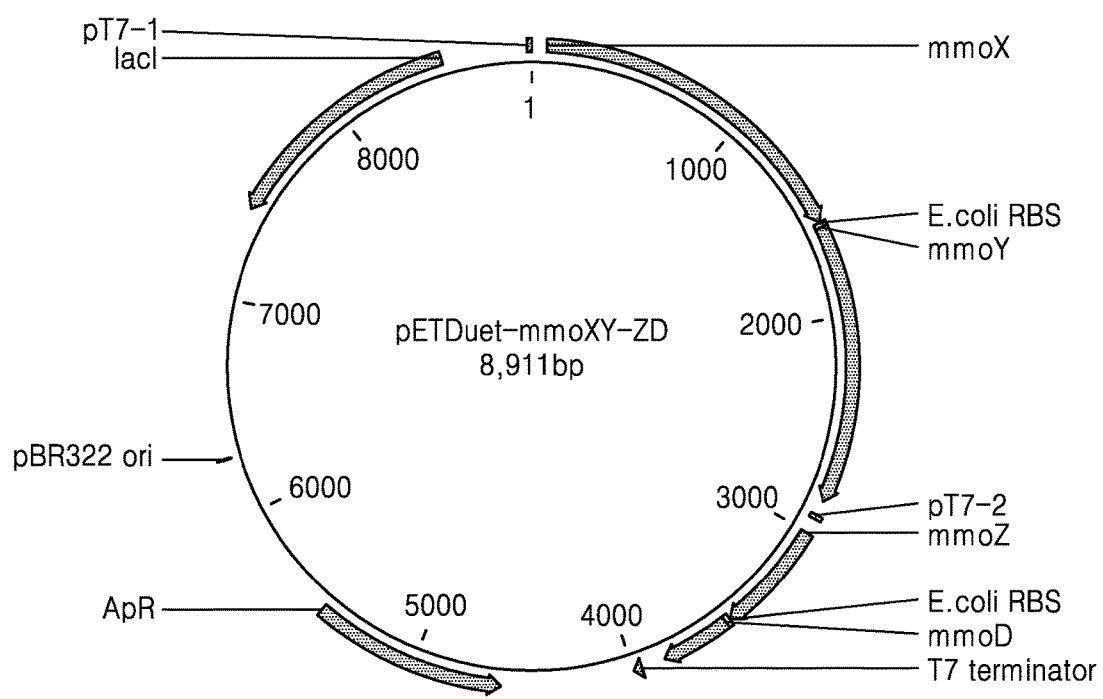
FIG. 10B shows a vector map of a pETDuet-mmoXY-ZD vector.

Further, to express the sMMO gene using E. coli ribosome binding site (RBS), mmoX, mmoY, mmoZ, mmoB, mmoC, and mmoD were amplified, respectively and then inserted into an expression vector. A region including the mmoX and mmoY genes was amplified using an mmoX gene fragment which was amplified by PCR using a set of primers of nucleotide sequences of SEQ ID NOS: 21 and 22 and an mmoY gene fragment which was amplified by PCR using a set of primers of nucleotide sequences of SEQ ID NOS: 23 and 24 as templates, and a set of primers of nucleotide sequences of SEQ ID NOS: 21 and 24. A gene fragment thus amplified was ligated with pETDuet (Novagen, Cat. No. 71146-3) which was digested with restriction enzymes NcoI and HindIII, using an InFusion Cloning Kit (Clontech Laboratories, Inc.) to prepare a pETDuet-mmoXY vector. Further, a region including the mmoZ and mmoD genes was amplified using an mmoZ gene fragment which was amplified by PCR using a set of primers of nucleotide sequences of SEQ ID NOS: 25 and 26 and an mmoD gene fragment which was amplified by PCR using a set of primers of nucleotide sequences of SEQ ID NOS: 27 and 28 as templates, and a set of primers of nucleotide sequences of SEQ ID NOS: 25 and 26. A gene fragment thus amplified was ligated with pETDuet-mmoXY, which was digested with restriction enzymes NdeI and XhoI, using the InFusion Cloning Kit (Clontech Laboratories, Inc.) to prepare a pETDuet-mmoXY-ZD vector. FIG. 10B shows a vector map of the pETDuet-mmoXY-ZD vector.

Figure 10C:
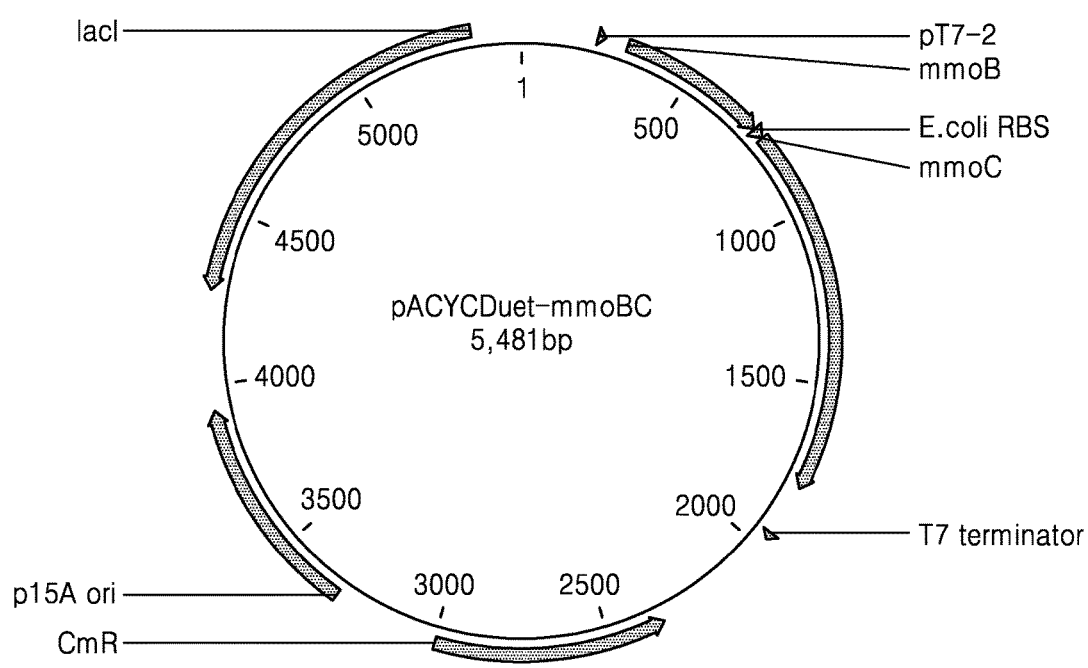
FIG. 10C shows a vector map of a pACYCDuet-mmoBC vector.

A region including the mmoB and mmoC genes was amplified using an mmoB gene fragment which was amplified by PCR using a set of primers of nucleotide sequences of SEQ ID NOS: 29 and 30 and an mmoC gene fragment which was amplified by PCR using a set of primers of nucleotide sequences of SEQ ID NOS: 31 and 32 as templates, and a set of primers of nucleotide sequences of SEQ ID NOS: 29 and 32. A gene fragment thus amplified was ligated with pACYCDuet (Novagen, Cat. No. 71147-3), which was digested with restriction enzymes NdeI and EcoRV, using the InFusion Cloning Kit (Clontech Laboratories, Inc.) to prepare a pACYCDuet-mmoBC vector. FIG. 10C shows a vector map of the pACYCDuet-mmoBC vector.

Figure 10D:
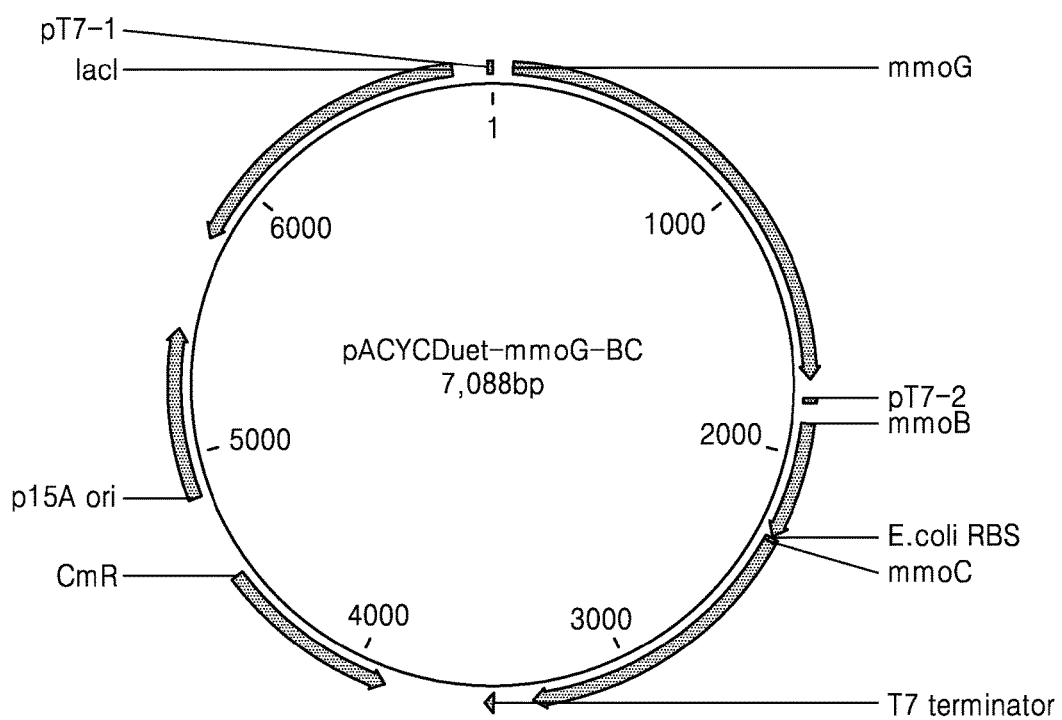
FIG. 10D shows a vector map of a pACYCDuet-mmoG-BC vector.

An mmoG gene fragment which was amplified by PCR using a set of primers of nucleotide sequences of SEQ ID NOS: 33 and 34 was ligated with pACYCDuet (Novagen, Cat. No. 71147-3), which was digested with restriction enzymes NcoI and HindIII, using the InFusion Cloning Kit (Clontech Laboratories, Inc.) to prepare a pACYCDuet-mmoG vector. Further, a region including the mmoB and mmoC genes was amplified using the mmoB gene fragment which was amplified by PCR using a set of primers of nucleotide sequences of SEQ ID NOS: 29 and 30 and the mmoC gene fragment which was amplified by PCR using a set of primers of nucleotide sequences of SEQ ID NOS: 31 and 32 as templates, and a set of primers of nucleotide sequences of SEQ ID NOS: 29 and 32. A gene fragment thus amplified was ligated with pACYCDuet-mmoG, which was digested with restriction enzymes NdeI and EcoRV, using the InFusion Cloning Kit (Clontech Laboratories, Inc.) to prepare a pACYCDuet-mmoG-BC vector. FIG. 10D shows a vector map of the pACYCDuet-mmoG-BC vector.

Next, E. coli BL21 strain was introduced with each of the prepared pETDuet-mmoXY-ZD vector and pACYCDuet-mmoBC vector, pETDuet-mmoXY-ZD and pACYCDuet-mmoG-BC vector, and pET28a-mmoXYBZDC vector by a heat shock method, respectively and then cultured on a LB plate containing 100 μg/mL of ampicillin and 35 μg/mL of chloramphenicol or 50 μg/mL of kanamycin. Strains showing ampicillin resistance and chloramphenicol or kanamycin resistance were selected. Finally, three kinds of strains thus selected were designated as recombinant E. coli BL21/ pETDuet-mmoXY-ZD+pACYCDuet-mmoBC, BL21/pET-Duet-mmoXY-ZD+pACYCDuet-mmoG-BC, and BL21/pET28a-mmoXYBZDC.

(2) Effect of Removing $CHF_3$ or $CHCl_3$ in Sample by Recombinant *E. coli* Expressing sMMO Gene In this section, it was examined whether the sMMO gene-introduced, recombinant *E. coli* BL21/pETDuet-mmoXY-ZD+pACYCDuet-mmoBC, BL21/pETDuet-mmoXY-ZD+pACYCDuet-mmoG-BC, and BL21/pET28a-mmoXYBZDC prepared in section (1) affect removal of $CHF_3$ or $CHCl_3$ in a sample. As a control group, *E. coli* BL21/pETDuet+pACYCDuet or BL21/pET28a introduced with an empty vector containing no sMMO gene was used.

In detail, each of the recombinant *E. coli* BL21/pETDuet-mmoXY-ZD+pACYCDuet-mmoBC, BL21/pETDuet-mmoXY-ZD+pACYCDuet-mmoG-BC, and BL21/pET28a-mmoXYBZDC was cultured in a Terrific Broth (TB) medium under stirring at 30° C. and 230 rpm. At $OD_{600}$ of about 0.5, 0.1 mM of IPTG and 0.1 mg/ml of ferric citrate, 0.1 mg/ml of ferrous sulfate, 0.1 mg/ml of ferric ammonium citrate, and 1 mM of cysteine were added thereto, followed by culturing at 25° C. and 230 rpm overnight. With respect to each recombinant *E. coli*, cells were harvested and suspended in an M9 medium containing 4 g/L of glucose to a cell density of $OD_{600}$ of 2.5. Each 10 ml of the cell suspensions was added to a 60 ml-serum bottle, and the bottles were sealed.

Next, in the case of $CHF_3$ reaction, gas-phase $CHF_3$ was injected through a rubber stopper of a cap of the serum bottle using a syringe to its headspace concentration of 1000 ppm. Further, in the case of $CHCl_3$ reaction, liquid-phase $CHCl_3$ was injected through the rubber stopper of the cap of the serum bottle using the syringe to its concentration of 0.02 mM in the medium. Thereafter, the serum bottle for $CHF_3$ reaction was incubated for 94 hours, and the serum bottle for $CHCl_3$ reaction was incubated for 25 hours, while stirring at 30° C. and 200 rpm. Each experiment was performed in triplicate.

After a predetermined time during incubation, a headspace concentration of $CHF_3$ or $CHCl_3$ in the serum bottle was analyzed under the same conditions as in (2) of Example 2.

Figure 11:
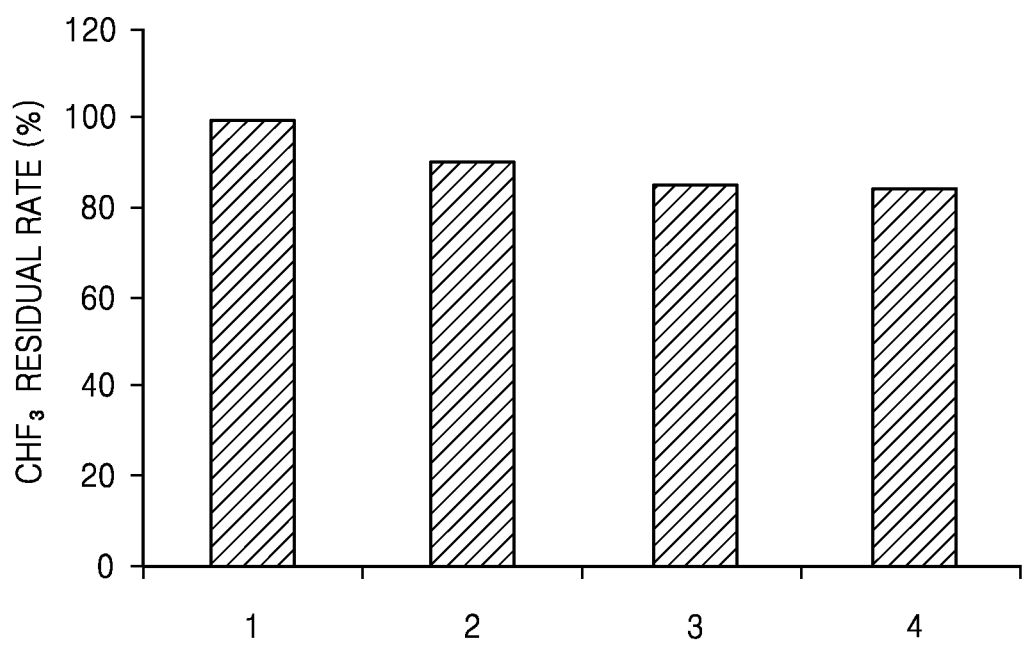
FIG. 11 shows changes in a headspace concentration of $CHF_3$ when recombinant *E. coli* was cultured in a medium contacted with $CHF_3$-containing gas.

FIG. 11 shows changes in a headspace concentration of $CHF_3$ when recombinant *E. coli* was cultured in the medium contacted with $CHF_3$-containing gas. In FIG. 11, 1 represents a control group, and 2 to 4 represent experiments which were performed using the recombinant *E. coli* BL21/pETDuet-mmoXY-ZD+pACYCDuet-mmoBC, BL21/pET-Duet-mmoXY-ZD+pACYCDuet-mmoG-BC, and BL21/pET28a-mmoXYBZDC, respectively. As shown in FIG. 11, when the recombinant *E. coli* BL21/pETDuet-mmoXY-ZD+pACYCDuet-mmoBC was cultured for 94 hours, the headspace concentration of $CHF_3$ was decreased by about 10%, compared to the control group. Further, when each of the recombinant *E. coli* BL21/pETDuet-mmoXY-ZD+pACYC-Duet-mmoG-BC and BL21/pET28a-mmoXYBZDC was cultured for 94 hours, the headspace concentration of $CHF_3$ was decreased by about 15%, compared to the control group.

Figure 12A:
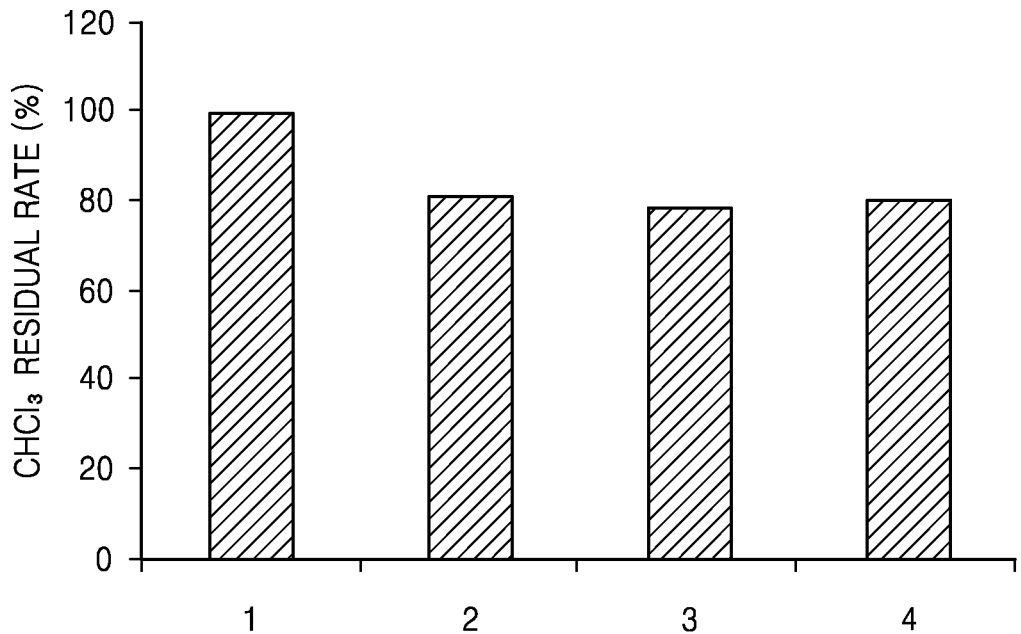
FIG. 12A shows changes in a headspace concentration of $CHCl_3$ when recombinant *E. coli* was cultured in a $CHCl_3$-containing medium.

FIG. 12A shows changes in a headspace concentration of $CHCl_3$ when recombinant *E. coli* was cultured in a $CHCl_3$-containing medium. In FIG. 12A, 1 to 4 are the same as described in FIG. 11. As shown in FIG. 12A, when each of the recombinant *E. coli* BL21/pETDuet-mmoXY-ZD+pA-CYCDuet-mmoBC and BL21/pETDuet-mmoXY-ZD+pA-CYCDuet-mmoG-BC was cultured for 25 hours, the headspace concentration of $CHCl_3$ was decreased by about 20%, compared to the control group. Further, when BL21/pET28a-mmoXYBZDC was cultured for 25 hours, the headspace concentration of $CHCl_3$ was also decreased by the level similar thereto.

(3) Effect of Removing $CF_4$ in Sample by Recombinant *E. coli* Expressing sMMO Gene In this Example, it was examined whether the sMMO gene-introduced, recombinant *E. coli* BL21/pET28a-mmoXYBZDC prepared in section (1) affects removal of $CF_4$ in a sample. As a control group, *E. coli* BL21/pET28a introduced with an empty vector containing no sMMO gene was used.

Experiments were performed in the same manner as in the method performed for $CHF_3$ in section (2), except that $CF_4$ was used instead of $CHF_3$, and gas-phase $CF_4$ was injected through a rubber stopper of a cap of the serum bottle using a syringe to its headspace concentration of 1000 ppm, and thereafter, the serum bottle was incubated for 7 days, while stirring at 30° C. and 200 rpm. The results are the same as in FIG. 12B.

Figure 12B:
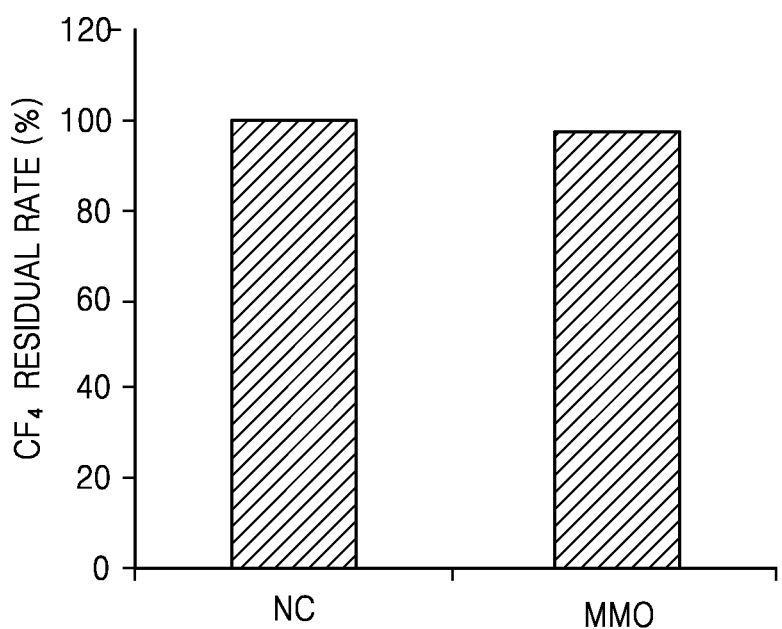
FIG. 12B shows changes in a headspace concentration of $CF_4$ when recombinant *E. coli* BL21/pET28a-mmoXY-BZDC was cultured for 7 days in a medium contacted with $CF_4$-containing gas.

FIG. 12B shows changes in a headspace concentration of $CF_4$ when recombinant *E. coli* BL21/pET28a-mmoXY-BZDC was cultured for 7 days in a medium contacted with $CF_4$-containing gas. In FIG. 12B, NC represents a negative control group and 'MMO' represents an experiment performed by using *E. coli* BL21/pET28a-mmoXYBZDC. As shown in FIG. 12B, when the recombinant *E. coli* BL21/pET28a-mmoXYBZDC was cultured for 7 days, the headspace concentration of $CF_4$ was decreased by about 3.42%, compared to the control group.

Example 5: Decomposition of Tetrafluoromethane by Dehalogenase-Introduced *Xanthobacter autotrophicus*

PCR was performed using a genomic sequence of *Xanthobacter autotrophicus* GJ10 purchased from German Collection of Microorganisms and Cell Cultures (DSMZ) as a template and a set of primers having nucleotide sequences of SEQ ID NOS: 58 and 59, and a dhlA gene (SEQ ID NO: 3) thus amplified was introduced into a pTSa vector using an In-Fusion HD Cloning Kit (Clontech) to prepare a pTSa_D-hlA vector (SEQ ID NO: 60) (ORF:2982-3914).

The vector thus prepared was transformed into *X. autotrophicus* GJ10 strain by electroporation, and a strain confirmed to have the dhlA gene was designated as Xantho_d-hlA. This strain was cultured in a 250 mL-plastic flask containing 50 mL of M9 medium at 30° C. under stirring at 230 rpm overnight.

Figure 13A:
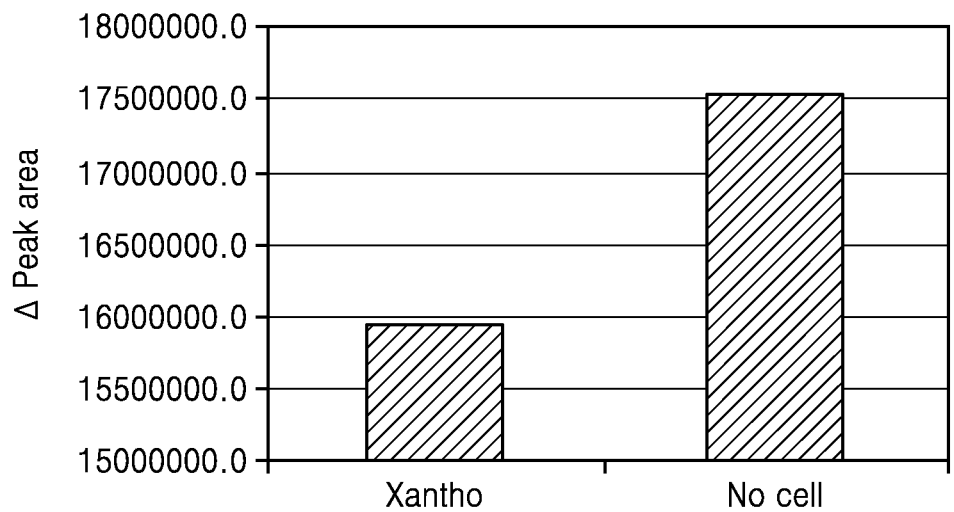
FIG. 13A shows decomposition of tetrafluoromethane by *X. autotrophicus* GJ10.
Figure 13B:
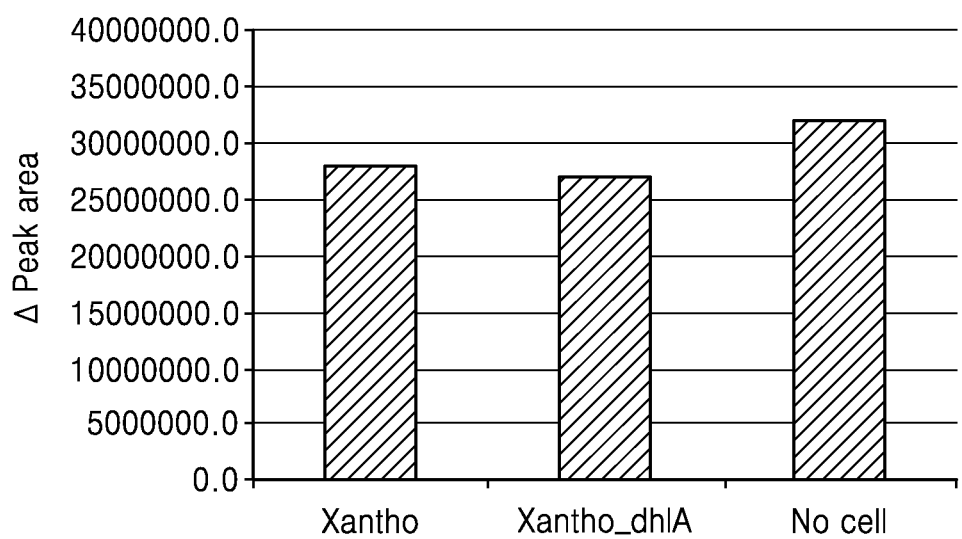
FIG. 13B shows decomposition of tetrafluoromethane by *X. autotrophicus* GJ10 Xantho_dhlA.

A serum bottle containing 10 ml of $2\times10^9$ cells/ml of Xantho_dhlA in the M9 medium and 600 ppm or 1000 ppm of $CF_4$ in the headspace was incubated in a shaking incubator (Daihan Labtech) under stirring at 230 rpm at 30° C. for 48 hours. Thereafter, a headspace concentration of $CF_4$ was analyzed. A negative control was prepared in the same manner, except that $CF_4$ was used in the headspace concentration of 600 ppm or 1000 ppm without cells and *X. autotrophicus* GJ10 was used under the same conditions. The results are given in FIGS. 13A and 13B. In FIGS. 13A and 13B, Xantho represents *X. autotrophicus* GJ10, Xantho_dhlA represents *X. autotrophicus* GJ10 Xantho_dhlA, and the vertical axis represents peak area, namely, Δ peak area.

FIG. 13A shows decomposition of tetrafluoromethane by *X. autotrophicus* GJ10. As shown in FIG. 13A, when the headspace concentration of $CF_4$ was 600 ppm, *X. autotrophicus* GJ10 decreased the amount of tetrafluoromethane by about 12.94%, compared to the control group.

FIG. 13B shows decomposition of tetrafluoromethane by *X. autotrophicus* GJ10 *Xantho_dhlA*. As shown in FIG. 13B, when the headspace concentration of $CF_4$ was 1000 ppm, *X. autotrophicus* GJ10 *Xantho_dhlA* and *X. autotrophicus* GJ10 decreased the amount of tetrafluoromethane by about 16.29% and 12.04%, compared to the control group, respectively. Therefore, *X. autotrophicus* GJ10 *Xantho_dhlA* showed remarkably efficient $CF_4$ decomposition, compared to *X. autotrophicus* GJ10.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of reducing a concentration of $CHF_3$ or $CF_4$ in a sample, the method comprising:

contacting a recombinant *Escherichia* or *Xanthobacter* microorganism with a sample containing $CHF_3$ or $CF_4$, to reduce the concentration of $CHF_3$ or $CF_4$ in the sample, wherein the recombinant microorganism comprises one or more foreign genes encoding a monooxygenase of EC 1.14.13 selected from the group consisting of soluble methane monooxygenase (sMMO) and ammonia monooxygenase;

wherein the monooxygenase acts on carbon-fluorine or carbon-hydrogen bond of the $CHF_3$ or $CF_4$ in the sample;

wherein the recombinant microorganism has an increased monooxygenase activity compared to a parent strain of the recombinant microorganism;

and wherein the sample comprises industrial waste water or waste gas.

2. The method of claim 1, wherein the monooxygenase of EC 1.14.13 is soluble methane monooxygenase (sMMO) from *Methylococcus capsulatus*.

3. The method of claim 1, wherein the contacting is performed in a sealed container.

4. The method of claim 1, wherein the contacting comprises culturing or incubating the recombinant microorganism with the sample containing $CHF_3$ or $CF_4$.

5. The method of claim 1, wherein the contacting comprises culturing the recombinant microorganism in a sealed container under conditions where the recombinant microorganism proliferates.

6. The method of claim 1, wherein reducing the concentration of $CHF_3$ or $CF_4$ in the sample comprises converting $CHF_3$ or $CF_4$ into another material, optionally by cleaving one or more C—F bonds of $CHF_3$ or $CF_4$; or increasing intracellular accumulation of $CHF_3$ or $CF_4$.

7. The method of claim 1, wherein the recombinant microorganism is *Escherichia coli*.

8. The method of claim 1, wherein the recombinant microorganism is *Xanthobacter autotrophicus*.

* * * * *